US012558442B2

(12) United States Patent (10) Patent No.: US 12,558,442 B2

Church et al. (45) Date of Patent: Feb. 24, 2026

(54) BIOLOGICAL FLUID TREATMENT SYSTEMS

(71) Applicant: Cerus Corporation, Concord, CA (US)

(72) Inventors: Daniel Church, Danville, CA (US); Lloyd Ison, Livermore, CA (US); Marc Stern, Oakland, CA (US)

(73) Assignee: Cerus Corporation, Concord, CA (US)

( * ) Notice: Subject to any disclaimer, the term of this patent is extended or adjusted under 35 U.S.C. 154(b) by 29 days.

(21) Appl. No.: 18/649,706

(22) Filed: Apr. 29, 2024

(65) Prior Publication Data

US 2024/0350687 A1     Oct. 24, 2024

Related U.S. Application Data

(63) Continuation of application No. 16/908,577, filed on Jun. 22, 2020, now Pat. No. 12,011,510.

(60) Provisional application No. 62/986,593, filed on Mar. 6, 2020, provisional application No. 62/869,544, filed on Jul. 1, 2019, provisional application No. 62/865,207, filed on Jun. 22, 2019.

(51) Int. Cl.
| | |
|---|---|
| *A61L 2/08* | (2006.01) |
| *A61L 2/084* | (2026.01) |
| *A61L 2/10* | (2006.01) |
| *A61L 2/26* | (2006.01) |
| *A61M 1/36* | (2006.01) |
| *G06F 3/048* | (2013.01) |

(52) U.S. Cl.
CPC ................ *A61L 2/084* (2013.01); *A61L 2/10* (2013.01); *A61L 2/26* (2013.01); *A61M 1/3623* (2022.05); *G06F 3/048* (2013.01); *A61L 2202/122* (2013.01); *A61L 2202/14* (2013.01); *A61L 2202/22* (2013.01)

(58) Field of Classification Search
None
See application file for complete search history.

(56) References Cited

U.S. PATENT DOCUMENTS

| | | | | | |
|---|---|---|---|---|---|
| 3,261,594 | A | * | 7/1966 | Michel | .................. B01F 31/201 |
| | | | | | 366/202 |
| 3,480,015 | A | * | 11/1969 | Gonzalez | .............. A61M 1/025 |
| | | | | | 604/245 |

(Continued)

FOREIGN PATENT DOCUMENTS

| | | |
|---|---|---|
| CN | 1284886 A | 2/2001 |
| CN | 1450916 A | 10/2003 |

(Continued)

OTHER PUBLICATIONS

Alhumaidan, H. et al. (2012). "Current Status of Additive Solution for Platelets," J. Clin Apheresis 27:93-98.

(Continued)

*Primary Examiner* — Holly Kipouros

(74) *Attorney, Agent, or Firm* — MORRISON & FOERSTER LLP

(57) ABSTRACT

Disclosed herein is systems, methods, and apparatuses for treating biological fluids. In some embodiments, the biological fluid treatment system includes a treatment, a platform, an array of light sources, and a display. In some embodiments, the biological fluid treatment system includes a scanner.

35 Claims, 19 Drawing Sheets

(56) References Cited

U.S. PATENT DOCUMENTS

| | | | |
|---|---|---|---|
| 4,227,902 A * | 10/1980 | Olson | B01L 9/02 |
| | | | 55/472 |
| 4,952,812 A * | 8/1990 | Miripol | A61L 2/0011 |
| | | | 250/455.11 |
| 5,167,656 A | 12/1992 | Lynn | |
| 5,221,608 A | 6/1993 | Cimino et al. | |
| 5,288,605 A | 2/1994 | Lin et al. | |
| 5,399,719 A | 3/1995 | Wollowitz et al. | |
| 5,405,343 A | 4/1995 | Mohr | |
| 5,418,130 A | 5/1995 | Platz et al. | |
| 5,459,030 A | 10/1995 | Lin et al. | |
| 5,482,828 A | 1/1996 | Lin et al. | |
| 5,556,958 A | 9/1996 | Carroll | |
| 5,556,993 A | 9/1996 | Wollowitz | |
| 5,559,250 A | 9/1996 | Cook | |
| 5,571,082 A | 11/1996 | Bashikirov | |
| 5,578,736 A | 11/1996 | Wollowitz | |
| 5,585,503 A | 12/1996 | Wollowitz | |
| 5,589,462 A | 12/1996 | Patat | |
| 5,593,823 A | 1/1997 | Wollowitz et al. | |
| 5,618,662 A | 4/1997 | Lin et al. | |
| 5,625,079 A | 4/1997 | Wollowitz et al. | |
| 5,654,443 A | 8/1997 | Wollowitz | |
| 5,691,132 A | 11/1997 | Wollowitz et al. | |
| 5,709,991 A | 1/1998 | Lin et al. | |
| 5,712,085 A | 1/1998 | Wollowitz | |
| 5,871,900 A | 2/1999 | Wollowitz | |
| 5,908,742 A | 6/1999 | Lin et al. | |
| 5,965,349 A | 10/1999 | Lin | |
| 5,972,593 A | 10/1999 | Wollowitz | |
| 6,004,741 A | 12/1999 | Wollowitz | |
| 6,004,742 A | 12/1999 | Wollowitz | |
| 6,017,691 A | 1/2000 | Wollowitz et al. | |
| 6,093,725 A | 7/2000 | Cook et al. | |
| 6,133,460 A | 10/2000 | Wollowitz et al. | |
| 6,143,490 A | 11/2000 | Cook et al. | |
| 6,171,777 B1 | 1/2001 | Cook | |
| 6,177,441 B1 | 1/2001 | Cook et al. | |
| 6,194,139 B1 | 2/2001 | Wollowitz | |
| 6,218,100 B1 | 4/2001 | Wollowitz | |
| 6,251,580 B1 | 6/2001 | Lin | |
| 6,270,952 B1 | 8/2001 | Cook et al. | |
| 6,277,337 B1 | 8/2001 | Goodrich, Jr. et al. | |
| 6,281,225 B1 | 8/2001 | Hearst et al. | |
| 6,410,219 B1 | 6/2002 | Cook et al. | |
| 6,420,570 B1 | 7/2002 | Wollowitz | |
| 6,433,343 B1 | 8/2002 | Cimino et al. | |
| 6,455,286 B1 | 9/2002 | Wollowitz | |
| 6,469,052 B2 | 10/2002 | Wollowitz | |
| 6,503,699 B1 | 1/2003 | Wollowitz et al. | |
| 6,514,987 B1 | 2/2003 | Cook et al. | |
| 6,544,727 B1 | 4/2003 | Hei | |
| 6,548,242 B2 | 4/2003 | Horowitz et al. | |
| 6,565,802 B1 | 5/2003 | Hanley | |
| 6,586,749 B2 | 7/2003 | Cimino | |
| 6,686,480 B2 | 2/2004 | Wollowitz | |
| 6,709,810 B2 | 3/2004 | Cook | |
| 6,843,961 B2 | 1/2005 | Hlavinka et al. | |
| 6,949,753 B2 | 9/2005 | Cimino | |
| 6,951,713 B2 | 10/2005 | Hei et al. | |
| 6,986,867 B2 | 1/2006 | Hanley et al. | |
| 7,025,877 B1 | 4/2006 | De | |
| 7,037,642 B2 | 5/2006 | Hei et al. | |
| 7,105,093 B2 | 9/2006 | De | |
| 7,293,985 B2 | 11/2007 | Cook | |
| 7,425,304 B2 | 9/2008 | De | |
| 7,433,030 B2 | 10/2008 | Waldo et al. | |
| 7,459,695 B2 | 12/2008 | Hanley et al. | |
| 7,601,298 B2 | 10/2009 | Waldo et al. | |
| 7,611,831 B2 | 11/2009 | Hei | |
| 7,655,392 B2 | 2/2010 | Stassinopoulos | |
| 7,788,038 B2 | 8/2010 | Oshita | |
| 7,829,867 B2 | 11/2010 | Hlavinka et al. | |
| 8,296,071 B2 | 10/2012 | Edrich et al. | |
| 8,492,162 B2 | 7/2013 | Kippenhan | |
| 8,778,263 B2 | 7/2014 | Walker et al. | |
| 8,830,449 B1 * | 9/2014 | Lamego | G01N 33/49 |
| | | | 356/40 |
| 8,900,805 B2 | 12/2014 | Mufti et al. | |
| 9,259,525 B2 | 2/2016 | Hei | |
| 9,320,817 B2 | 4/2016 | Walker et al. | |
| 9,713,627 B2 | 7/2017 | Mufti | |
| 10,004,821 B2 | 6/2018 | Dobrinsky | |
| 10,357,516 B2 | 7/2019 | Mufti | |
| 10,506,915 B2 | 12/2019 | Iwasaki | |
| 10,758,868 B2 | 9/2020 | Fulkerson | |
| 10,799,533 B2 | 10/2020 | Corash | |
| 10,842,818 B2 | 11/2020 | Vermeij | |
| 11,096,963 B2 | 8/2021 | Corash et al. | |
| 11,554,185 B2 | 1/2023 | Church et al. | |
| 11,660,365 B2 | 5/2023 | Thompson | |
| 11,883,544 B2 | 1/2024 | Church | |
| 12,011,510 B2 | 6/2024 | Church et al. | |
| 12,214,092 B2 | 2/2025 | Church et al. | |
| 12,343,436 B2 | 7/2025 | Church et al. | |
| 2001/0009756 A1 | 7/2001 | Hei | |
| 2001/0018179 A1 | 8/2001 | Hei | |
| 2002/0006393 A1 | 1/2002 | Wollowitz | |
| 2002/0028432 A1 | 3/2002 | Cook | |
| 2002/0042043 A1 | 4/2002 | Stassinopoulos | |
| 2002/0115585 A1 | 8/2002 | Hei | |
| 2002/0192632 A1 | 12/2002 | Hei | |
| 2003/0035751 A1 | 2/2003 | Hanley et al. | |
| 2003/0062483 A1 | 4/2003 | Cimino | |
| 2003/0105339 A1 | 6/2003 | Wollowitz | |
| 2003/0113704 A1 | 6/2003 | Stassinopoulos | |
| 2003/0146162 A1 | 8/2003 | Metzel et al. | |
| 2003/0185804 A1 | 10/2003 | Wollowitz et al. | |
| 2003/0207247 A1 | 11/2003 | Stassinopoulos et al. | |
| 2003/0219354 A1 | 11/2003 | Hlavinka et al. | |
| 2004/0021809 A1 | 2/2004 | Sumiyoshi et al. | |
| 2004/0029897 A1 | 2/2004 | Cook | |
| 2004/0088189 A1 | 5/2004 | Veome et al. | |
| 2004/0172007 A1 | 9/2004 | Grimm et al. | |
| 2004/0180321 A1 | 9/2004 | Cook | |
| 2004/0185544 A9 | 9/2004 | Hei | |
| 2004/0185553 A9 | 9/2004 | Hei | |
| 2004/0197343 A1 | 10/2004 | Dubensky et al. | |
| 2004/0228877 A1 | 11/2004 | Dubensky et al. | |
| 2005/0142542 A1 | 6/2005 | Hei | |
| 2005/0175625 A1 | 8/2005 | Jaffee et al. | |
| 2005/0202395 A1 | 9/2005 | Edrich et al. | |
| 2005/0249748 A1 | 11/2005 | Dubensky et al. | |
| 2005/0281783 A1 | 12/2005 | Kinch et al. | |
| 2006/0093999 A1 | 5/2006 | Hei | |
| 2006/0115466 A1 | 6/2006 | Stassinopoulos | |
| 2006/0197031 A1 | 9/2006 | De et al. | |
| 2006/0221329 A1 * | 10/2006 | Waldo | G01J 1/4228 |
| | | | 356/213 |
| 2007/0031457 A1 | 2/2007 | Dubensky et al. | |
| 2007/0190029 A1 | 8/2007 | Pardoll et al. | |
| 2007/0190063 A1 | 8/2007 | Bahjat et al. | |
| 2007/0207170 A1 | 9/2007 | Dubensky et al. | |
| 2007/0207171 A1 | 9/2007 | Dubensky et al. | |
| 2007/0235376 A1 | 10/2007 | Daniel | |
| 2009/0250626 A1 | 10/2009 | Schlesser et al. | |
| 2010/0133160 A1 | 6/2010 | Hei | |
| 2011/0209212 A1 | 8/2011 | Newlin et al. | |
| 2011/0286987 A1 | 11/2011 | Mufti | |
| 2012/0070339 A1 | 3/2012 | Lawal | |
| 2012/0073614 A1 | 3/2012 | Otani | |
| 2012/0153783 A1 | 6/2012 | Shoenfeld | |
| 2012/0313014 A1 | 12/2012 | Stibich et al. | |
| 2013/0320299 A1 | 12/2013 | Li | |
| 2013/0323128 A1 | 12/2013 | Owen et al. | |
| 2014/0303547 A1 | 10/2014 | Loupis et al. | |
| 2014/0346370 A1 | 11/2014 | Dobrinsky et al. | |
| 2014/0353519 A1 | 12/2014 | Wang | |
| 2015/0157665 A1 | 6/2015 | Mufti | |
| 2015/0299000 A1 | 10/2015 | Smith et al. | |
| 2016/0324997 A1 * | 11/2016 | Dayton | A61L 2/10 |
| 2016/0354533 A1 | 12/2016 | Hei | |
| 2017/0014538 A1 | 1/2017 | Rantala | |
| 2017/0027986 A1 | 2/2017 | Corash et al. | |

(56) References Cited

U.S. PATENT DOCUMENTS

| | | | |
|---|---|---|---|
| 2017/0028121 A1 | 2/2017 | Manzella et al. | |
| 2017/0050046 A1 | 2/2017 | Walder et al. | |
| 2017/0054687 A1 | 2/2017 | Ishigaki | |
| 2017/0202882 A1 | 7/2017 | Vermeij | |
| 2017/0252474 A1 | 9/2017 | Thompson et al. | |
| 2017/0304363 A1 | 10/2017 | Corash | |
| 2018/0008639 A1 | 1/2018 | Mufti | |
| 2018/0113066 A1 | 4/2018 | Freitag et al. | |
| 2018/0147306 A1 | 5/2018 | Crawley et al. | |
| 2018/0184985 A1 | 7/2018 | Håkansson et al. | |
| 2018/0185484 A1 | 7/2018 | Greenman et al. | |
| 2018/0193500 A1 | 7/2018 | Safavi et al. | |
| 2018/0289873 A1 | 10/2018 | David | |
| 2018/0318348 A1 | 11/2018 | Corash et al. | |
| 2018/0369437 A1 | 12/2018 | Grossman et al. | |
| 2019/0041308 A1* | 2/2019 | Schryver | G01N 1/44 |
| 2019/0085289 A1 | 3/2019 | Greenman | |
| 2019/0099543 A1 | 4/2019 | Sasaki | |
| 2019/0100718 A1 | 4/2019 | Estes et al. | |
| 2019/0209718 A1 | 7/2019 | Church | |
| 2019/0321407 A1 | 10/2019 | Erickson et al. | |
| 2019/0369087 A1 | 12/2019 | North et al. | |
| 2020/0063179 A1 | 2/2020 | Eghbal | |
| 2020/0078406 A1 | 3/2020 | Weiner et al. | |
| 2020/0397931 A1 | 12/2020 | Church et al. | |
| 2020/0397935 A1 | 12/2020 | Church et al. | |
| 2020/0405891 A1 | 12/2020 | Church et al. | |
| 2021/0038802 A1 | 2/2021 | Madsen | |
| 2021/0052804 A1 | 2/2021 | Madsen | |
| 2021/0187020 A1 | 6/2021 | Corash et al. | |
| 2021/0260114 A1 | 8/2021 | Corash et al. | |
| 2021/0322479 A1 | 10/2021 | Vermeij | |
| 2022/0031917 A1 | 2/2022 | Cahyadi et al. | |
| 2022/0118136 A1 | 4/2022 | Church et al. | |
| 2023/0226232 A1 | 7/2023 | Church et al. | |
| 2024/0108767 A1 | 4/2024 | Church | |

FOREIGN PATENT DOCUMENTS

| | | | |
|---|---|---|---|
| CN | 203017432 U | 6/2013 | |
| CN | 105412960 A | 3/2016 | |
| CN | 106421864 A | 2/2017 | |
| CN | 107075478 A | 8/2017 | |
| CN | 107852359 A | 3/2018 | |
| EP | 1181061 B1 | 8/2006 | |
| EP | 3009946 A1 | 4/2016 | |
| JP | 2006501978 A | 1/2006 | |
| JP | 2006505349 A | 2/2006 | |
| JP | 2011036683 A | 2/2011 | |
| JP | 2015042266 A | 3/2015 | |
| JP | 2015171440 A | 10/2015 | |
| JP | 2017029717 A | 2/2017 | |
| JP | 2017077247 A | 4/2017 | |
| JP | 2017153966 A | 9/2017 | |
| JP | 2017184725 A | 10/2017 | |
| WO | 199300005 A1 | 1/1993 | |
| WO | 199317553 A1 | 9/1993 | |
| WO | 199403054 A1 | 2/1994 | |
| WO | 199420090 A1 | 9/1994 | |
| WO | 199427433 A1 | 12/1994 | |
| WO | 199428120 A1 | 12/1994 | |
| WO | 199500141 A1 | 1/1995 | |
| WO | 199512973 A1 | 5/1995 | |
| WO | 199519705 A1 | 7/1995 | |
| WO | 199608965 A1 | 3/1996 | |
| WO | 199614737 A1 | 5/1996 | |
| WO | 199614739 A1 | 5/1996 | |
| WO | 199614740 A1 | 5/1996 | |
| WO | 199639815 A1 | 12/1996 | |
| WO | 199639818 A1 | 12/1996 | |
| WO | 199639820 A1 | 12/1996 | |
| WO | 199640857 A1 | 12/1996 | |
| WO | 199721346 A1 | 6/1997 | |
| WO | 199737536 A1 | 10/1997 | |
| WO | 199818908 A1 | 5/1998 | |
| WO | 199830327 A1 | 7/1998 | |
| WO | 199830545 A1 | 7/1998 | |
| WO | 199903976 A2 | 1/1999 | |
| WO | 199903976 A3 | 5/1999 | |
| WO | 199926476 A1 | 6/1999 | |
| WO | 199934839 A1 | 7/1999 | |
| WO | 199934914 A1 | 7/1999 | |
| WO | 199934915 A1 | 7/1999 | |
| WO | 199959645 A1 | 11/1999 | |
| WO | 199963981 A2 | 12/1999 | |
| WO | 199963981 A3 | 4/2000 | |
| WO | 200074731 A1 | 12/2000 | |
| WO | 200191775 A2 | 12/2001 | |
| WO | 200191775 A3 | 6/2002 | |
| WO | 02053209 A1 | 7/2002 | |
| WO | 2003047650 A2 | 6/2003 | |
| WO | 2003049784 A2 | 6/2003 | |
| WO | 2003049784 A3 | 6/2003 | |
| WO | 2003061379 A2 | 7/2003 | |
| WO | 2003065787 A2 | 8/2003 | |
| WO | 2003078023 A1 | 9/2003 | |
| WO | 2003061379 A3 | 10/2003 | |
| WO | 2003090794 A1 | 11/2003 | |
| WO | 2003065787 A3 | 12/2003 | |
| WO | 2003047650 A3 | 2/2004 | |
| WO | 2004018471 A1 | 3/2004 | |
| WO | 2004033081 A2 | 4/2004 | |
| WO | 2004044810 A1 | 5/2004 | |
| WO | 2004033081 A3 | 6/2004 | |
| WO | 2004049914 A2 | 6/2004 | |
| WO | 2004050029 A2 | 6/2004 | |
| WO | 2004050848 A2 | 6/2004 | |
| WO | 2004050897 A2 | 6/2004 | |
| WO | 2004050897 A3 | 8/2004 | |
| WO | 2004050029 A3 | 10/2004 | |
| WO | 2004084936 A2 | 10/2004 | |
| WO | 2004050848 A3 | 12/2004 | |
| WO | 2004110481 A2 | 12/2004 | |
| WO | 2004049914 A3 | 2/2005 | |
| WO | 2005009463 A2 | 2/2005 | |
| WO | 2004110481 A3 | 3/2005 | |
| WO | 2005037233 A2 | 4/2005 | |
| WO | 2004084936 A3 | 6/2005 | |
| WO | 2005009463 A3 | 6/2005 | |
| WO | 2005067460 A2 | 7/2005 | |
| WO | 2005071088 A2 | 8/2005 | |
| WO | 2005092372 A2 | 10/2005 | |
| WO | 2005071088 A3 | 11/2005 | |
| WO | 2005037233 A3 | 1/2006 | |
| WO | 2006021314 A2 | 3/2006 | |
| WO | 2006050328 A1 | 5/2006 | |
| WO | 2005092372 A3 | 6/2006 | |
| WO | 2005067460 A3 | 10/2006 | |
| WO | 2007022511 A2 | 2/2007 | |
| WO | 2007022520 A2 | 2/2007 | |
| WO | 2007022520 A3 | 5/2007 | |
| WO | 2007022511 A3 | 9/2007 | |
| WO | 2007103225 A2 | 9/2007 | |
| WO | 2007103261 A2 | 9/2007 | |
| WO | 2007117371 A2 | 10/2007 | |
| WO | 2007103225 A3 | 5/2008 | |
| WO | 2007103261 A3 | 12/2008 | |
| WO | 2007117371 A3 | 12/2008 | |
| WO | 2008156813 A1 | 12/2008 | |
| WO | 2009126786 A2 | 10/2009 | |
| WO | 2009126786 A3 | 7/2010 | |
| WO | 2011120172 A1 | 10/2011 | |
| WO | 2012018484 A2 | 2/2012 | |
| WO | 2012018484 A3 | 4/2012 | |
| WO | 2012071135 A2 | 5/2012 | |
| WO | 2012071135 A3 | 8/2012 | |
| WO | 2014022717 A1 | 2/2014 | |
| WO | 2014051882 A1 | 4/2014 | |
| WO | 2014051906 A1 | 4/2014 | |
| WO | 2015168783 A1 | 11/2015 | |
| WO | 2016014854 A1 | 1/2016 | |
| WO | 2016057965 A1 | 4/2016 | |
| WO | 2016115535 A1 | 7/2016 | |
| WO | 2016149055 A2 | 9/2016 | |

(56)　　　　References Cited

FOREIGN PATENT DOCUMENTS

| | | | |
|---|---|---|---|
| WO | 2016149055 | A3 | 12/2016 |
| WO | 2016210374 | A1 | 12/2016 |
| WO | 2017009534 | A1 | 1/2017 |
| WO | 2017047119 | A1 | 3/2017 |
| WO | 2017062260 | A2 | 4/2017 |
| WO | 2017070619 | A1 | 4/2017 |
| WO | 2017062260 | A3 | 5/2017 |
| WO | 2017120545 | A2 | 7/2017 |
| WO | 2017120545 | A3 | 8/2017 |
| WO | 2018119462 | A1 | 6/2018 |
| WO | 2018125994 | A1 | 7/2018 |
| WO | 2018161020 | A1 | 9/2018 |
| WO | 2019060610 | A1 | 3/2019 |
| WO | 2019133929 | A1 | 7/2019 |
| WO | 2020061537 | A1 | 3/2020 |
| WO | 2020263745 | A1 | 12/2020 |
| WO | 2020264421 | A1 | 12/2020 |
| WO | 2022087580 | A1 | 4/2022 |

OTHER PUBLICATIONS

Anonymous (2018). "DS9900 Series Corded Hybrid Imager for Labs," ZEBRA, 4 pages.

International Preliminary Report on Patentability, issued Apr. 13, 2023 for PCT Application No. PCT/US2021/071920, filed Oct. 18, 2021, 7 pages.

International Preliminary Report on Patentability, issued Dec. 28, 2021, for PCT Application No. PCT/US2020/038950, filed Jun. 22, 2020, 9 pages.

International Preliminary Report on Patentability, issued Dec. 28, 2021, for PCT Application No. PCT/US2020/039011, filed Jun. 22, 2020, 13 pages.

International Preliminary Report on Patentability, issued Dec. 28, 2021, for PCT Application No. PCT/US2020/039984, filed Jun. 26, 2020, 8 pages.

International Preliminary Report on Patentability, issued Jun. 30, 2020, for PCT Application No. PCT/US2018/068048, 11 pages.

International Search Report and Written Opinion, mailed Aug. 19, 2002, for PCT Application No. PCT/US2020/038950, filed Jun. 22, 2020, 16 pages.

International Search Report and Written Opinion, mailed Dec. 23, 2020, for PCT Application No. PCT/US2020/039011, filed Jun. 22, 2020, 18 pages.

International Search Report and Written Opinion, mailed Jan. 17, 2022, for PCT Application No. PCT/US2021/0071920, filed Oct. 18, 2021, 14 pages.

International Search Report and Written Opinion, mailed May 3, 2019, for PCT Application No. PCT/US2018/068048, filed on Dec. 28, 2018 18 pages.

International Search Report and Written Opinion, mailed Sep. 29, 2020, for PCT Application No. PCT/US2020/039984, filed Jun. 26, 2020, 14 pages.

Irsch, J. et al. (2011, e-pub. Jan. 27, 2011). "Pathogen Inactivation of Platelet and Plasma Blood Components for Transfusion Using the INTERCEPT Blood System™," Transfus. Med. Hemother. 38:19-31.

Oxford English Dictionary (Date Unknown). "System," located at https://www.oed.com/search/dictionary/?scope=Entries&q=system &tl=true, last visited on Sep. 26, 2023, one page.

Prodouz, K.N. et al. (1992). "Effects of Two Viral Inactivation Methods on Platelets: Laser-UV Radiation and Merocyanie 540-Mediated Photoinactivation," Blood Cells 18(1): 101-116.

Prowse, C.V. (Apr. 2013, e-pub. Nov. 8, 2012). "Component Pathogen Inactivation: A Critical Review," Vox Sanguinis, 104(3):183-199.

Reikvam, H. et al. (2010). "The Mirasol® Pathogen Reduction Technology System and Quality of Platelets Stored in Platelet Additive Solution," Blood Transfus. 8:186-192.

Ringwald, J. et al. (Apr. 2006). "The New Generation of Platelet Additivie Solution for Storage at 22: Development and Current Experience," Transfusion Medicine Reviews, 20(2):158-164.

Schlenke, P. (2014, e-pub. Jul. 21, 2014). "Pathogen Inactivation Technologies for Cellular Blood Components: an Update," Transfus. Med. Hemother. 41:309-325.

Schlenke, P. et al. (2008). "Photochemical Treatment Of Plasma With Amotosalen and UVA Light: Process Validation In Three European Blood Centers," Transfusion 48:697-705, 9 pages.

Seltsam, A. et al. (2011, e-pub. Jan. 22, 2011). "UVC Irraditation For Pathogen Reduction of Platelet Concentrates and Plasma," Transfusion Medicine and Hemotherapy 38:43-54.

Sofer, G. (Aug. 2002). "Virus Inactivation In The 1990s—and Into the 21st Century: Part 2, Red Blood Cells and Platelets," BioPharm pp. 42-49.

U.S. Appl. No. 09/238,355, Greenman, W. et al, filed on Jan. 27, 1999. (Copy not submitted herewith pursuant to the waiver of 37 C.F.R. § 1.98(a)(2)(iii) issued by the Office on Sep. 21, 2004.).

* cited by examiner

BIOLOGICAL FLUID TREATMENT SYSTEMS

CROSS-REFERENCE TO RELATED APPLICATIONS

This application is a Continuation application of U.S. application Ser. No. 16/908,577, filed on Jun. 22, 2020, which claims priority to U.S. Provisional Patent Application No. 62/865,207, filed Jun. 22, 2019, U.S. Provisional Patent Application No. 62/869,544, filed Jul. 1, 2019, and U.S. Provisional Patent Application No. 62/986,593, filed Mar. 6, 2020, the disclosures of which are incorporated herein by reference in their entirety.

FIELD

This disclosure relates generally to systems, methods, and apparatuses for treating biological fluids, including mixtures of biological fluids and photochemical agents, with light.

BACKGROUND

Systems and methods for treating biological fluids with light are well known. For example, U.S. Pat. Nos. 7,459,695, 6,986,867, and 5,593,823 describe a system for treating a biological fluid with light to inactivate pathogens in the biological fluid. Light is emitted within a selected range of wavelengths that are effective to inactivate pathogens in the biological fluid, particularly by photochemical inactivation of pathogens. Other systems and methods for treating biological fluids with light may include, for example, systems and methods described in U.S. Pat. Nos. 6,843,961, 7,829, 867, 9,320,817 and 8,778,263, and Schlenke, 2014, Transfus. Med. Hemother. 41:309-325.

For blood products including for example, platelets and plasma components and their derivatives, it is important to ensure that the blood products are free of pathogens to minimize the risk of infecting an individual receiving a blood product. Testing for the presence of a pathogen in blood is limited by the pathogens for which tests are available and assay sensitivity. As an alternative or supplement to testing for pathogens, methods are known in the art for inactivating pathogens using various compound (e.g., chemical, photochemical)-based inactivation methods to reduce the risk of transfusion-transmitted infection (e.g., as disclosed in Schlenke et al., Transfus Med Hemother, 2014, 41, 309-325 and Prowse, Vox Sanguinis, 2013, 104, 183-199). Photochemical pathogen inactivation systems based on psoralens and ultraviolet light for treating blood products include the commercially available INTERCEPT® Blood System (Cerus Corporation), which utilizes disposable processing sets and an ultraviolet light illumination device (INT-100). Blood products such as plasma or platelets are mixed with a psoralen, amotosalen, in the processing sets and then illuminated with ultraviolet A light, followed by removal of residual amotosalen and photoproducts thereof with a compound adsorption device (CAD) portion of the processing sets. Multiple different disposable processing sets may be used, depending on the type of blood product to be treated and particular properties of those blood products, such as for example volume and platelet number. Different illumination requirements may limit the ability to treat multiple processing sets in the same illumination device, thereby impacting efficiency of a blood collection center.

Also, previous illuminator systems may be horizontally wide and limited to treatment chambers in only one horizontal layer.

While previous systems and methods for treating biological fluids, such as blood products described herein, have generally performed satisfactorily, it is desirable to develop improved systems and methods, including systems and methods disclosed herein comprising multiple treatment chambers and design features that may provide a variety of advantageous benefits for higher throughput treatment of biological fluids, ease of operator use, and/or reduced instances of user operator error that may impact the systems and/or biological fluids being treated.

BRIEF SUMMARY

Disclosed herein are systems, methods, and apparatuses for treating biological fluids. In some embodiments, the biological fluid treatment system includes a treatment chamber configured to receive biological fluids, a platform configured to carry the biological fluid to be positioned in the treatment chamber, an array of light sources positioned to illuminate the biological fluid in the treatment chamber, and a display configured for displaying a graphical user interface (GUI). In some embodiments, the biological fluid treatment system includes a scanner configured to obtain identifying information associated with a first biological fluid, a second biological fluid, or both the first biological fluid and the second biological fluid.

In some embodiments, a biological fluid treatment system comprises: a first treatment chamber configured to receive a first biological fluid; a second treatment chamber configured to receive a second biological fluid; a first platform configured to carry the first biological fluid and to be positioned in the first treatment chamber; a second platform configured to carry the second biological fluid and to be positioned in the second treatment chamber; a first array of light sources positioned to illuminate the first biological fluid in the first treatment chamber and a second array of light sources positioned to illuminate the second biological fluid in the second treatment chamber; a display; one or more processors; and a memory including instructions, which when executed by the one or more processors, cause the one or more processors to perform a method comprising providing for display, on the display, a GUI including a plurality of GUI objects associated with treatment of the first biological fluid by illumination from the first array of light sources or associated with treatment of the second biological fluid by illumination from the second array of light sources.

In some embodiments, the first array of light sources and the second array of light sources are configured to illuminate the first biological fluid and the second biological fluid, respectively, with ultraviolet light. In some embodiments, each of the arrays of light sources comprises a respective first light source channel configured to emit ultraviolet light with a first peak wavelength of the array of from about 315 nm to about 350 nm. In some embodiments, each of the arrays of light sources comprises a respective first light source channel configured to emit ultraviolet light with a first peak wavelength of the array of from about 330 nm to about 350 nm. In some embodiments, each of the arrays of light sources comprises a respective first light source channel configured to emit ultraviolet light with a first peak wavelength of the array of from about 340 nm to about 350 nm. In some embodiments, each of the arrays of light sources comprises a respective first light source channel configured to emit ultraviolet light with a first peak wavelength of the array within a range of 345±5 nm. In some embodiments, each of the arrays of light sources comprises a respective first light source channel configured to emit ultraviolet light with a first peak wavelength of the array of from about 315 nm to about 335 nm. In some embodiments, each of the arrays of light sources comprises a respective second light source channel configured to emit ultraviolet light with a second peak wavelength of the array, wherein the second peak wavelength differs from the first peak wavelength by at least 5 nanometers.

In some embodiments, for each of the arrays of light sources, the respective first light source channel comprises one or more light sources, each of which emits light having a full-width half-maximum (FWHM) spectral bandwidth of less than 20 nanometers. In some embodiments, for each of the arrays of light sources, the respective second light source channel comprises one or more light sources, each of which emits light having a full-width half-maximum (FWHM) spectral bandwidth of less than 20 nanometers.

In some embodiments, the system further comprises: a third array of light sources facing an opposite direction as the first array of light sources and positioned to illuminate the first biological fluid in the first treatment chamber, and; a fourth array of light sources facing an opposite direction as the second array of light sources and positioned to illuminate the second biological fluid in the second treatment chamber; wherein the method further comprises providing for display, on the display, a graphical user interface (GUI) including a plurality of GUI objects associated with treatment of the first biological fluid by illumination from the third array of light sources or associated with treatment of the second biological fluid by illumination from the fourth array of light sources.

In some embodiments, each of the third and fourth arrays of light sources comprises a respective first light source channel configured to emit ultraviolet light with a first peak wavelength of the array of from about 315 nm to about 350 nm. In some embodiments, each of the third and fourth arrays of light sources comprises a respective first light source channel configured to emit ultraviolet light with a first peak wavelength of the array of from about 330 nm to about 350 nm. In some embodiments, each of the third and fourth arrays of light sources comprises a respective first light source channel configured to emit ultraviolet light with a first peak wavelength of the array of from about 340 nm to about 350 nm. In some embodiments, each of the third and fourth arrays of light sources comprises a respective first light source channel configured to emit ultraviolet light with a first peak wavelength of the array within a range of 345±5 nm. In some embodiments, each of the third and fourth arrays of light sources comprises a respective first light source channel configured to emit ultraviolet light with a first peak wavelength of the array of from about 315 nm to about 335 nm. In some embodiments, each of the third and fourth arrays of light sources comprises a respective second light source channel configured to emit ultraviolet light with a second peak wavelength of the array, wherein the second peak wavelength differs from the first peak wavelength by at least 5 nanometers.

In some embodiments, for each of the third and fourth arrays of light sources, the respective first light source channel comprises one or more light sources, each of which emits light having a full-width half-maximum (FWHM) spectral bandwidth of less than 20 nanometers. In some embodiments, for each of the third and fourth arrays of light sources, the respective second light source channel comprises one or more light sources, each of which emits light having a full-width half-maximum (FWHM) spectral bandwidth of less than 20 nanometers.

In some embodiments, each of the arrays of light sources (e.g., first array, second array, third array, fourth array) comprises one or more light sources, each of which is a light-emitting diode, and wherein, for each of the arrays of light sources, the respective ultraviolet light is emitted by the respective one or more light sources.

In some embodiments, the first platform is slideably moveable for introducing and removing the first biological fluid into and out of the first treatment chamber and the second platform is slideably moveable for introducing and removing the second biological fluid into and out of the second treatment chamber.

In some embodiments, the system further comprises a housing configured to enclose the first treatment chamber, the second treatment chamber, the first platform, the second platform, the first array of light sources, the second array of light sources, the display, the one or more processors, and the memory.

In some embodiments, the system further comprises a scanner configured to obtain identifying information associated with the first biological fluid, the second biological fluid, or both the first biological fluid and the second biological fluid. In some embodiments, the scanner is one of the group comprising a barcode scanner, QR code scanner, and a RFID scanner. In some embodiments, the identifying information is conveyed in the transmittable form of a radio wave of an RFID tag on a container (e.g., single container) for containing the first biological fluid or the second biological fluid, or at least one of one or more containers of a multi-container assembly for containing the first biological fluid or the second biological fluid, and the method further comprises obtaining, by the scanner, the identifying information conveyed in the radio wave from the RFID tag on the container. In some embodiments, the identifying information is in a visible form of a barcode or a QR code on a container (e.g., single container) for containing the first biological fluid or the second biological fluid, and the method further comprises obtaining, by the scanner, the barcode or the QR code on the container. In some embodiments, the identifying information is in a visible form of a barcode or a QR code on at least one of one or more containers of a multi-container assembly for containing the first biological fluid or the second biological fluid, and the method further comprises obtaining, by the scanner, the barcode or the QR code on the at least one of the one or more containers. In some embodiments, the scanner is configured to obtain the identifying information conveyed in a radio wave form from an RFID tag on a container (e.g., single container) for containing the first biological fluid or the second biological fluid, or at least one of one or more containers of a multi-container assembly for containing the first biological fluid or the second biological fluid, when the container is positioned on the first platform or the second platform. In some embodiments, the scanner is configured to obtain the identifying information in a visible form on a container (e.g., single container) for containing the first biological fluid or the second biological fluid when the container is positioned on the first platform or the second platform. In some embodiments, the scanner is configured to obtain the identifying information in a visible form on at least one of the one or more containers of a multi-container assembly for containing the first biological fluid or the second biological fluid when the one or more containers is positioned on the first platform or the second platform. In some embodiments, the identifying information is multiple sets of identifying information in a visible form on a container (e.g., single container) for containing the first biological fluid or the second biological fluid, and the scanner is a multi-scan scanner configured to obtain the multiple sets of identifying information (e.g., each of the multiple sets of identifying information, all of the multiple sets of identifying information) in a multi-scan operation. In some embodiments, the identifying information is multiple sets of identifying information in a visible form on one or more containers of a multi-container assembly for containing the first biological fluid or the second biological fluid, and the scanner is a multi-scan scanner configured to obtain the multiple sets of identifying information (e.g., each of the multiple sets of identifying information, all of the multiple sets of identifying information) in a multi-scan operation. In some embodiments, the identifying information is multiple sets of identifying information conveyed in a transmittable form from tags on a container (e.g., single container) for containing the first biological fluid or the second biological fluid, and the scanner is a multi-scan scanner configured to obtain the multiple sets of identifying information (e.g., each of the multiple sets of identifying information, all of the multiple sets of identifying information) in a multi-scan operation. In some embodiments, the identifying information is multiple sets of identifying information conveyed in a transmittable form from tags on one or more containers of the multi-container assembly for containing the first biological fluid or the second biological fluid, and the scanner is a multi-scan scanner configured to obtain the multiple sets of identifying information (e.g., each of the multiple sets of identifying information, all of the multiple sets of identifying information) in a multi-scan operation.

In some embodiments, wherein the scanner is integrated or embedded in a fixed position in the housing and coupled to the one or more processors. In some embodiments, the scanner is located inside the first treatment chamber, the second treatment chamber, or both the first and the second treatment chambers. In some embodiments, the scanner is located at a first opening of the first treatment chamber or at a second opening of the second treatment chamber. In some embodiments, the scanner is located external to the first treatment chamber and the second treatment chamber. In some embodiments, the scanner is a handheld scanner that is wirelessly coupled to the one or more processors. In some embodiments, the scanner is a handheld scanner that is coupled to the one or more processors by wired connection.

In some embodiments, the first treatment chamber and the second treatment chamber are arranged horizontally such that the first biological fluid and the second biological fluid, when positioned on the first platform and on the second platform, respectively, are within a same plane. In some embodiments, the first treatment chamber and the second treatment chamber are arranged vertically such that the first biological fluid and the second biological fluid, when positioned on the first platform and on the second platform, respectively, are in parallel planes.

In some embodiments, the system further comprises a first panel movable between a closed position and an open position, wherein the first panel covers a first opening to the first treatment chamber in the closed position, wherein the first panel uncovers the first opening to the first treatment chamber in the open position, wherein an exterior of the first panel includes one or more of the group comprising a protruding handle and a recess handle. In some embodiments, the system further comprises a first panel movable between a closed position and an open position, wherein the first panel covers a first opening to the first treatment chamber in the closed position, wherein the first panel uncovers the first opening to the first treatment chamber in the open position, wherein the entire exterior of the first panel lacks any handle. In some embodiments, the first panel is configured to be locked to remain in the closed position, and configured to be unlocked in response to an input. In some embodiments, the input is a user input, such as for example a user's manual input (e.g., touch or hover) on a touchscreen, a user's voice command (e.g., detected by a microphone), or a user's visual motion (e.g., hand motion or gesture, object in a swiping motion) to unlock the panel.

In some embodiments, the first platform comprises the first panel. In some embodiments, the first platform comprises: an outer region comprising: the first panel movable between a closed position and an open position, the outer region configured to remain in a fixed position when the first panel is in the closed position, and first support structure; and an inner region configured to move to agitate the first biological fluid during a time period in which the outer region is in a fixed position, wherein the first support structure of the outer region structurally supports the inner region. In some embodiments, the inner region of the first platform configured to move to agitate the first biological fluid comprises an inner region assembly comprising: one or more removable inner region portions configured to carry a container containing the first biological fluid; and an inner region support structure that structurally supports the one or more removable inner region portions and that is movable to agitate the first biological fluid carried by the one or more removable inner region portions.

In some embodiments, the outer region comprises a motor configured to generate motion, wherein the inner region is configured to agitate the first biological fluid based on the motion generated by the motor. In some embodiments, the system is configured to control (e.g., adjustably control) one or more aspects of the movement of the inner region to agitate the first biological fluid, such as offset, speed, acceleration, and deceleration. In some embodiments, the motor is located at a position on the right or on the left of where the first biological fluid is to be carried by the first platform. In some embodiments, the motor is located at a position in front of or to the rear of where the first biological fluid is to be carried by the first platform.

In some embodiments, the second platform comprises: a second panel movable between a closed position and an open position, wherein the second panel covers a second opening to the second treatment chamber in the closed position, wherein the second panel uncovers the second opening to the second treatment chamber in the open position; an outer region comprising: the second panel movable between a closed position and an open position, the outer region configured to remain in a fixed position when the second panel is in the closed position, and second support structure; and an inner region configured to move to agitate the second biological fluid during a time period in which the outer region is in a fixed position, wherein the second support structure of the output region structurally supports the inner region. In some embodiments, the inner region of the second platform configured to move to agitate the second biological fluid comprises an inner region assembly comprising: one or more removable inner region portions configured to carry a container containing the second biological fluid; and an inner region support structure that structurally supports the one or more removable inner region portions and that is movable to agitate the second biological fluid carried by the one or more removable inner region portions.

In some embodiments, the first platform and second platform each comprises a first compartment and a second compartment, the first and second compartments configured to carry a multi-container assembly containing the biological fluid of a respective platform, wherein the first compartment of the first platform is configured to carry a first container of a first multi-container assembly, the first container containing the first biological fluid, and wherein the first compartment is positioned such that the first array of light sources is configured to illuminate the first container when the first platform is positioned in the first treatment chamber; wherein the second compartment of the first platform is configured to carry one or more additional containers of the first multi-container assembly, the one or more additional containers not containing the first biological fluid, and wherein the second compartment is positioned such that the first array of light sources is not configured to illuminate the one or more additional containers when the first platform is positioned in the first treatment chamber; wherein the first compartment of the second platform is configured to carry a first container of a second multi-container assembly, the first container containing the second biological fluid, and wherein the first compartment is positioned such that the second array of light sources is configured to illuminate the first container when the second platform is positioned in the second treatment chamber; and wherein the second compartment of the second platform is configured to carry one or more additional containers of the second multi-container assembly, the one or more additional containers not containing the second biological fluid, and wherein the second compartment is positioned such that the second array of light sources is not configured to illuminate the one or more additional containers when the second platform is positioned in the second treatment chamber.

In some embodiments, the display is a touchscreen configured to display the GUI including the plurality of GUI objects, and the GUI objects are responsive to touch inputs on the touchscreen. In some embodiments, the method further comprises: receiving an input associated with a selection of a GUI object; and in response to receiving the input, performing a biological fluid treatment operation.

In some embodiments, any of the systems provided herein (e.g., aforementioned systems) may perform a method of treating one or more biological fluids comprising: illuminating a first biological fluid of the one or more biological fluids with ultraviolet light (e.g., ultraviolet light with a first peak wavelength of from about 315 nm to about 350 nm) emitted by a set of one or more first light sources, wherein the first biological fluid is admixed with a pathogen inactivation compound (e.g., photoactive pathogen inactivation compound, psoralen, amotosalen), wherein: 1) each of the one or more first light sources emits light having a full-width half-maximum (FWHM) spectral bandwidth of less than 20 nanometers, and/or 2) each of the one or more first light sources is a light-emitting diode (LED); and wherein illuminating the first biological fluid occurs for a duration and at an intensity sufficient to inactivate a pathogen in the first biological fluid. In some embodiments, the method of treating the one or more biological fluids may further comprise: illuminating a second biological fluid of the one or more biological fluids with ultraviolet light (e.g., ultraviolet light with a second peak wavelength of from about 315 nm to about 350 nm) emitted by a set of one or more second light sources, wherein the second biological fluid is admixed with a pathogen inactivation compound (e.g., photoactive pathogen inactivation compound, psoralen, amotosalen), wherein: 1) each of the one or more second light sources emits light having a full-width half-maximum (FWHM) spectral bandwidth of less than 20 nanometers, and/or 2) each of the one or more second light sources is a light-emitting diode (LED); and wherein illuminating the second biological fluid occurs for a duration and at an intensity sufficient to inactivate a pathogen in the second biological fluid.

In some embodiments, each of the first platform and the second platform is configured to carry the first and second biological fluids respectively in a first flexible container and a second flexible container respectively, each with a volume capacity up to about 3000 mL. In some embodiments, each of the first platform and the second platform is configured to carry the first and second biological fluids respectively in a first flexible container and a second flexible container respectively, each with a volume capacity up to about 1500 mL. In some embodiments, each of the first platform and the second platform is configured to carry the first and second biological fluids respectively in a first flexible container and a second flexible container respectively, each with a volume capacity up to about 1000 mL.

In some embodiments, the system comprises a heating and/or a cooling unit configured to adjust or set a temperature of the first treatment chamber, wherein the method further comprises: controlling the heating/cooling unit to maintain the temperature of the first biological fluid within 2° C. during treatment of the first biological fluid by illumination from the first array of light sources. In some embodiments, the method further comprises: controlling the system to maintain the temperature of the first biological fluid within 2° C. during treatment of the first biological fluid by illumination from the first array of light sources. In some embodiments, the system comprises a heating and/or a cooling unit configured to adjust or set a temperature of the second treatment chamber, wherein the method further comprises: controlling the heating/cooling unit to maintain the temperature of the second biological fluid within 2° C. during treatment of the second biological fluid by illumination from the second array of light sources. In some embodiments, the method further comprises: controlling the system to maintain the temperature of the second biological fluid within 2° C. during treatment of the second biological fluid by illumination from the second array of light sources.

In some embodiments, the housing has a maximum horizontal width within a range of 30-45 cm. In some embodiments, the system is configured to operate within a target operating space such that there are empty spaces of 20 cm or less on both left and right sides of the housing.

In some embodiments, the system further comprises one or more access panels configured to provide access to one or more of the first array of light sources, the second array of light sources, and/or the one or more processors. In some embodiments, the system further comprises one or more front access panels configured to provide access to one or more of the first array of light sources, the second array of light sources, and/or the one or more processors. In some embodiments, the system further comprises one or more side access panels configured to provide access to one or more of the first array of light sources, the second array of light sources, and/or the one or more processors.

In another aspect, the present disclosure provides a method of treating a biological fluid, comprising illuminating the biological fluid with any of the systems provided herein (e.g., aforementioned systems, systems disclosed hereafter), for a duration and at an intensity sufficient to inactivate a pathogen in the biological fluid (e.g., if present in the biological fluid). In some embodiments, the present disclosure provides a method of treating a biological fluid comprising: providing the biological fluid in admixture with a pathogen inactivation compound (e.g., photoactive pathogen inactivation compound, psoralen, amotosalen), and illuminating the biological fluid with any of the systems provided herein (e.g., aforementioned systems), for a duration and at an intensity sufficient to inactivate a pathogen in the biological fluid (e.g., if present in the biological fluid). In some embodiments, the biological fluid is illuminated with ultraviolet light (e.g., ultraviolet A, ultraviolet B, ultraviolet C, ultraviolet light with a first peak wavelength of from about 315 nm to about 350 nm) emitted by a set of one or more first light sources, wherein: 1) each of the one or more first light sources emits light having a full-width half-maximum (FWHM) spectral bandwidth of less than 20 nanometers, and/or 2) each of the one or more first light sources is a light-emitting diode (LED). In some embodiments, the biological fluid is illuminated with ultraviolet light emitted by a set of one or more first light sources with a first peak wavelength of from about 315 nm to about 350 nm. In some embodiments, the biological fluid is illuminated with ultraviolet light emitted by a set of one or more first light sources with a first peak wavelength from about 330 nm to about 350 nm. In some embodiments, the biological fluid is illuminated with ultraviolet light emitted by a set of one or more first light sources with a first peak wavelength of from about 340 nm to about 350 nm. In some embodiments, the biological fluid is illuminated with ultraviolet light emitted by a set of one or more first light sources with a first peak wavelength within a range of 345±5 nm. In some embodiments, the biological fluid is illuminated with ultraviolet light emitted by a set of one or more first light sources with a first peak wavelength of from about 315 nm to about 335 nm. In some embodiments, the biological fluid is illuminated with ultraviolet light emitted by a set of one or more first light sources with a first peak wavelength and ultraviolet light from a set of one or more second light sources with a second peak wavelength, wherein the second peak wavelength differs from the first peak wavelength by at least 5 nanometers. In some embodiments, the duration and intensity of illuminating provides a total dose of ultraviolet light illuminating the biological fluid of about 0.5 J/cm$^2$ or more (e.g., about 0.5 J/cm$^2$ to about 50 J/cm$^2$). In some embodiments, the intensity is between 1 and 1000 mW/cm$^2$ (e.g., between 1 and 100 mW/cm$^2$). In some embodiments, the duration is between 1 second and 2 hours (e.g., between 1 minute and 60 minutes). In some embodiments, the method of treating a biological fluid is sufficient to inactivate at least 1 log of a pathogen in the biological fluid. In some embodiments, the method of treating a biological fluid is sufficient to inactivate at least 4 logs of a pathogen in the biological fluid. In some embodiments, the biological fluid is a blood product (e.g., platelets, plasma).

DETAILED DESCRIPTION

The following description is presented to enable a person of ordinary skill in the art to make and use the various embodiments. Descriptions of specific systems, devices, methods, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

Disclosed herein are systems, methods, and apparatuses for treating biological fluids. In some embodiments, the biological fluid treatment system includes a treatment chamber configured to receive biological fluids, a platform configured to carry the biological fluid to be positioned in the treatment chamber, an array of light sources positioned to illuminate the biological fluid in the treatment chamber, and a display configured for displaying a graphical user interface (GUI). In some embodiments, the biological fluid treatment system includes a scanner configured to obtain identifying information associated with a first biological fluid, a second biological fluid, or both the first biological fluid and the second biological fluid.

Biological fluids, such as for example blood and blood products, may contain contaminating pathogens due to an infected donor, or introduction of pathogens during processing. As such, it may be desirable to subject such biological fluids to a treatment process (e.g., pathogen inactivation, pathogen reduction) that reduces the risk of contaminating pathogens. Ideally, such a process results in the inactivation of a broad range of pathogens (e.g., viruses, bacteria, parasites) that may be present in the biological fluid. The treatment process may also inactivate other undesirable substances, such as for example cells (e.g., leukocytes) and nucleic acids that may be present in the biological fluid. Advantageously, the present disclosure provides improved systems, methods and apparatuses for treating biological fluids, including mixtures of biological fluids and photochemical agents, with light.

Figure 1:
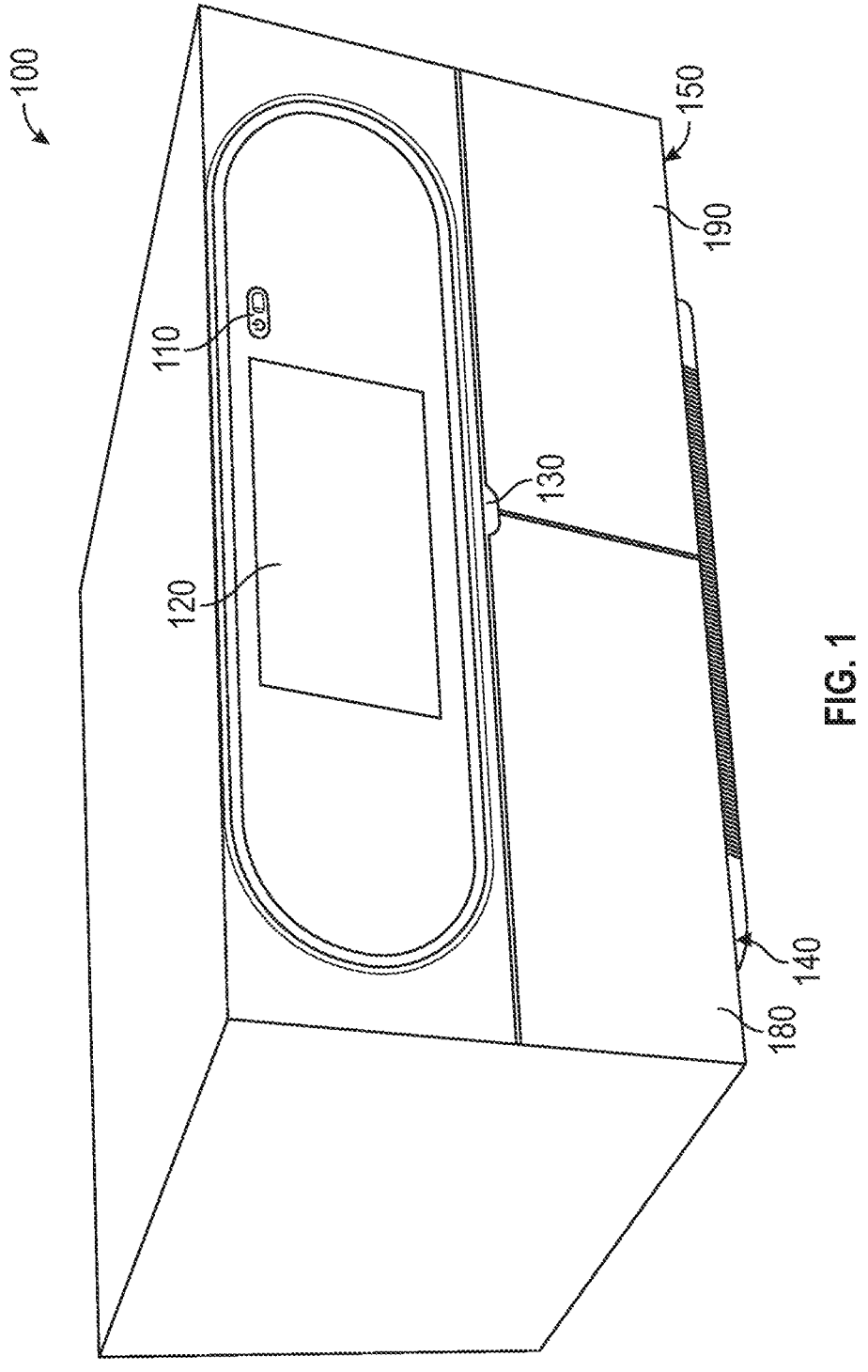
FIG. 1 illustrates an exemplary system for treating biological fluids.

FIG. 1 illustrates an exemplary system 100 for treating biological fluids. As used herein, a "biological fluid" refers to any fluid that is found in or derived from an organism (e.g., human, animal, plant, microorganism), or that comprises one or more components (e.g., biologics) found in, isolated from, or derived from an organism, including synthetic (e.g., recombinant) versions thereof. Biological fluids may include, but are not limited to, blood and blood products, vaccines, cells (e.g., primary cells, cell lines, cell cultures), natural and recombinant peptides or proteins (e.g., therapeutics, antibodies), bacterial cultures, virus suspensions and the like. As used herein, "blood product" refers to blood (e.g., whole blood) or a component or derivative of blood such as, for example, red blood cells, white blood cells, platelets, plasma or components thereof (e.g., coagulation factors, albumin, fibrinogen), cryoprecipitate and cryo-poor (e.g., cryo-reduced) plasma, or a combination of one or more of such components that have been separated from blood. In some embodiments, a biological fluid may further comprise a non-biological fluid, such as for example, a physiological solution (e.g., diluent solution), including but not limited to saline, buffered solution, nutrient solution, platelet additive solution (PAS) and/or anticoagulant solution. In some embodiments, when the biological fluid is positioned (e.g., the biological fluid is in a container such as treatment bag positioned on a platform) in a chamber of the biological fluid treatment system, the biological fluid is illuminated by light (e.g., visible light, ultraviolet light) having a certain spectral profile at specified intensities for a determined time period.

System 100 includes a power switch 110, display 120, scanner 130, platform 140, and platform 150. Although system 100 in FIG. 1 includes the described elements, examples of system 100 can include different combinations of the described elements or additional elements without departing from the scope of the disclosure. In some examples, the system 100 can couple, via a wired or a wireless connection, to a computing device (e.g., computer, mobile device) (not shown).

In some embodiments, in response to an input to the power switch 110, power is provided to the system 100. For example, the power switch 110 can be a mechanical button. When the system 100 is off, in response to a push of the power switch 110, power is provided to the system 100 (e.g., the system 100 turns on). When the system 100 is on, in response to a push of the power switch 110, the provided power to the system 100 ceases (e.g., the system 100 turns off). In some examples, during treatment, the system 100 stays on and does not turn off in response to a push of the power switch.

As another example, the power switch 110 can be a capacitive switch that can be activated with a touch input (e.g., by placing a user's finger on the power switch). As yet another example, the power switch can be a button having two or more states. The power switch can be at an "off" state when the power switch is at a first position (e.g., unpressed, flipped to a first side). The power switch can be at an "on" state when the power switch is at a second position (e.g., pressed, flipped to a second side).

In some embodiments, the display 120 is a touchscreen. For example, the display 120 can be a capacitive touchscreen or a resistive touchscreen. In some examples, the display 120 is configured to display a graphical user interface (GUI) for operating the system 100. In some embodiments, the display 120 is configured to receive input from the scanner 130. In some embodiments, the display 120 is configured to receive input on the GUI. For example, a GUI object of a plurality of GUI objects displayed on the GUI can be selected by providing a user's manual input (e.g., touch input or hover input) on the touchscreen. In response to receiving the input, the system 100 can perform an operation associated with the selected GUI object. For example, a GUI object may be associated with initiation of a biological fluid treatment, and in response to receiving an input selecting the GUI object, the system 100 initiates a process to treat a biological fluid. In some embodiments, the display 120 is configured to display instructions to a user operator (e.g., operator instructions) on the GUI. In some embodiments, the display 120 is configured to display input from the scanner 130 to a user operator. In some embodiments, the display 120 is configured to display input from sound that is detected by an audio input (e.g., one or more microphones) and processed (e.g., speech-to-text conversion) by one or more processors into a visual form (e.g., command text, command code) on the display 120 that the user can recognize as an input command, such as for example a user's voice command that is detected by one or more microphones (e.g., located in any arrangement internal to, external to, and/or part of the exterior housing of the system 100) and converted by one or more processors into command text on the display 120 that the user can recognize as an input command. In some embodiments, the display 120 is configured to display input from a user's visual motion (e.g., hand motion or gesture, object in a swiping motion) that is detected by a motion sensor (e.g., one or more cameras) and processed (e.g., motion-to-text conversion, motion-to-graphic conversion) by one or more processors into a visual form (command text, command code, command icon, command graphic) on the display 120 that the user can recognize as an input command, such as for example a user's hand gesture (e.g., hand in a swiping motion) that is detected by one or more cameras (e.g., located in any arrangement internal to, external to, and/or part of the exterior housing of the system 100) and converted by one or more processors into visual command text or a visual graphic on the display 120 that the user can recognize as an input command. Although one display 120 is illustrated in FIG. 1, the system 100 can include more than one display in some examples.

By using a touchscreen as an input component and/or input from the scanner 130, the user interface of system 100 can be simplified. For example, the use of a touchscreen can reduce the need for physical buttons corresponding to features that can be similarly performed using the touch screen. Biological fluid treatment using system 100 can be more efficient using the simplified user interface.

Although the power switch 110 and display 120 are described as elements of the system 100 that can be configured to receive user input, other elements or means of input can be included in the system 100 without departing from the scope of the disclosure. For example, the system 100 can include directional input keys, a mouse pad, or a scroll wheel configured for navigating a GUI displayed on the display 120. In some embodiments, the system 100 is configured to receive a user's input from sound that is detected by an audio input (e.g., one or more microphones) and processed (e.g., speech-to-text conversion) by one or more processors into a language form (e.g., command text, command code) that the system 100 can recognize as an input command, such as for example a user's voice command that is detected by one or more microphones (e.g., located in any arrangement internal to, external to, and/or part of the exterior housing of the system 100) and converted into command text by one or more processors that the system 100 can recognize as an input command. In some embodiments, the system 100 is configured to receive input from a user's visual motion (e.g., hand motion or gesture, object in a swiping motion) that is detected by a motion sensor (e.g., one or more cameras) and processed (e.g., motion-to-text conversion) by one or more processors into a language form (e.g., command text, command code), such as for example a user's hand gesture (e.g., hand in a swiping motion) that is detected by one or more cameras (e.g., located in any arrangement internal to, external to, and/or part of the exterior housing of the system 100) and converted into command text by one or more processors that the system 100 can recognize as an input command. Alternatively or in addition, system 100 can be configured to receive input other than user input, such as for example, from one or more sensors implemented for system 100. Non-limiting examples of various sensors that may be implemented (e.g., in a treatment chamber) include one or more light sensors configured to measure the light intensity at various portions of the treatment chamber and/or the light intensity incident on various portions of one or more biological fluids, one or more air flow sensors, one or more heat sensors for measuring the temperature of treatment chamber and/or the temperature of one or more biological fluids, one or more sensors for detecting the presence and/or type of one or more biological fluids (e.g. pressure sensors, optical retro-reflective sensors, optical transmissive sensors, label readers, scanners, barcode scanners, RFID sensors, etc.), one or more sensors for detecting a property (e.g., transmissivity) of the biological fluid (e.g., optical sensors, spectroscopic sensors), one or more sensors for detecting a photochemical compound in the biological fluid (e.g., fluorescence spectrometry), and one or more sensors (e.g., ultrasonic sensors) positioned to detect the fluid depth of a portion (e.g., various portions) of one or more biological fluids.

In some embodiments, system 100 can be configured to receive input from one or more scanners implemented for system 100. In some embodiments, the scanner 130 is configured to obtain information relating to biological fluids. In some examples, the scanner 130 can be configured to obtain identifying information related to the biological fluids to be treated. For example, the biological fluid may be stored in a container (e.g., hemocompatible bag, treatment bag) (not shown), and the container or other containers in a multi-container assembly (e.g., disposable fluid processing set) can include a tag or label or designated area containing the identifying information in some form, such as a visible form (e.g., a barcode, a QR code, etc.) and/or transmittable form (e.g., electronic identifier, radio frequency identification (RFID)). In some embodiments, the identifying information can represent information about the biological fluid product, such as biological or other parameters (e.g., donation ID, product code, set code, lot number, type of biological fluid, volume of biological fluid, content of biological fluid, for example platelet number or concentration) and treatment parameters. In some embodiments, the biological or other parameters, optionally in combination with input from one or more sensors and/or user inputs may determine a treatment parameter. In some examples, multiple sets of identifying information can be obtained. For example, multiple sets of identifying information may be located on one or more respective containers associated with (e.g., containing or part of a multi-container assembly containing) the biological fluid, and the sets of identifying information can be obtained from the respective containers by scanner 130. In some embodiments, the scanner may be a multi-scan scanner (e.g., camera with multi-scan functionality, camera in cooperation with circuitry (e.g., hardware and/or software) having multi-scan processing functionality, handheld scanner with multi-scan functionality, handheld scanner in cooperation with circuitry (e.g., hardware and/or software) having multi-scan processing functionality, label reader with multi-scan functionality, label reader in cooperation with circuitry (e.g., hardware and/or software) having multi-scan processing functionality) configured to sequentially or substantially simultaneously capture (e.g., acquire) multiple sets of identifying information (e.g., multiple barcodes, multiple QR codes, multiple labels, optical character recognition (OCR) of different strings or arrangements of alphanumeric text and/or symbols, image recognition, etc.) located on one or more containers, such as for example capturing multiple sets of identifying information in "batch" mode (e.g., in response to a single user input or a single device input that commands, triggers, or otherwise initiates a multi-scan operation that acquires multiple sets of identifying information). A single multi-scan operation may capture, sequentially or substantially simultaneously (e.g., simultaneously), multiple sets of identifying information (e.g., in a single operation, a camera can capture one or more images of one or more labels that show the multiple parameters of a biological product, such as for example donation ID, product code, set code, lot number, type of biological fluid, volume of biological fluid, content of biological fluid; in a single operation, a multi-scanner can perform one or more scans of one or more labels that show the multiple parameters above). In some embodiments, the multi-scanner or the system 100 is configured to recognize (and/or convert into another form recognized by the multi-scanner or system 100) the captured multiple sets of identifying information (e.g., recognizing (and/or deciphering) barcodes, QR codes, alphanumeric text and/or symbols, images) captured in a multi-scan operation. After capturing multiple sets of identifying information (e.g., in captured image(s), performed scan(s)), a multi-scanner can convey or communicate them (e.g., via a wired or wireless connection) to the system 100 in recognized (and/or converted) form (e.g., in a language form that the system 100 can already recognize, for example as parameter data) or in unrecognized form (e.g., captured image(s), performed scan(s)). If in unrecognized form, the system 100 can process the captured multiple sets of identifying information into a recognized form. The system 100 can assign the multiple sets of identifying information to corresponding fields (e.g., auto-populating information fields) of the GUI of the display 120 when displaying the GUI for the treatment chamber associated with the biological fluid to be treated. Thus, a multi-scan operation may provide data entry of all or most parameter data for a biological fluid into multiple specific data fields via an auto-population technique that may be convenient, efficient, and time-saving. For example, with a multi-scan operation, a user need not perform multiple scans in any particular order to capture multiple sets of identifying information that may be presented in a certain order (e.g., no need to perform a scan for each label on a container in the visual order of specific data fields presented on the GUI to the user).

In some embodiments, the scanner 130 is integrated or embedded in a fixed position in the system 100 (e.g., in a housing of system 100). In some embodiments, the identifying information can enter a field of view of the scanner 130, and the scanner 130 can obtain the identifying information when the information is in the field of view. For example, a user can hold a biological fluid treatment container (e.g., bag) with a barcode facing the scanner 130, and the scanner 130 can image-capture, scan, or read the barcode; based on the obtained barcode, the system 100 can determine information about the biological fluid product. In some embodiments, the identifying information can enter a detection range of the scanner 130, and the scanner 130 can obtain the identifying information when the information is in the detection range. For example, a user can hold a biological fluid treatment bag with an RFID tag near the scanner 130, and the scanner 130 can detect the RFID tag; based on information obtained from the detected RFID tag, the system 100 can determine information about the biological fluid product.

Although the scanner 130 is illustrated as being located on an exterior of the system 100 in FIG. 1, the scanner 130 can be located at different locations of the system 100. In some embodiments, the scanner 130 is located inside the system 100. For example, the scanner 130 can be located at a top of a treatment chamber or at an opening of a treatment chamber of system 100. The scanner 130 can obtain information related to the biological fluid after the biological fluid is placed on a platform and/or in the chamber.

In some examples, the scanner 130 can be included in a device coupled to system 100. For example, the scanner 130 can be included in a handheld scanner (e.g., barcode scanner, QR code scanner) coupled to system 100. In some examples, a handheld scanner couples to system 100 via a wired connection. In some examples, a handheld scanner couples to system 100 via a wireless connection.

Although one scanner 130 is illustrated in FIG. 1, system 100 can include more than one scanner 130. For example, system 100 can include a plurality of treatment chambers, and each treatment chamber may have a corresponding scanner (e.g., internal scanner). As another example, system 100 can include a plurality of platforms and each platform may have a corresponding scanner (e.g., external scanner) located near or at an opening for a respective platform. As the platform moves through the opening, a container (e.g., treatment bag) containing the biological fluid can traverse a field of view of a respective scanner, and information, associated with the biological fluid, in visible form on the container or an associated container of a multi-container assembly can be obtained by the respective scanner.

In some embodiments, the platform 140 (e.g., tray, well, plate, stage) is configured to carry the biological fluid (e.g., in a container containing the biological fluid) during treatment. In some embodiments, the platform is moveable (e.g., slideably moveable, configured to translate from inside the treatment chamber to outside the treatment chamber) between the interior and exterior of the treatment chamber (e.g., partially out of the treatment chamber). In some embodiments, the system 100 further comprises a first panel 180 movable between a closed position and an open position, wherein the first panel 180 covers a first opening to the first treatment chamber in the closed position, wherein the first panel 180 uncovers the first opening to the first treatment chamber in the open position. In some embodiments, the first panel can have a handle (e.g., a protruding handle, a recessed handle). The handle can allow the user to manually open or close the first panel to load or unload the biological fluid into or from the chamber. In some examples, an exterior of the first panel can include an opening or a notch that acts as a recessed handle. In some examples, a handle can be attached to an exterior of the first panel. In some embodiments, the first panel is attached to, integrated with, or formed together with the platform 140 (e.g., in a drawer configuration). In some embodiments, the first panel 180 is a separate structure from the platform 140 (e.g., a separate hinged door that covers and uncovers the first opening to the first treatment chamber), and the platform 140 can slide in and out of the first treatment chamber separately from the first panel 180.

In some examples, the platform and/or first panel can be locked to remain in the closed position during treatment. The system 100 can prevent a user from prematurely accessing the content of the platform 140 (e.g., accessing the first treatment chamber) during treatment by locking the first panel to remain in the closed position. In some embodiments, the first panel can be locked by a pin (e.g., solenoid and pin) or magnetic lock mechanism. The system 100 can permit a user to access, by unlocking the first panel, the content of the platform 140 before and after treatment (e.g., to load the biological fluid on the platform 140, to unload the biological fluid from the platform 140) or after an input (e.g., an input on the GUI, an input to open latch, an input to a button switch).

In some embodiments, an exterior of the first panel is substantially smooth, such that the surface of the exterior is continuous. For example, a surface of the first panel on an exterior (e.g., exterior housing) of system 100 may be flat. As another example, a surface of the first panel on an exterior of system 100 may be continuously smooth; that is, the surface of the first panel on an exterior of the system 100 lacks any opening, notch, gap, or the like, or any opening, notch, gap or the like is sufficiently small so as to prevent a user from pulling on the first panel with fingers. Such sufficiently small openings, notches, gaps or the like may provide air venting in the first panel. As yet another example, the entire exterior (e.g., surface) of the first panel lacks any handle, protruding member, or the like. As a further example, the edges of the first panel, when in a closed position, may be flush or substantially flush with adjacent structures (e.g., adjacent panel(s), adjacent frame of exterior housing, etc.) where, between the edges of the first panel and adjacent structure(s), any opening, notch, gap or the like is sufficiently small so as to prevent a user from pulling on the first panel with a finger(s) (e.g., preventing a friction pull on the side of an edge of the first panel, preventing a hooking pull on the rear side of an edge of the first panel), as illustrated in FIG. 1. In some embodiments, the continuous surface of the exterior prevents a user from prematurely opening the first panel by manual handling (e.g., at a time when the biological fluid is being treated) or from inadvertently damaging the system by forcefully pulling a handle. If the first panel is prematurely opened, the biological fluid being treated may be damaged, or the biological fluid may not be adequately treated. If a user forcefully pulls a handle of a locked first panel, the handle may be damaged, the movement mechanism (e.g., tracks, rails) may be damaged or the lock may be damaged.

As illustrated in FIG. 1, the structure of the platform 150 symmetrically mirrors structure of the platform 140 about a vertical axis. In some embodiments, the platform 150 is substantially similar to platform 140 in size, shape, or orientation. As illustrated, the platforms 140 and 150 are arranged horizontally, such that the first biological fluid and the second biological fluid, when positioned on the first platform and on the second platform, respectively, are within a same plane. As the first panel 180 may be associated with the platform 140, as discussed above, a second panel 190 may be associated with the platform 150. The above teachings for the first panel 180 may also apply to the second panel 190.

Although two platforms are illustrated in FIG. 1 as being a part of system 100, the system 100 can include one platform or more than two platforms that are substantially similar to platform 140 or platform 150 without departing from the scope of the disclosure. In general, the number of illustrated platforms and treatment chambers associated with systems 100-700 are exemplary; embodiments of systems 100-700 may include different numbers and combinations of platforms, treatment chambers, and their associated elements (e.g., scanners, light arrays, compartments) without departing from the scope of the disclosure. For example, in some embodiments, a system can include only one chamber with only one platform. In some embodiments, a system can include only one chamber with two or more platforms. In some embodiments, a system can include two chambers, each with only one platform. In some embodiments, a system can include two chambers, each with two or more platforms.

In some embodiments, the platform comprises a first compartment and a second compartment separate from the first compartment. In some embodiments, the first compartment is configured to carry a container (e.g., container of a multi-container assembly) containing a biological fluid in a position for illumination. In some embodiments, the second compartment is configured to carry a container (e.g., container of a multi-container assembly) not containing a biological fluid in a position not for illumination. In some embodiments, the platform is configured to separately carry at least a first container with a first biological fluid and a second container with a second biological fluid. In some embodiments, the platform is transparent (e.g., substantially transparent, >95% transparent, >90% transparent, >80% transparent, >80% transparent) to light with a wavelength within 100 nm (e.g., 75 nm, 50 nm, 40 nm, 30 nm, 20 nm) of the peak wavelength of light used for illumination. In some embodiments, the platform is transparent (e.g., substantially transparent, >95% transparent, >90% transparent, >80% transparent, >80% transparent) to ultraviolet light (e.g., UV-A, UV-B, and/or UV-C).

Figure 2A:
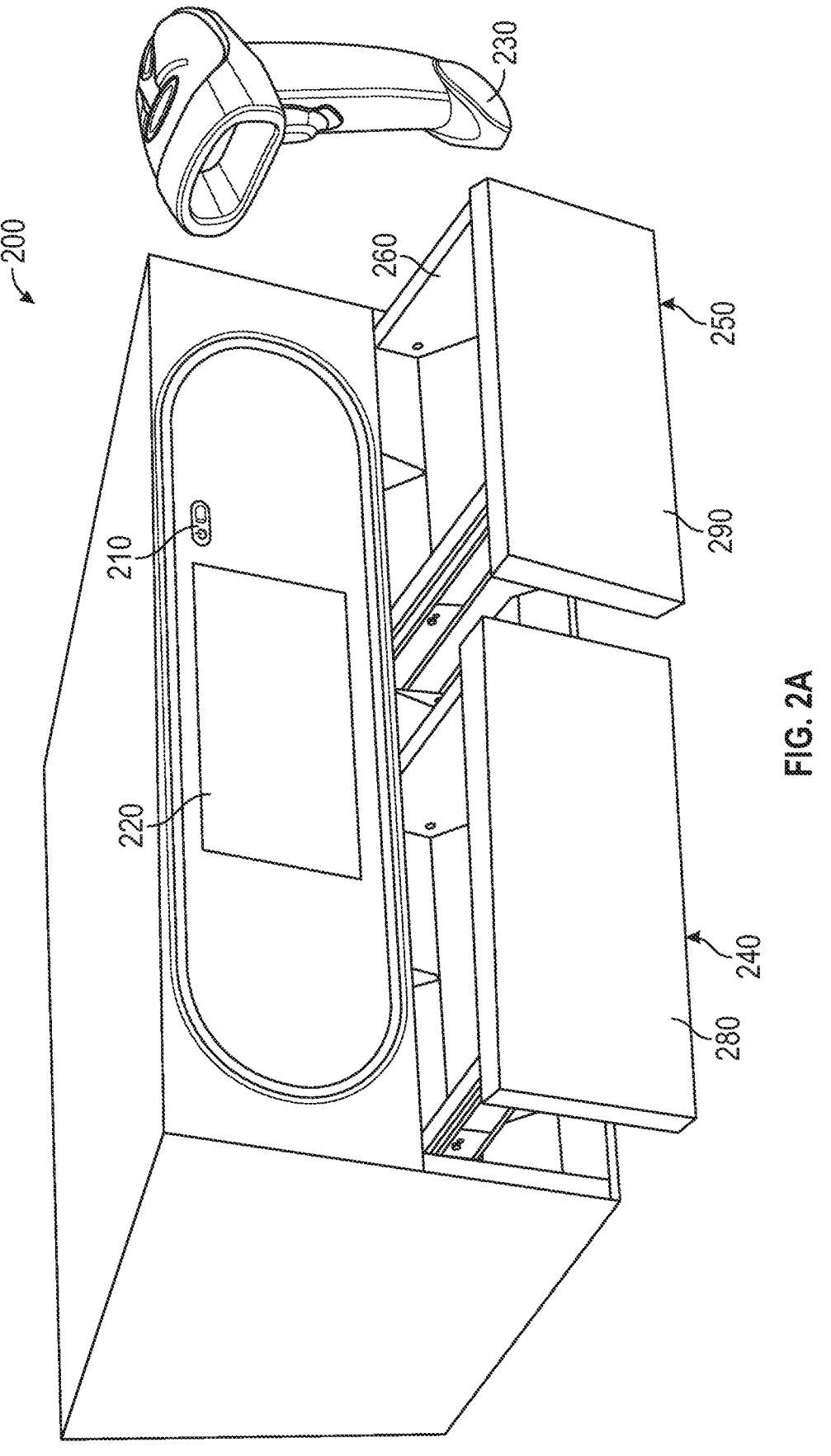
FIGS. 2A-2C illustrate exemplary systems for treating biological fluids.

FIG. 2A illustrates an exemplary system 200 for treating biological fluids. In some embodiments, the system 200 is substantially similar to system 100, as illustrated in FIG. 1. Power switch 210 can correspond to power switch 110. Display 220 can correspond to display 120. Platforms 240 and 250 can respectively correspond to platforms 140 and 150. Panels 280 and 290 can respectively correspond to panels 180 and 190.

In some embodiments, the system 200 includes an external scanner 230. In some embodiments, the external scanner 230 is in addition to a scanner integrated or embedded in a fixed position in the system 200. As illustrated, the external scanner 230 is external to a housing that houses the other elements and can be operatively coupled to a processor of the system 200. In some embodiments, the external scanner 230 is a handheld scanner. Although the external scanner 230 is illustrated with a wireless connection in FIG. 2A, the external scanner 230 can be operatively coupled using a wired connection.

As illustrated in FIG. 2A, platforms 240 and 250 are in drawer configurations at an open position, in contrast with platforms 140 and 150 being at a closed position in FIG. 1. Although both platforms 240 and 250 are illustrated as in drawer configurations being open in FIG. 2A, one platform in a drawer configuration can also open at a time (e.g., with the other remaining closed).

In some embodiments, a first panel 280 and a second panel 290, associated with the platforms 240 and 250, lack any handles. In some embodiments, at a closed position, a panel can be opened by applying a force opposite to the opening direction (e.g., pushing an exterior of a panel to engage a push latch that releases the panel to open). In some embodiments, at a closed position, a panel can be opened using mechanical components (e.g., motors, servos) to actuate the panel (e.g., as a hinged door, as part of the platform in a drawer configuration). In some embodiments, the system can permit a user to access the content of a platform by opening the panel (e.g., by a spring mechanism), to allow the user to further manually slide out the platform. For example, in accordance with a determination that a treatment procedure is starting or complete, the system can mechanically open one or more panels corresponding to the treatment for loading or unloading one or more biological fluid containers (e.g., treatment bags).

In some embodiments, the platforms include a compartment 260 substantially similar to the compartments described herein. Although FIG. 2A illustrates a platform as having one compartment visible (e.g., for a platform in a drawer configuration at an open position), each of the platforms in system 200 can include any number of compartments without departing from the scope of the application.

Figure 2B:
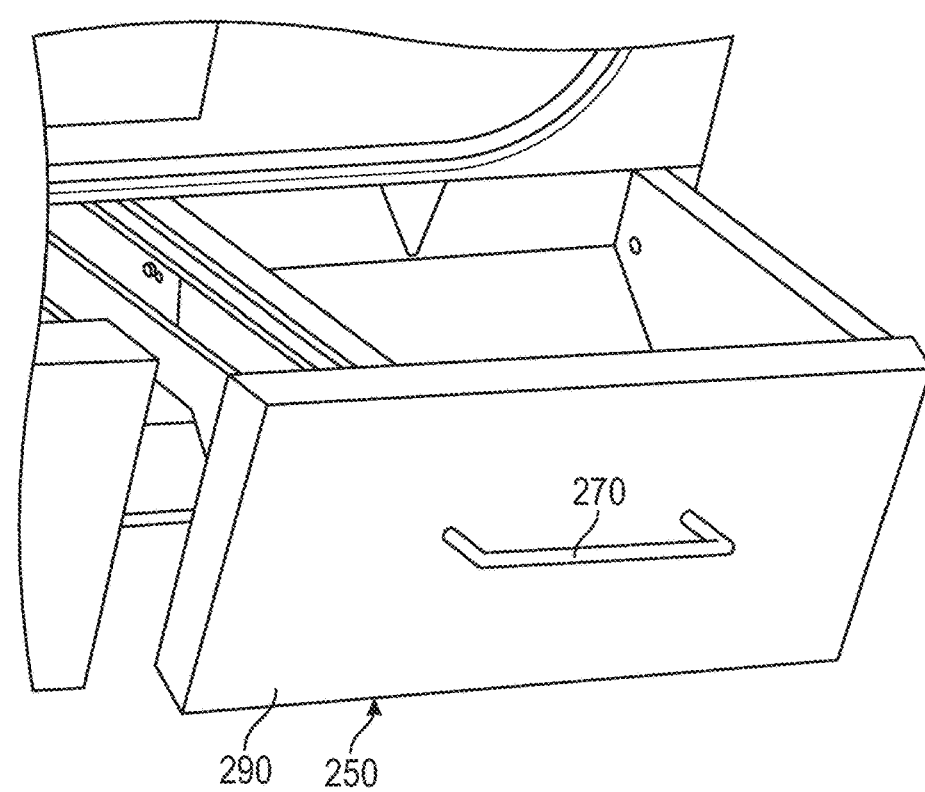
Figure 2C:
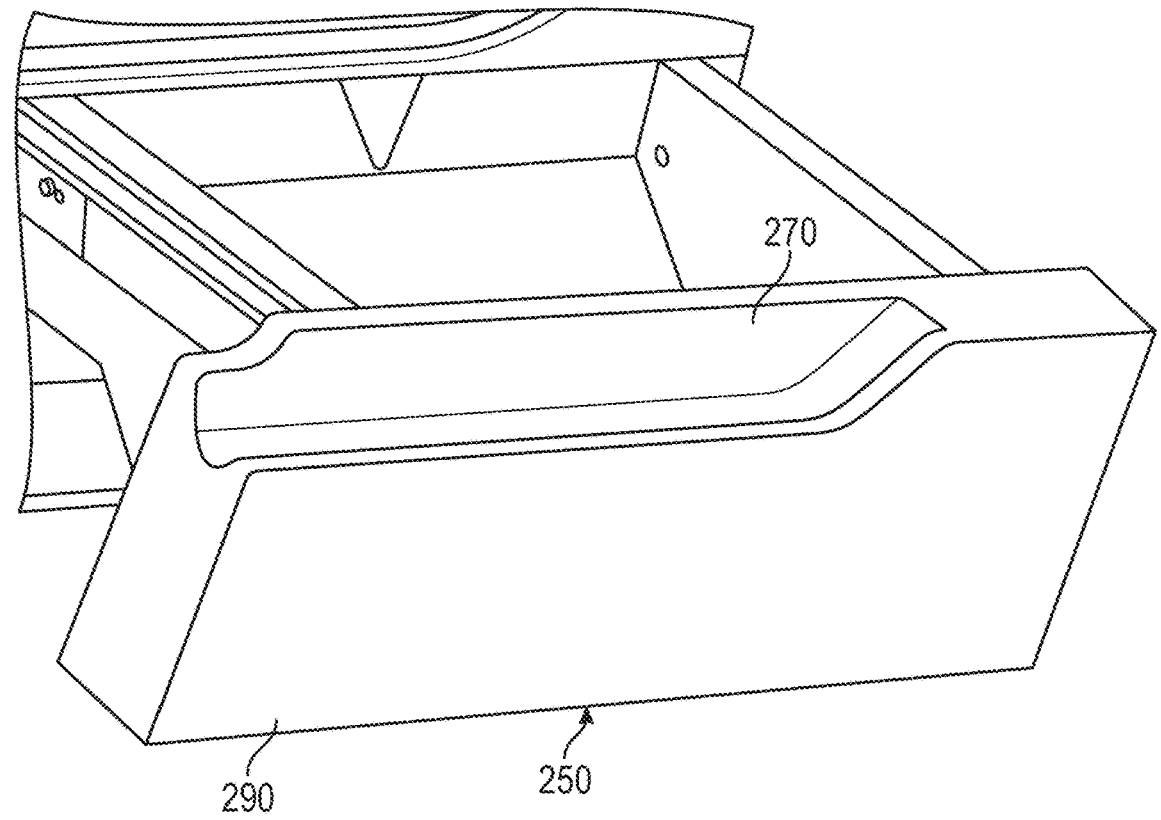

In some embodiments, the panels can include a handle. FIG. 2B illustrates the panel, associated with platform 250, as having a protruding handle 270 physically coupled to the panel. FIG. 2C illustrates the panel, associated with platform 250, as having a recessed handle 270 that is part of the panel. In some embodiments, without or without a handle, a panel can be flush or substantially flush with adjacent structures (e.g., adjacent panel(s), adjacent frame of exterior housing, etc.), as illustrated in FIGS. 2A-2C.

Figure 3A:
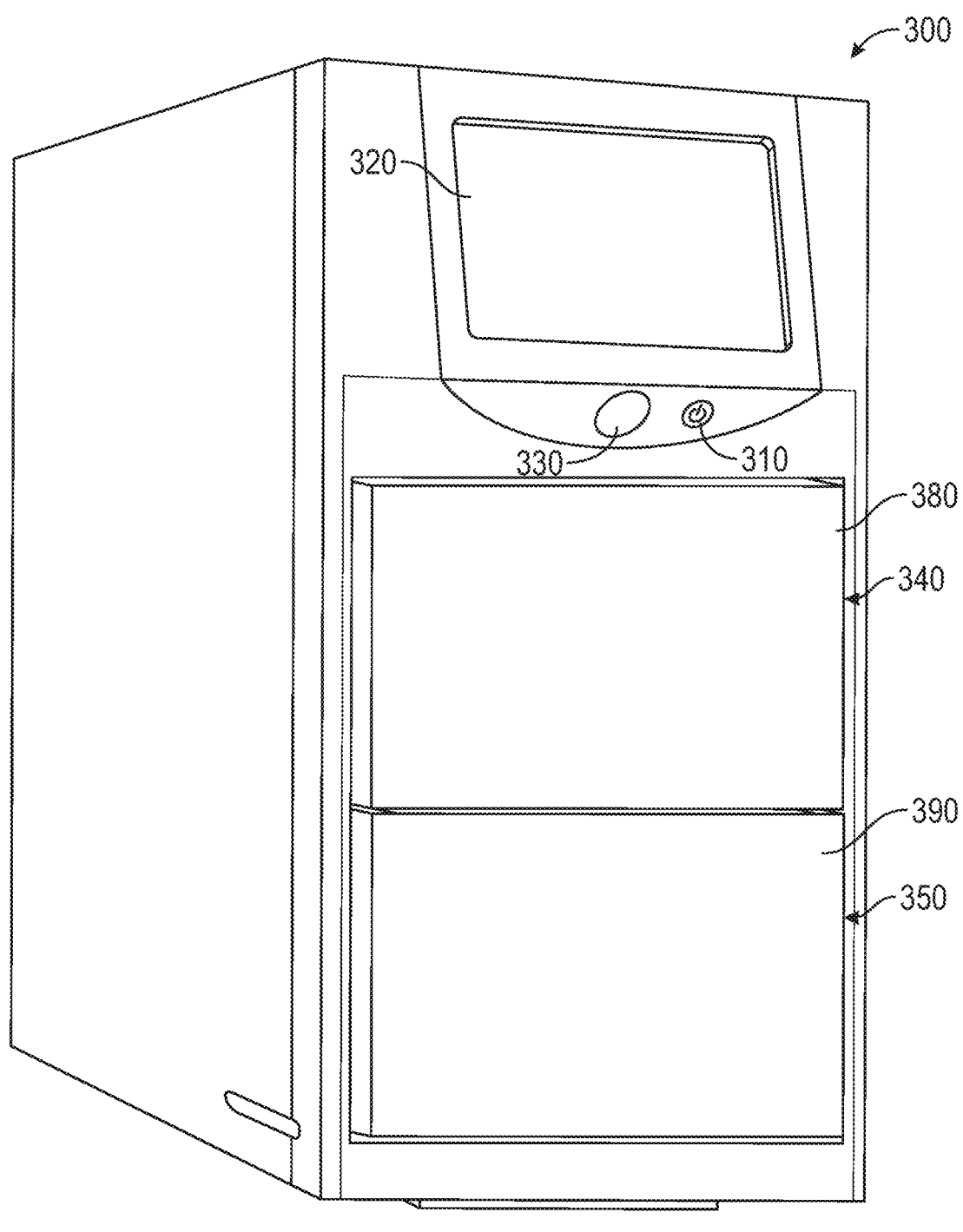
FIGS. 3A-3B illustrates exemplary systems for treating biological fluids.

FIG. 3A illustrates an exemplary system 300 for treating biological fluids. In some embodiments, the system 300 is substantially similar to system 100, with a difference that the treatment chambers and platforms are arranged vertically. Power switch 310 can correspond to power switch 110. Display 320 can correspond to display 120. Scanner 330 can correspond to scanner 130. In contrast to system 100, in which the platforms 140 and 150 are arranged horizontally, platforms 340 and 350 are arranged vertically such that the first biological fluid and the second biological fluid, when positioned on the first platform and on the second platform, respectively, are in parallel planes. Also in contrast to system 300, in which panels 180 and 190 are arranged horizontally, panels 380 and 390 are arranged vertically.

Figure 3B:
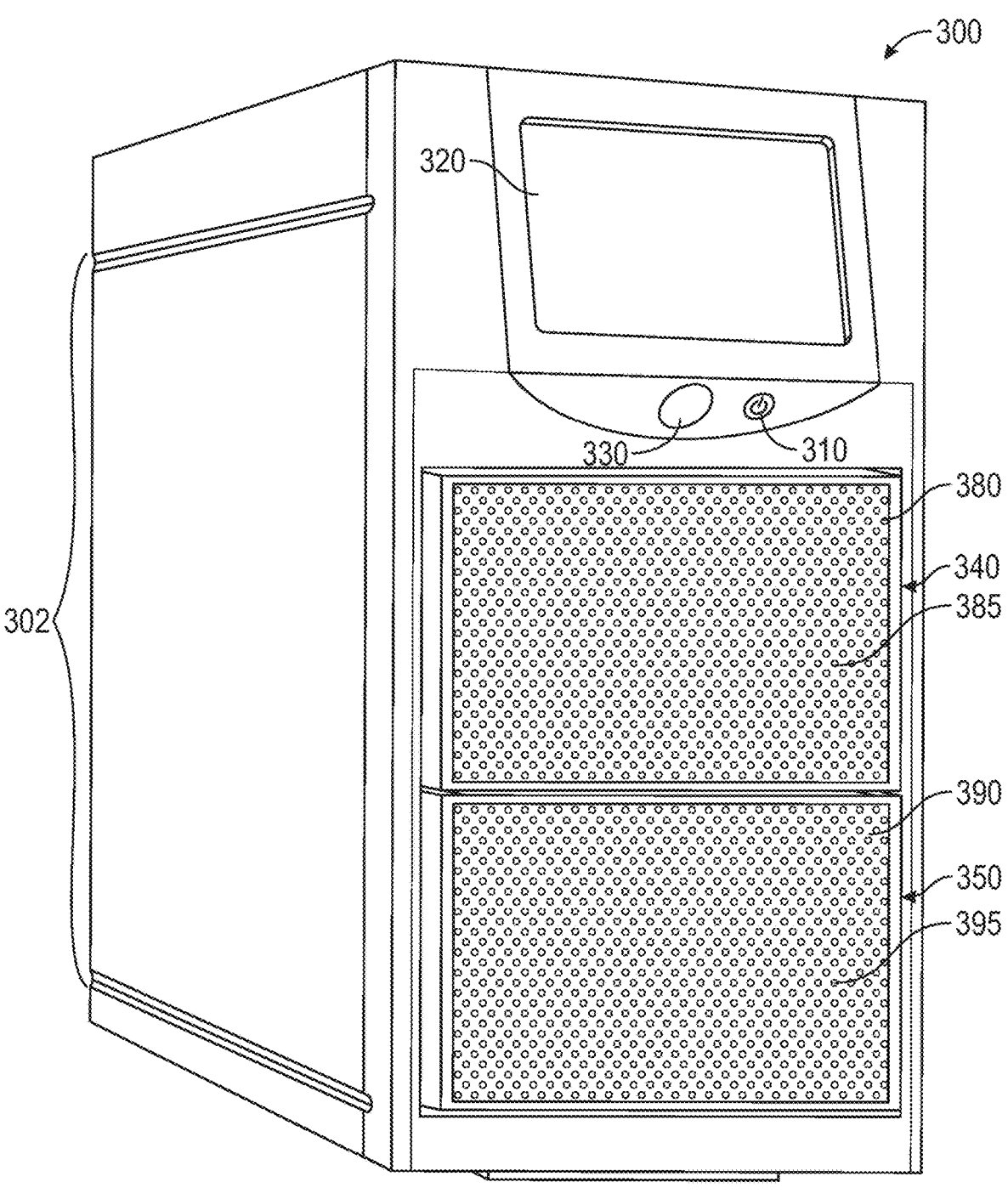

In some embodiments, system 300 can include air venting. FIG. 3B illustrates panels 380 and 390 with air venting 385 and 395, respectively. This air venting 385 and 395 can provide one or more air inlets (e.g., air intakes) through which air can be drawn into system 300, e.g., to provide cooling or heat dissipation or other temperature control functionality. This air venting 385 and 395 can provide one or more air outlets through which air can be expelled out of system 300, e.g., to provide cooling or heat dissipation or other temperature control functionality. Air can be drawn into system 300 and/or expelled out of system 300 by, e.g., the operation of one or more fans inside system 300. This air venting 385 and 395 are shown as, but not limited to, vent holes (e.g., circular vent holes), and can be embodied as any variation or combination of variations, e.g., horizontal vents, vertical vents, gratings, oval vent holes, rectangular or square vent holes, polygon vent holes, or any combinations thereof, etc. This air venting 385 and 395 are shown as, but not limited to, occupying most of the panels' areas, and can be embodied as any variation or combination of variations, e.g., occupying all of a panel's area, occupying a fraction of a panel's area, distinct horizontal venting strips, distinct vertical venting strips, circular or oval venting strips, rectangular or square venting strips, polygon venting strips, or any combinations thereof, etc. This air venting 385 and 395 are not limited to the location of panels, but may be located in other locations (e.g., alternatively or in addition to the panels), such as for example as part of the housing, at or near the front of the housing (e.g., above, below, or adjacent to the panels). In some embodiments, without or without air venting, a panel can be flush or substantially flush with adjacent structures (e.g., adjacent panel(s), adjacent frame of exterior housing, etc.), as illustrated in FIGS. 3A-3B.

In some embodiments, system 300 may include one or more access panels (e.g., front access panel, side access panel, top access panel) through which maintenance or service personnel may access and then perform maintenance or service on internal components or structure of system 300. FIG. 3B illustrates an exemplary side access panel 302 of system 300, located on the side of the exterior housing. Side access panel 302 may be opened in any manner, e.g., vertical hinge (e.g., located at rear vertical edge of side access panel 302), horizontal hinge (e.g., located at top or bottom of side access panel ##), fasteners (e.g., screws holding side access panel in place), etc. Side access panel 302 is shown as, but not limited to, encompassing the area between the two horizontal lines shown in FIG. 3B, and may embodied as any variation or combination of variations, e.g., encompassing an entire side of the exterior housing, encompassing a portion of the side of the exterior housing, encompassing multiple side access panels (e.g., one for each treatment chamber), etc.

Figure 4A:
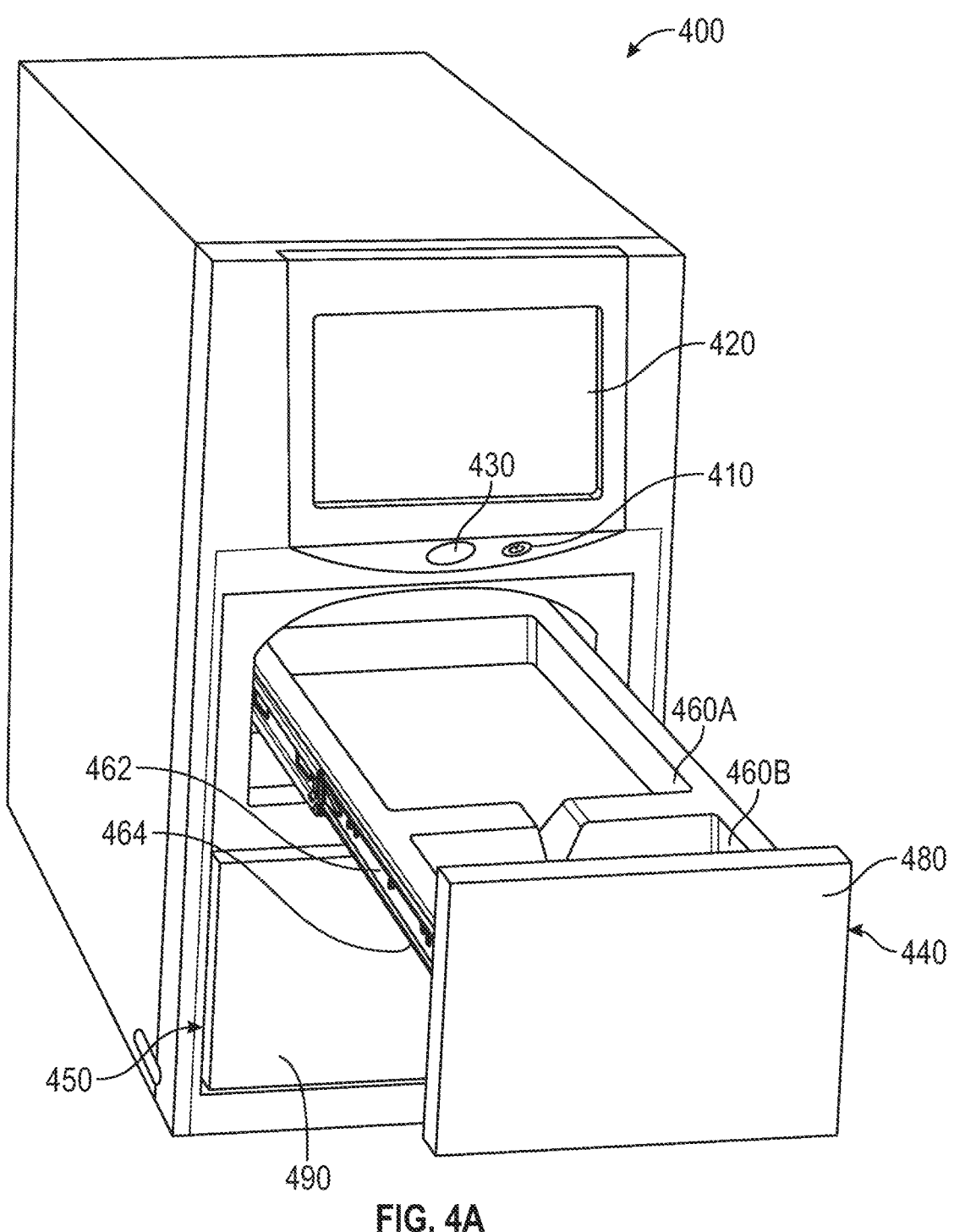
FIGS. 4A-4L illustrate exemplary systems for treating biological fluids.

FIG. 4A illustrates an exemplary system 400 for treating biological fluids. In some embodiments, the system 400 is substantially similar to system 300, as illustrated in FIG. 3. Power switch 410 can correspond to power switch 310. Display 420 can correspond to display 320. Scanner 430 can correspond to scanner 330. Platforms 440 and 450 can respectively correspond to platforms 340 and 350. Panels 480 and 490 can respectively correspond to panels 380 and 390.

As illustrated, platform 440 is in a drawer configuration at an open position in FIG. 4A, in contrast with platform 340 being at a closed position in FIG. 3. Although one platform is illustrated as in a drawer configuration being open in FIG. 4A, both platforms in drawer configurations can open at a same time.

In some embodiments, a first panel 480 and a second panel 490, associated with the platforms 440 and 450, lack any handles. In some embodiments, at a closed position, a panel can be opened by applying a force opposite to the opening direction (e.g., pushing an exterior of the panel to engage a push latch that releases the panel to open). In some embodiments, at a closed position, a panel can be opened using mechanical components (e.g., motors, servos) to actuate the panel (e.g., as a hinged door, as part of the platform in a drawer configuration). In some embodiments, the system can permit a user to access the content of a platform by opening the panel (e.g., by a spring mechanism), to allow the user to further manually slide out the platform. For example, in accordance with a determination that a treatment procedure is starting or complete, the system can mechanically open one or more panels corresponding to the treatment for loading or unloading one or more biological fluid containers (e.g., treatment bags).

In some embodiments, the platforms include compartments 460A and 460B substantially similar to the compartments described herein. Although FIG. 4A illustrates a platform as having two compartments, each of the platforms in system 400 can include any number of compartments without departing from the scope of the application.

Figure 4B:
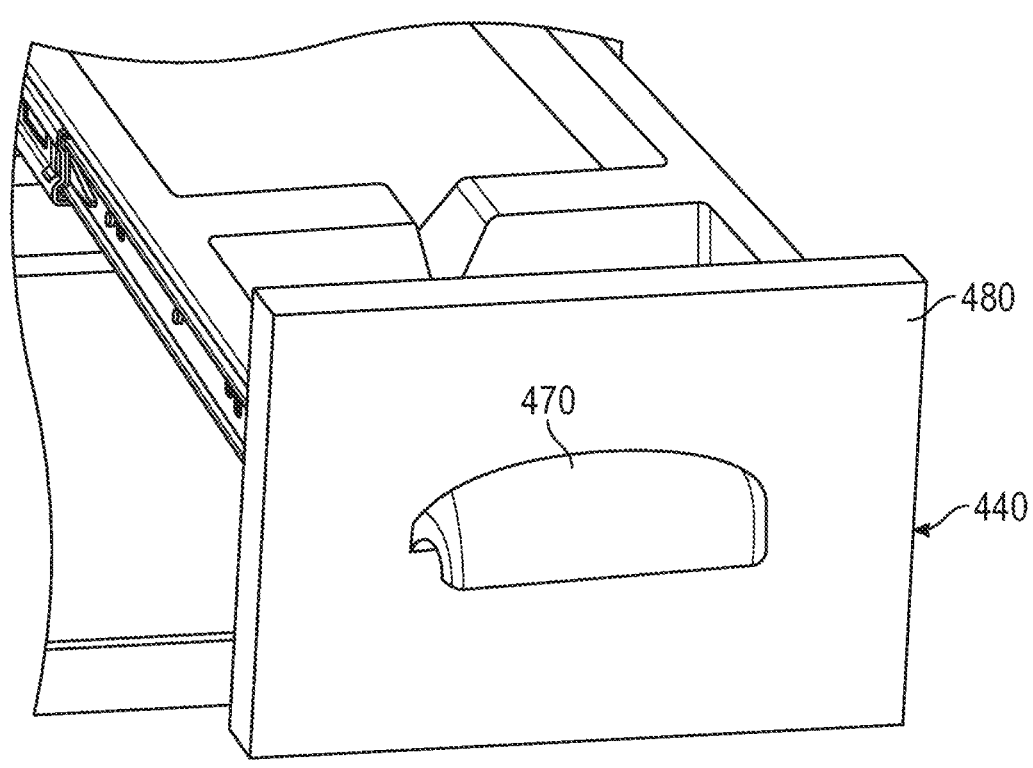
Figure 4C:
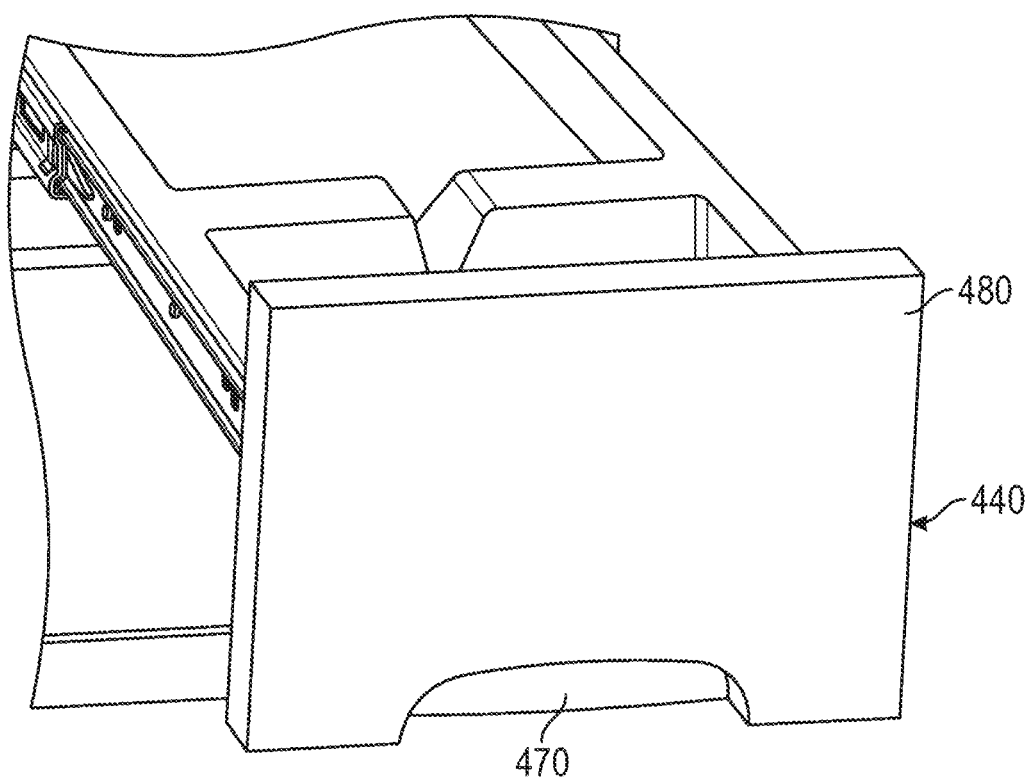

In some embodiments, the panels can include a handle. FIG. 4B illustrates the panel, associated with platform 440 as having a protruding handle 470 physically coupled to the panel. FIG. 4C illustrates the panel, associated with platform 440 as having a recessed handle 470 that is part of the panel. In some embodiments, without or without a handle, a panel can be flush or substantially flush with adjacent structures (e.g., adjacent panel(s), adjacent frame of exterior housing, etc.), as illustrated in FIGS. 4A-4C.

In some embodiments, system 400 can provide an agitation function for agitating a biological fluid during treatment of the biological fluid by illumination. The agitation may facilitate the treatment, for example, by providing for mixing of a compound (e.g., photochemical compound, pathogen inactivation compound) in the biological fluid, or by maintaining a component (e.g., platelets, cells) of the biological fluid in suspension. System 400 can provide the agitation function via structural elements of FIGS. 4A-4I. For example, first platform 440 may include an outer region and an inner region. The outer region may comprise first panel 480 movable between a closed position and an open position, for example, as the outer region slidably moves via outer rails or tracks 462 into and out of a first (top) treatment chamber. In the closed position, first panel 480 covers a first opening to the first treatment chamber. In the open position, first panel 480 uncovers the first opening to the first treatment chamber. The outer region may also comprise a first support structure that structurally supports the inner region; for example, the outer region may include inner rails or tracks 464 that structurally support compartments 460A and 460B of the inner region. In FIG. 4A, protruding structures in the sidewalls of compartments 460A and 460B may fit in the inner rails, in some embodiments with edges of compartments 460A and 460B forming a lip over the inner rails and the outer rails. The inner region may be configured to move to agitate a first biological fluid during a time period in which the outer region is in a fixed position. For example, while system 400 illuminates a first biological fluid in compartments 460A and/or 460B, the outer region including first panel 480 may be fixed in the closed position, but the inner region may be moving in order to agitate the first biological fluid. First panel 480 and outer rails 462 may both be part of the structure of the outer region, but first panel 480 may be not attached to compartments 460A and 460B. Where first panel 480 is part of the structure of the outer region of first platform 440, first panel 480 may be integrated with the outer region structure (e.g., in one monolitically formed piece) or attached to the outer region structure (e.g., as separately formed pieces).

Movement of the inner region may be based on motion generated by one or more motors or servos. For example, the outer region may comprise one or more electric motors configured to generate the motion. The inner region may be configured to agitate the first biological fluid in compartments 460A and/or 460B based on this generated motion. System 400 may be configured to control (e.g., adjustably control) one or more aspects of the movement of the inner region, such as offset (i.e., stroke length of the reciprocating (e.g., linear, forward-and-backward, etc.) motion during agitation), speed, acceleration, and deceleration. The movement of the inner region may be forward and backward (e.g., along the inner rails of the outer region) or may encompass movement in other directions. In some embodiments, system 400 may be configured to control movement of the inner region to vary its position for purposes of calibration (e.g., calibration of an array of light sources).

One or more motors or servos may be located at a position in front of or to the rear of where the first biological fluid is to be carried by first platform 440. For example, an electric motor may be in a position in front of compartment 460B in between first panel 480 and compartment 460B. As another example, an electric motor may be in a position to the rear of compartment 460A inside system 400. As yet another example, an electric motor may be in a position in front of compartment 460B in between first panel 480 and compartment 460B while another electric motor may be in a position to the rear of compartment 460A inside system 400.

Figure 4D:
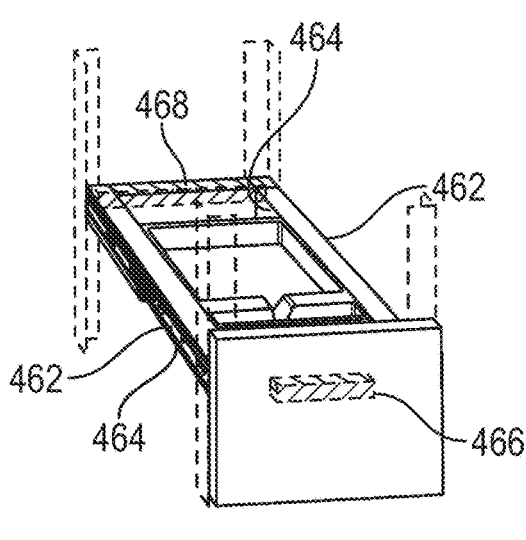
Figure 4G:
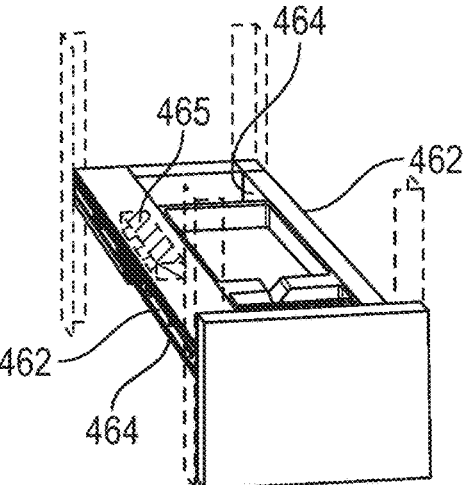
Figure 4E:
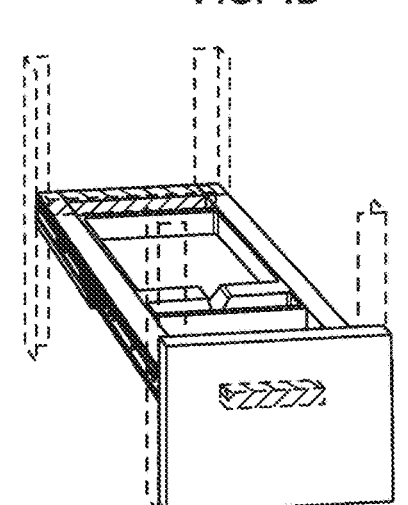
Figure 4H:
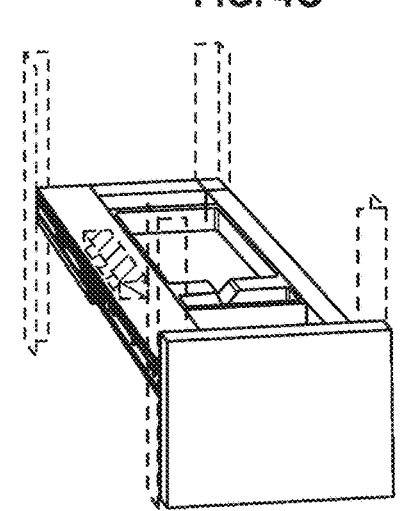
Figure 4F:
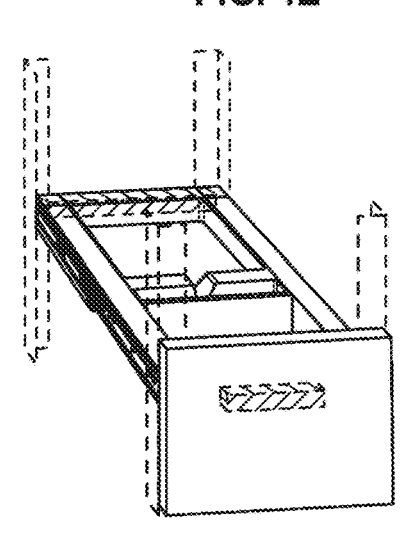

FIGS. 4D-4F illustrate another embodiment where one or more motors or servos may be located at a position in front of or to the rear of where the first biological fluid is to be carried by first platform 440. In this embodiment, outer region of first platform 440 comprises a first support structure that structurally supports the inner region via inner rails or tracks 464 that interface with the inner region (e.g., edges of the compartments of the inner region), providing structural support above, below, and/or adjacent to the edges. In this embodiment, one or more motors or servos 466, 468 may be located in front of the compartments (e.g., at the backside of first panel 480, in first panel 480, etc.) and/or to the rear of the compartments (e.g., outer region of the first platform 440 at a location to the rear of compartment 460A). FIGS. 4D-4F illustrate this embodiment where the inner region is in different positions during agitation or calibration. FIG. 4D illustrates the position when the inner region is positioned near or adjacent to first panel 480 during agitation. FIG. 4E illustrates the position when the inner region has been moved backwards along the inner rails away from first panel 480 into an intermediate position during agitation. FIG. 4F illustrates the position when the inner region has been further moved backwards along the inner rails away from first panel 480 into a rearmost position during agitation. During agitation or calibration, outer region may be fixed in position, but inner region may be moved forward and backwards through the positions shown in FIGS. 4D-4F.

One or more motors or servos may be located at a position on the right or on the left of where the first biological fluid is to be carried by first platform 440. For example, an electric motor may be in a position on the right of compartment 460A (or 460B) in between the right outer rail and compartment 460A (or 460B). As another example, an electric motor may be in a position on the left of compartment 460A (or 460B) in between the left outer rail and compartment 460A (or 460B). As yet another example, an electric motor may be in a position on the right of compartment 460A (or 460B) in between the right outer rail and compartment 460A (or 460B) while another electric motor may be in a position on the left of compartment 460A (or 460B) in between the left outer rail and compartment 460A (or 460B).

Figure 4I:
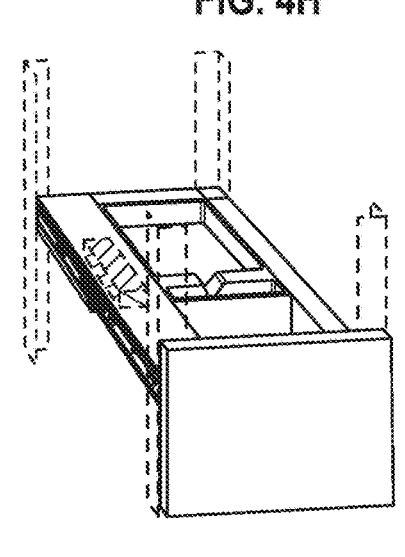

FIGS. 4G-4I illustrate another embodiment where one or more motors or servos 465 may be located at a position on the left of where the first biological fluid is to be carried by first platform 440. In this embodiment, outer region of first platform 440 comprises a first support structure that structurally supports the inner region via inner rails or tracks 464 that interface with the inner region (e.g., edges of the compartments of the inner region), providing structural support above, below, and/or adjacent to the edges. On the left of the compartments of the inner region, the outer region comprises a relatively wider structure housing one or more motors or servos. FIGS. 4G-4I illustrate this embodiment where the inner region is in different positions during agitation or calibration. FIG. 4G illustrates the position when the inner region is positioned near or adjacent to first panel 480 during agitation. FIG. 4H illustrates the position when the inner region has been moved backwards along the inner rails away from first panel 480 into an intermediate position during agitation. FIG. 4I illustrates the position when the inner region has been further moved backwards along the inner rails away from first panel 480 into a rearmost position during agitation. During agitation or calibration, outer region may remain fixed in position, but inner region may be moved forward and backwards through the positions shown in FIGS. 4G-4I.

In some embodiments, system 400 can provide an agitation function for agitating a biological fluid during treatment of the biological fluid by illumination, via second platform 450. Second platform 450 may implement teachings similar to the above teachings for the agitation function for first platform 440. For example, second platform 450 may include an outer region and an inner region. The outer region may comprise second panel 490 movable between a closed position and an open position, for example, as the outer region slidably moves via outer rails into and out of a second (bottom) treatment chamber. In the closed position, second panel 490 covers a second opening to system 400, i.e., an opening to the second treatment chamber. In the open position, second panel 490 uncovers the second opening, i.e., the opening to the second treatment chamber. The outer region may also comprise a second support structure that structurally supports the inner region; for example, the outer region may include inner rails or tracks that structurally support compartments of the inner region. The inner region may be configured to move to agitate a second biological fluid during a time period in which the outer region is in a fixed position. For example, while system 400 illuminates a second biological fluid in compartments of the inner region, the outer region including second panel 490 may be fixed in the closed position, but the inner region may be moving in order to agitate the second biological fluid. Second panel 490 and the outer rails of second platform 450 may both be part of the structure of the outer region of second platform 450, but second panel 490 may be not attached to compartments of the inner region. Where second panel 490 is part of the structure of the outer region of second platform 450, second panel 490 may be integrated with the outer region structure (e.g., in one monolitically formed piece) or attached to the outer region structure (e.g., as separately formed pieces). The outer region of second platform 450 may comprise one or more electric motors or servos configured to generate motion and thereby provide movement of the inner region. In some embodiments, system 400 may be configured to control movement of the inner region of second platform 450 to vary its position for purposes of calibration (e.g., calibration of an array of light sources).

Figure 4J:
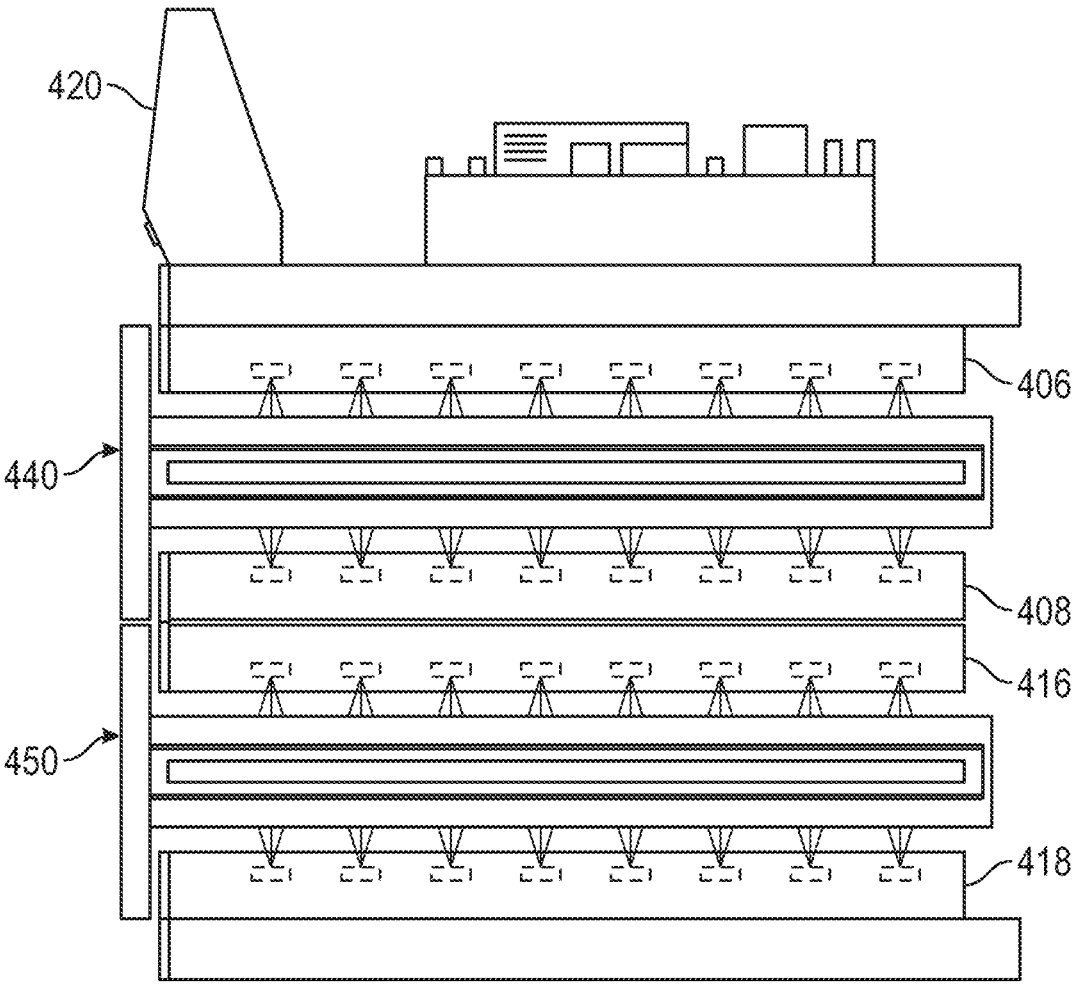

FIG. 4J illustrates a side view of the interior of system 400. At the top, this side view shows an upper stage including a display 420 (e.g., touchscreen) and control circuitry and/or a computer system. Moving down, there is a first light source array 406 located above and facing the first platform 440 with light sources oriented to shine light down in the first treatment chamber to illuminate a first biological fluid positioned on first platform 440. Moving down, there is a second light source array 408 located below and facing the first platform 440 with light sources oriented to shine light up in the first treatment chamber to illuminate the first biological fluid positioned on first platform 440. Moving down, there is a third light source array 416 located above and facing the second platform 450 with light sources oriented to shine light down in the second treatment chamber to illuminate a second biological fluid positioned on second platform 450. At the bottom, there is a fourth light source array 418 located below and facing the second platform 450 with light sources oriented to shine light up in the second treatment chamber to illuminate the second biological fluid positioned on the second platform 450. In some embodiments where illumination comes from under a platform, the bottom of that platform (e.g., the bottom of its compartments for biological fluid(s)) may be transparent to that illumination so that the illumination can reach the biological fluid(s) of that platform. In some embodiments, the platform is transparent (e.g., wholly or partially transparent, at least 85% transparent, sufficiently transparent for treating a biological fluid, sufficiently transparent to achieve a desired treatment outcome) to light with a wavelength within 100 nm (e.g., 75 nm, 50 nm, 40 nm, 30 nm, 20 nm) of the peak wavelength of light used for illumination. In some embodiments, the platform is transparent (e.g., wholly or partially transparent, at least 85% transparent, sufficiently transparent for treating a biological fluid, sufficiently transparent to achieve a desired treatment outcome) to ultraviolet light (e.g., UV-A, UV-B, and/or UV-C).

Electrical wiring for powering and/or controlling the electric motor(s) or servo(s) may be located inside or along the outer region, e.g., inside the inner rails or along (internal or external) sidewalls, or top or bottom surfaces of the outer regions. Such locations for electrical wiring outside of the compartments of the platforms (e.g., outside inner regions of the platforms) avoid occluding illumination from the light source arrays that shine light onto the compartments from above or below.

Figure 4K:
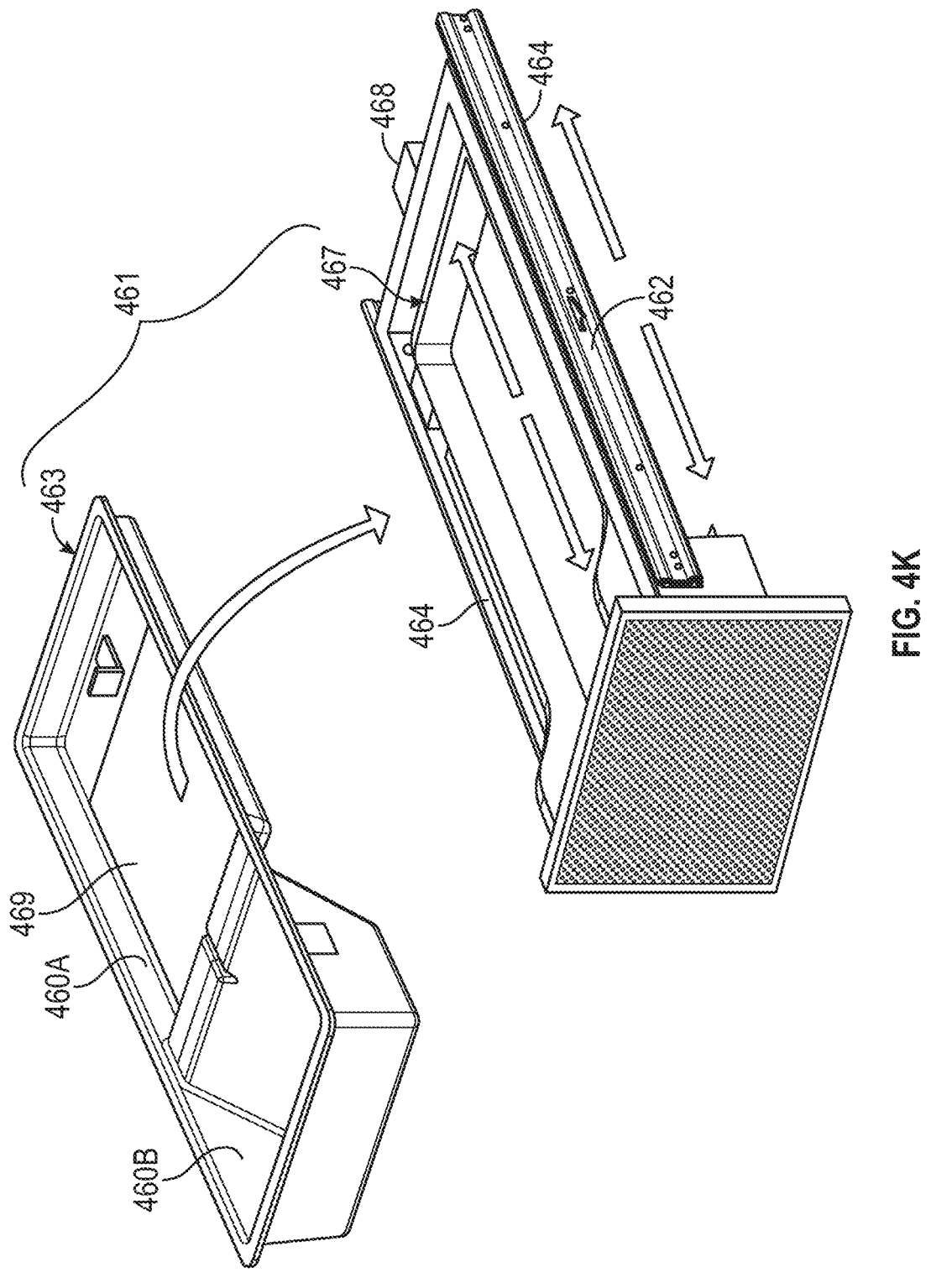

In some embodiments, one or more platforms of system 400 can each include an inner region assembly 461 that provides one or more removable inner region portions, as illustrated in FIG. 4K. The inner region assembly 461 may include one or more removable portions 463 (e.g., in the form of a tray, well, plate, stage, etc.) and a cradle 467 portion of the inner region for receiving the one or more removable portions 463. The removable portion 463 may include a rear compartment 460A with a compartment floor 469 made of material that is wholly or partially transparent (e.g., at least 85% transparent, sufficiently transparent for treating a biological fluid, sufficiently transparent to achieve a desired treatment outcome) to light (e.g., peak wavelengths of light) emitted by an array of light sources as provided herein (e.g., ultraviolet light, UV-A, UV-B, and/or UV-C) e.g., glass, Plexiglas® (e.g., Plexiglass® G-UVT). The compartment floor 469 itself may be removable from rear compartment 460A so as to be replaceable and/or cleanable. The rear compartment 469 may be configured to carry one or more containers containing one or more biological fluids in one or more positions for illumination from above and/or below the container(s). The front compartment 460B may be configured to carry one or more other containers but not in a position for illumination. The containers for the front compartment and for the rear compartment may all be part of a multi-container assembly. The cradle 467 may align and hold the one or more removable portions 463 in a stable position and in a desirable orientation. The cradle 467 may be supported by the outer region of the platform, such as for example mounted to or in inner rails or tracks 464 that are included in the outer region of the platform. One or more motors or servos 468 may be mounted to or on the platform (e.g., outer region of the platform) and located to the rear of rear compartment ##. The one or more motors or servos 468 may be physically coupled to the cradle 467 and may move the cradle 467 forward and backward (e.g., along the inner rails or tracks 464 of the outer region of the platform) to agitate biological fluid carried on the platform (e.g., biological fluid in a container). The one or more motors or servos 468 may be part of any suitable agitation design (e.g., a lead screw design where one or more motors or servos move a lead screw that is attached to the cradle, a belt-driven design where one or more motors or servos move one or more belts that rotate one or more gears (e.g., gears with teeth) that engage and move one or more tracks attached to the cradle) and may operate based on control signals from electrical wiring that is electrically connected to control circuitry. In some embodiments, the agitation speed may be adjustable (e.g., adjusted to have different speeds between different treatments, adjusted to have different speeds during a single treatment, adjusted based on a predetermined speed plan, adjusted dynamically in real-time based on a user's input in real-time), Such control circuitry may control the one or more motors or servos 468 based on a control program implemented as software and/or hardware of the control circuitry. Outer rails or tracks 462 may be part of the structure of the outer region of the platform, and the outer region may slidably move via outer rails or tracks 462 into and out of the platform's treatment chamber. Sensors for the platform may include, for example: platform position/lock/latch sensor for sensing whether the platform is in a closed position and/or locked/latched or not, cradle position sensor for sensing the position of the cradle along the inner rails or tracks 464, removable inner region portion sensor for sensing whether one or more removable inner region portions are in the cradle or not, temperature sensor(s) for sensing the temperature of the platform or biological fluid carried on the platform at one or more locations (e.g., location of rear compartment 460A, location of front compartment 460B, location(s) of one or more motors or servos 468), sensor(s) for sensing the presence and/or weight of a biological fluid (e.g., biological fluid in a container) carried on the platform, etc.

Figure 4L:
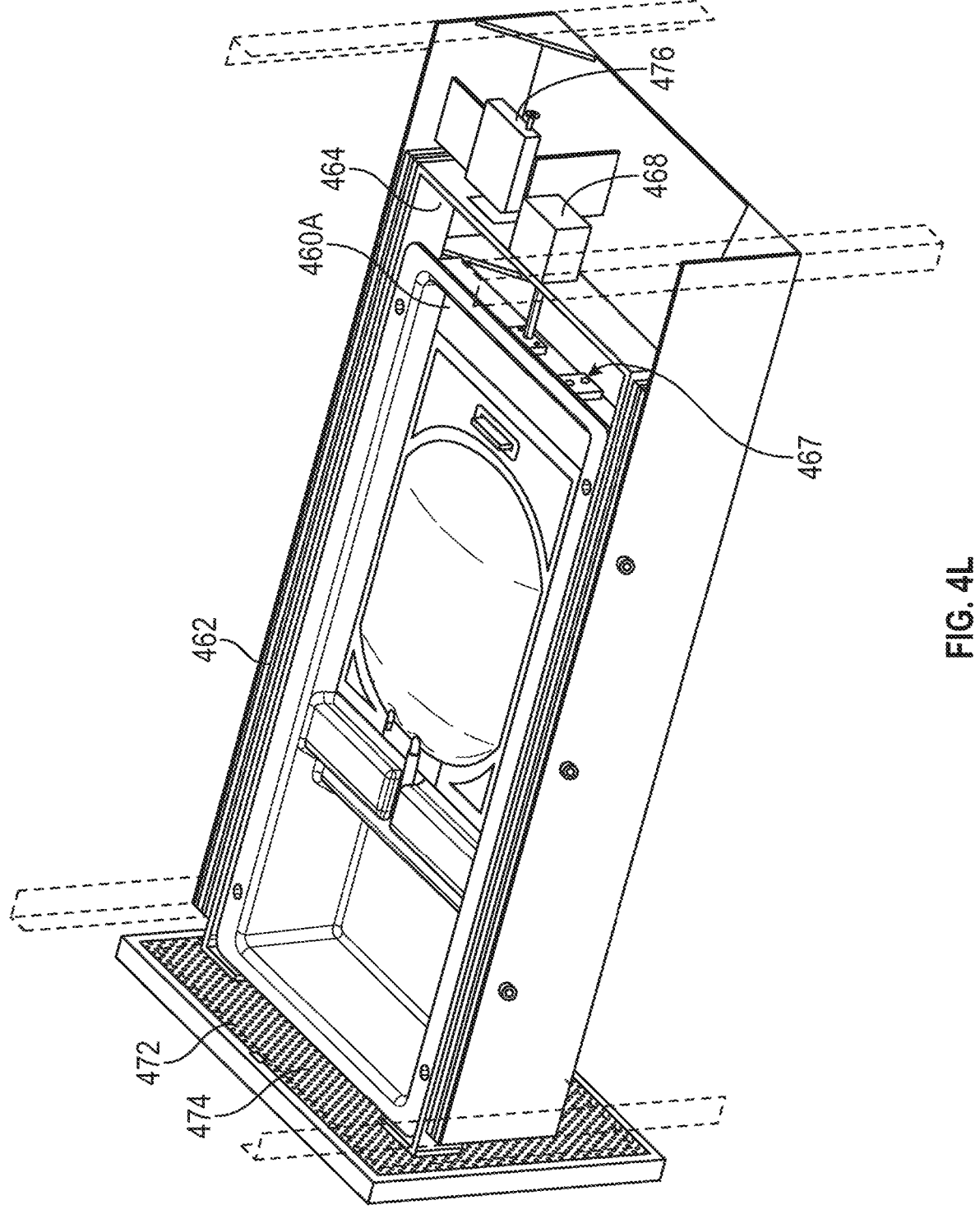

FIG. 4L shows a rear perspective view of the platform shown in FIG. 4K. In this rear perspective view, the backside of the platform's front panel is shown. Inside the front panel, the front panel may include a filter compartment 472, which may include an air filter 474, which can filter incoming air. The filter compartment 472 may be accessible so that the air filter 474 can be replaceable and/or cleanable. FIG. 4L shows the one or more motors or servos 468 mounted to or on the platform (e.g., outer region of the platform) and located to the rear of rear compartment 460A. The one or more motors or servos 468 may be physically coupled (e.g., by a lead screw, by a belt and gear and track) to the cradle 467 of the inner region and may move the cradle 467 forward and backward (e.g., along the inner rails or tracks 464 of the outer region of the platform) to agitate biological fluid when in rear compartment 460A. FIG. 4L shows a platform lock assembly 476 that is physically coupled to the structure of the outer region of the platform. When the platform lock assembly is in an unlocked state, the front panel can be opened and the outer region can slidably move via outer rails or tracks 462 into and out of the treatment chamber. When the platform lock assembly is in a locked state, the platform lock assembly engages a lock mechanism to prevent the front panel from being opened and outer region from being movable. In some embodiments, the lock mechanism may be: motor-based (e.g., locking a motor/servo physically coupled to the outer region or front panel so that the outer region cannot move), latch-based (e.g., moving a rigid member (e.g., latch or pin or hook) to engage a receiving structure (e.g., a slot or hole or groove) that is physically coupled to the outer region or front panel so that the outer region cannot move), magnetic-based (e.g., engaging electromagnet(s) to magnetically hold together the structure of the outer region of the platform and a fixed structure of system 100, where an electromagnet may be located on or in the structure of the outer region of the platform or the fixed structure of system 100 or both), etc. FIG. 4L shows the lateral sides of the platform (e.g., lateral sides of the outer region of the platform) as supported by fixed structures that can support the outer rails or tracks 462 of the outer region of the platform.

Although the systems are illustrated as having platforms arranged horizontally or vertically in FIGS. 1-4L, the illustrated platform arrangements are not limiting. For example, platforms of a four-treatment chamber and/or four-platform system can be arranged in a two-by-two array.

Above FIGS. 1-4L, and below FIGS. 9A-9F, are generally directed to teachings on system form factor, user interface elements, housing configurations, and treatment chamber configurations. All systems in FIGS. 1-4L and 9A-9F may treat biological fluids by illumination. For the systems in FIGS. 1-4L and 9A-9F, further details about their illumination features (e.g., light source arrays, light source channels, peak wavelengths, light intensities, types of light, spectral bandwidth) are provided through FIGS. 5-8 and their corresponding disclosures below.

Figure 5:
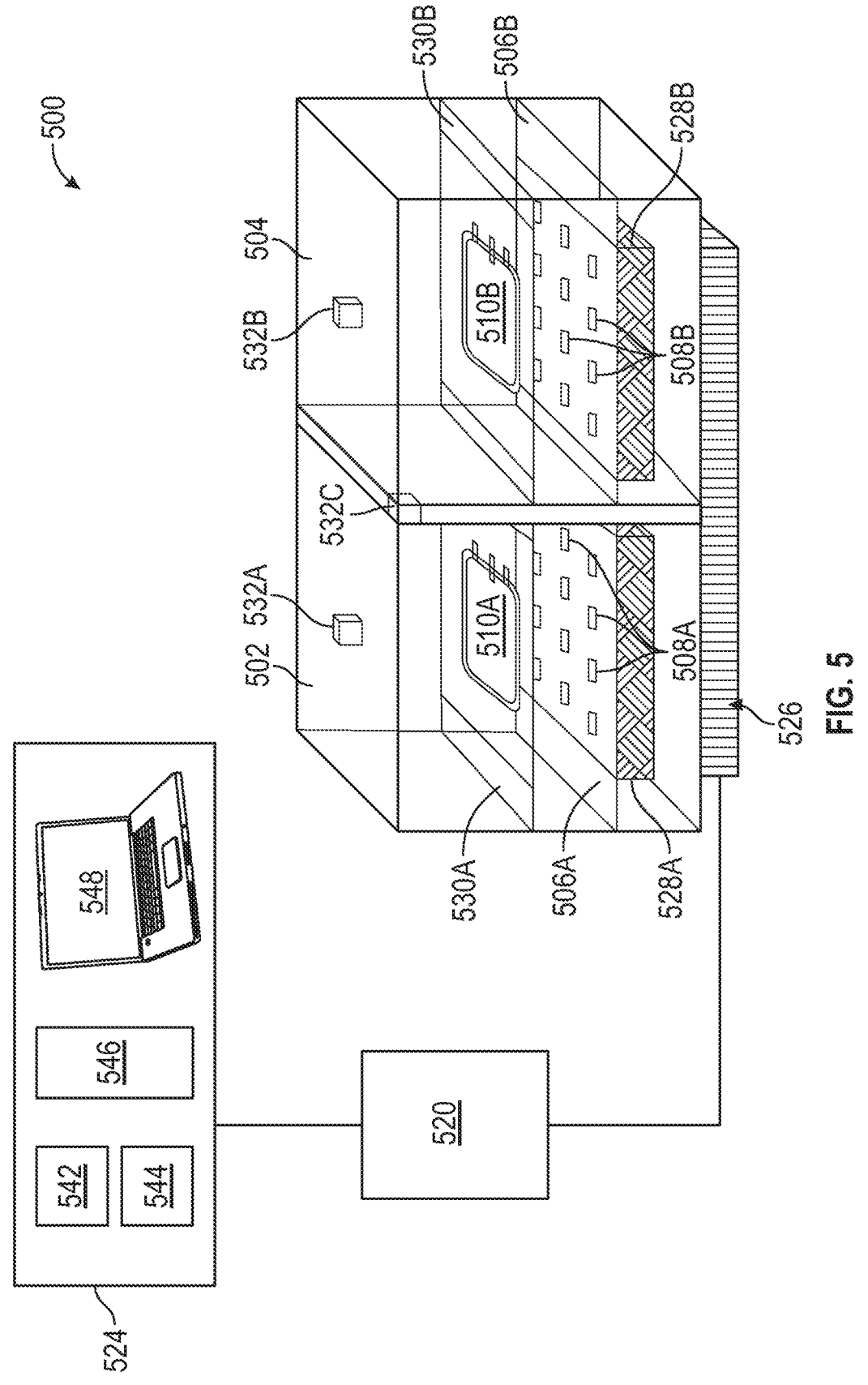
FIG. 5 is a perspective view of an exemplary system for treating a biological fluid.

FIG. 5 is a perspective view of an exemplary system 500 for treating a biological fluid. In some embodiments, the system 500 is substantially similar to system 100, as illustrated in FIG. 1. Exemplary system 500 for treating biological fluids includes a first treatment chamber 502 and a second treatment chamber 504 for receiving one or more biological fluids 510 and an array of light sources 506 positioned to illuminate one or more biological fluids 510 (e.g., positioned below and illuminating upward to the biological fluid(s)). In some embodiments, the array of light sources 506 may comprise the only light sources in chamber 502 and 504 positioned to illuminate the one or more biological fluids 510. In other embodiments described below with respect to FIG. 7, multiple light source arrays may be used to illuminate one or more biological fluids positioned in various embodiments of chamber 502 and 504 (e.g., two light source arrays positioned vertically (above and below each other), each light source array used to illuminate one or more biological fluids in FIG. 7). As described herein, an "array of light sources" means one or more light sources disposed on any two or three dimensional surface (e.g., contiguous surface, non-contiguous surface).

One or more light source channels may be included in an array of light sources of the present disclosure. In some embodiments, one or more light source channels 508 are included in array of light sources 506. Although specific light sources are illustrated as belonging to a specific light source channel, it is understood that different combinations of the light sources can form different light source channels. Each light source channel 508 may be a set of one or more light sources having substantially the same wavelength (e.g., peak wavelength, maximum peak wavelength). In an exemplary set, one light source may have a peak wavelength. In another exemplary set, two light sources may have the same peak wavelength to each other. In yet another exemplary set, each of a plurality of light sources may have different peak wavelengths from each other. In a further exemplary set, a first subset of one or more light sources may have one peak wavelength, and a second subset of one or more light sources may have a different peak wavelength. Within a light source channel having a plurality of light sources, all of the light sources may have respective peak wavelengths (e.g., maximum peak wavelengths) that all are within a wavelength range (e.g., range of 1-20 nm, 1-10 nm; e.g., 1 nm, 2 nm, 3 nm, 4 nm, 5 nm, or more, greater than and/or less than a particular wavelength) for the light source channel. For example, in some embodiments, within a light source channel having a plurality of light sources, all of the light sources may have peak wavelengths within a range set forth in the present disclosure, such as for example of about 315 nm to about 350 nm (e.g., about 315 nm to about 335 nm, about 330 nm to about 350 nm, about 340 nm to about 350 nm). In a light source channel, each light source may be any light source providing light of a desirable property (e.g., peak wavelength, maximum peak wavelength, spectral bandwidth) including, but not limited to, solid-state lighting (SSL), light-emitting diodes (LEDs), organic light-emitting diodes (OLEDs), polymer light-emitting diodes (PLEDs), and laser diodes. The light source channels of the array of light sources may be connected in a series circuit, in a parallel circuit, or in a combination of series and parallel circuits. In a light source channel having a plurality of light sources, those light sources may be controlled together or separately.

Each light source channel may be adjusted or set to emit light at different intensities (e.g., adjust the light dosage, adjust the energy dosage) at which light of the one or more peak wavelengths are applied to one or more portions of the biological fluid. For example, each light source channel may emit light at maximum intensity (e.g., 100%), or at less than maximum intensity (e.g., about 90%, about 80%, about 70%, about 60%, about 50%, about 40%, about 30%, about 20%, or less).

Each light source channel may emit various types of light. For example, each light source channel may emit ultraviolet light, ultraviolet A light, ultraviolet B light, ultraviolet C light, and/or visible light. Additionally, each light source channel may emit light of various peak wavelengths. For example, the emitted peak wavelength(s) may be in the ultraviolet A spectrum (e.g., 315-400 nm), the ultraviolet B spectrum (e.g., 280-315 nm), the ultraviolet C spectrum (e.g., 100-280 nm, 200-280 nm, 240-280 nm), or the visible light spectrum (e.g., 400-800 nm). In some embodiments, the emitted peak wavelength(s) may be between about 240 nm and about 250 nm, about 245 nm and about 255 nm, about 250 nm and about 260 nm, about 255 nm and about 265 nm, about 260 nm and about 270 nm, about 265 nm and about 275 nm, about 270 nm and about 280 nm, or about 275 nm and about 285 nm. In some embodiments, the emitted peak wavelength(s) may be between about 280 nm and about 290 nm, about 285 nm and about 295 nm, about 290 nm and about 300 nm, about 300 nm and about 310 nm, about 305 nm and about 315 nm, or about 310 nm and about 320 nm. In some embodiments, the emitted peak wavelength(s) may be between about 315 nm and about 325 nm, about 320 nm and about 330 nm, about 325 nm and about 335 nm, about 330 nm and about 340 nm, about 335 nm and about 345 nm, about 340 nm and about 350 nm, about 345 nm and about 355 nm, about 350 nm and about 360 nm, about 355 nm and about 365 nm, about 360 nm and about 370 nm, about 365 nm and about 375 nm, about 370 nm and about 380 nm, about 375 nm and about 385 nm, about 380 nm and about 390 nm, about 385 nm and about 395 nm, about 390 nm and about 400 nm. In some embodiments, the emitted peak wavelength may be about 240 nm, about 245 nm, about 250 nm, about 255 nm, about 260 nm, about 265 nm, about 270 nm, about 275 nm, about 280 nm, about 285 nm, about 290 nm, about 295 nm, about 300 nm, about 305 nm, about 310 nm, about 315 nm, about 320 nm, about 325 nm, about 330 nm, about 335 nm, about 340 nm, about 345 nm, about 350 nm, about 355 nm, about 360 nm, about 365 nm, about 370 nm, about 375 nm, about 380 nm, about 385 nm, about 390 nm, about 395 nm, or about 400 nm. In some embodiments, the emitted peak wavelength may be between about 255 nm and about 275 nm (e.g., between about 260 nm and about 270 nm, about 265 nm). In some embodiments, the emitted peak wavelength may be between about 275 nm and about 295 nm (e.g., between about 280 nm and about 290 nm, about 285 nm). In some embodiments, the emitted peak wavelength may be between about 300 nm and about 320 nm (e.g., between about 305 nm and about 315 nm, about 310 nm). In some embodiments, the emitted peak wavelength may be between about 315 nm and about 335 nm (e.g., between about 320 nm and about 330 nm, about 325 nm). In some embodiments, the emitted peak wavelength may be between about 330 nm and about 350 nm (e.g., between about 335 nm and about 345 nm, between about 340 nm and about 350 nm, about 340 nm, about 345 nm). In some embodiments, the emitted peak wavelength may be between about 355 nm and about 375 nm (e.g., between about 360 nm and about 370 nm, about 365 nm). In some embodiments, the emitted peak wavelength may be between about 375 nm and about 395 nm (e.g., between about 380 nm and about 390 nm, about 385 nm). In some embodiments, the emitted peak wavelengths may be in the (1) ultraviolet A spectrum (e.g., 315-400 nm); and (2) the ultraviolet B spectrum (e.g., 280-315 nm) or the ultraviolet C spectrum (e.g., 100-280 nm, 200-280 nm, 240-280 nm). In some embodiments, the emitted peak wavelength is in the ultraviolet A spectrum, between about 315 nm and about 350 nm (e.g., between about 320 nm and about 345 nm, between about 315 nm and about 335 nm, between about 330 nm and about 350 nm, between about 340 nm and about 350 nm).

In some embodiments, all light source channels of array of light sources may emit light of about the same (e.g., within variance ±1 nm, ±2 nm, ±3 nm, ±4 nm, ±5 nm, ±6 nm, ±7 nm, ±8 nm, ±9 nm, ±10 nm) peak wavelength (e.g., maximum peak wavelength). For example, in some embodiments, all light source channels of an array of light sources may emit light of a peak wavelength of 325±10 nm, 330±10 nm, 335±10 nm, 340±10 nm, 325±5 nm, 330±5 nm, 335±5 nm, 340±5 nm, 345±5 nm, 345±4 nm, 345±3 nm, or 345±2 nm. Light source channels may include a plurality of light sources with different peak wavelengths (e.g., measured peak wavelengths) within a range of variability. In some embodiments, the average peak wavelength across a plurality of light sources for a single light source channel may be the same as a particular peak wavelength for a particular light source in the single light source channel. In other embodiments, the average peak wavelength across a plurality of light sources of a single light source channel may be different (e.g., about 1 nm, 2 nm, 3 nm, 4 nm, 5 nm or more, greater than or less than) than all particular peak wavelengths of each light source in the single light source channel. In some embodiments, some light source channels may emit light of a first peak wavelength and other light source channels may emit light of a second peak wavelength. The first peak wavelength may differ from the second peak wavelength by at least (e.g., greater than) 5 nm, 10 nm, 15 nm, or 20 nm, or more. For example, in a non-limiting embodiment, a first light source channel may emit light with a peak wavelength in the ultraviolet A spectrum, such as described above (e.g., between about 315 nm and about 335 nm, between about 330 nm and about 350 nm, between about 340 nm and about 350 nm) and a second light source channel may emit light with a peak wavelength in the ultraviolet C spectrum, such as described above (e.g., between about 250 nm and about 260 nm, between about 260 nm and about 270 nm) or the ultraviolet B spectrum, such as described above (e.g., between about 305 nm and about 315 nm). In another non-limiting embodiment, a first light source channel may emit light with a peak wavelength in the ultraviolet A spectrum, such as described above (e.g., between about 330 nm and about 350 nm, between about 340 nm and about 350 nm) and a second light source channel may emit light with a peak wavelength also in the ultraviolet A spectrum, such as described above (e.g., between about 315 nm and about 335 nm, between about 355 nm and about 375 nm). In some embodiments, a first peak wavelength is the average peak wavelength of the one or more light sources of a first light source channel. In some embodiments, the array of light sources may comprise first, second, and third light source channels that each respectively emits light of a first, second, and third peak wavelength. In some embodiments, a first peak wavelength may differ from a second peak wavelength by at least (e.g., greater than) 5 nm, 10 nm, 15 nm, or 20 nm or more, and/or the second peak wavelength may differ from a third peak wavelength by at least (e.g., greater than) 5 nm, 10 nm, 15 nm, or 20 nm or more. Alternatively, each of a first, second, and third peak wavelengths may differ from each another by at least (e.g., greater than) 5 nm, 10 nm, 15 nm, or 20 nm, or more. In some embodiments, an array of light sources may comprise first, second, third, and fourth light source channels that each respectively emits light of a first, second, third, and fourth peak wavelength. In some embodiments, at least two, at least three, or at least four of the first, second, third, and fourth peak wavelengths may differ from each other by at least (e.g., greater than) 5 nm, 10 nm, 15 nm, or 20 nm or more. Alternatively, each of the first second, third, and fourth peak wavelengths may differ from each other by at least (e.g., greater than) 5 nm, 10 nm, 15 nm, or 20 nm, or more. Alternatively, the first peak wavelength may be the about same as (e.g., equal to, within variance ±1 nm, ±2 nm, ±3 nm, ±4 nm, ±5 nm) the third peak wavelength, the second peak wavelength may be the about same as (e.g., equal to) the fourth peak wavelength, and the first peak wavelength may differ from the second peak wavelength by at least (e.g., greater than) 5 nm, 10 nm, 15 nm, or 20 nm.

In some embodiments, each light source channel may emit light with a narrow spectral bandwidth. For example, the full-width half-maximum (FWHM) spectral bandwidth of light (e.g., spectral bandwidth at the maximum peak intensity) emitted by each light source channel may be less than 20 nm, less than 18 nm, less than 16 nm, less than 14 nm, less than 12 nm, less than 10 nm, less than 9 nm, less than 8 nm, less than 7 nm, less than 6 nm, or less than 5 nm. In some embodiments, the full-width half-maximum (FWHM) spectral bandwidth of light emitted by each light source channel is within 10 nm less than and/or within 10 nm greater than the peak wavelength (e.g., no more than 10 nm greater than, no more than 10 nm less than the peak wavelength). In some embodiments, the full-width half-maximum (FWHM) spectral bandwidth of light emitted by each light source channel may be greater than 1 nm, greater than 2 nm, greater than 3 nm, or greater than 4 nm, or more. In other examples, 50% of the maximum peak intensity of light emitted by each light source channel is within 10 nm, within 9 nm, within 8 nm, within 7 nm, within 6 nm, within 5 nm, within 4 nm, or within 3 nm of the peak wavelength (e.g., no more than 10 nm greater than, no more than 10 nm less than the peak wavelength; within 10 nm less than, within 10 nm more than the peak wavelength). In other examples, the light intensity at 50% of the maximum peak intensity of light emitted by each light source channel is within a spectral width less than 20 nm, less than 18 nm, less than 16 nm, less than 14 nm, less than 12 nm, less than 10 nm, less than 9 nm, less than 8 nm, less than 7 nm, less than 6 nm, or less than 5 nm (e.g., no more than 10 nm greater than, no more than 10 nm less than the peak wavelength; within 10 nm less than, within 10 nm greater than the peak wavelength). Commercially available LEDs and laser diodes are non-limiting examples of light sources that may provide such narrow spectral bandwidth illumination at the peak wavelengths discussed above.

In some embodiments, one or more of the peak wavelength of emission, the spectral bandwidth of emission, the duration of emission, and the intensity of emission of each light source channel 508 may be adjusted or set.

Adjustment of these various light source channel parameters may be performed by a control circuitry 520 operatively coupled (e.g., communicatively coupled) to treatment chambers 502 and 504, light source arrays 506, and/or to computer system 524. As used herein, "operatively coupled" refers to any wired or wireless connection between two or more components that enables the two or more components to exchange information, control instructions, and/or control signals. As will be discussed in more detail below, control circuitry 520 may receive control instructions and/or control signals from computer system 524 and send control instructions and/or control signals to various components of treatment chambers 502 and 504 to adjust or set various parameters associated with various components of chambers 502 and 504. Adjustment of various parameters of chambers 502 and 504 may be desirable to ensure that the chamber's treatment parameters are in accordance with the treatment profiles of the one or more biological fluids 510. It should be recognized that, in some examples, control circuitry 520 and/or the function of control circuitry 520 may be included within computer system 524. In some examples, control circuitry 520 may include computer system 524 and/or the function of computer system 524. In some examples, control circuitry 520 may be structurally attached to treatment chambers 502 and 504 (e.g., attached to external side, top, and/or bottom surface of treatment chambers 502 and 504). In some examples, control circuitry 520 may be integrated with treatment chambers 502 and 504 (e.g., located inside treatment chambers 502 and 504 or forming a part of the structure of treatment chambers 502 and 504).

Computer system 524 may be operatively coupled (wired or wirelessly) to control circuitry 520 and/or to any of the various sensors discussed herein. Computer system may include one or more processors 544 (644 in FIG. 7, 744 in FIG. 7), memory 542 (642 in FIG. 7, 742 in FIG. 7), an input/output (I/O) interface 546 (646 in FIG. 7, 746 in FIG. 7), and a user interface (UI) 548 (648 in FIG. 6, 748 in FIG. 7). One or more processors 544 may be one or more of any type of general purpose computer processor. Memory, or computer readable medium 542 may include one or more of readily available memory such as random access memory (RAM), read-only memory (ROM), floppy disk, hard disk, optical storage media (e.g., compact disc or digital video disc), flash drive, or any other form of digital storage, local or remote. In some examples, a non-transitory computer-readable storage medium of memory 542 may be used to store instructions for illuminating one or more biological fluids in accordance with their one or more treatment profiles, as will be discussed herein. Computer system 524 may encompass any variety of computers, such as a personal computer (PC), a desktop computer, a laptop, a computer terminal, a server computer, a tablet computer, a smartphone, a personal digital assistant (PDA), etc. In some examples, control circuitry 520 and/or the function of control circuitry 520 may be included within computer system 524.

At UI 548, a user may input one or more characteristics of a set of characteristics of one or more biological fluids (e.g., biological fluid 510). Alternatively, or additionally, the one or more characteristics of a set of characteristics of one or more biological fluids may be determined based on feedback input to computer system 524 and/or control circuitry 520 from one or more sensors for a treatment chamber (e.g., treatment chamber 502, treatment chamber 504). The characteristics of the set of characteristics of a biological fluid may include, for example, the type of the biological fluid (e.g., blood product, such as plasma, platelets, red blood cells; cells, such as eukaryotic cells; proteins, such as antibodies; vaccines), the photochemical agent in the biological fluid (e.g., type, volume, concentration), the volume of the biological fluid, the transmissivity of the biological fluid, the type and/or shape of the container carrying the biological fluid, and the temperature of the biological fluid.

At UI 548, a user may input one or more parameters that comprise the treatment profiles of one or more biological fluids (e.g., biological fluid 510). Alternatively or additionally, computer system 524 may automatically determine one or more parameters of the one or more treatment profiles of one or more biological fluids (e.g., biological fluids 510) based on the respective set of characteristics of the one or more biological fluids. In particular, memory 542 may store a computer program comprising instructions that map one or more characteristics of a biological fluid to one or more parameters of a treatment profile of the biological fluid for each biological fluid. The instructions that that map one or more characteristics of a biological fluid to one or more parameters of a treatment profile of the biological fluid for each biological fluid may be implemented as a set of user-programmable rules.

In some embodiments, array of light sources 506 may be thermally coupled to a heat exchanger 528 (e.g., heat sink, fin heat sink, heat exchanger that may be operatively coupled to and controlled by control circuitry 520). Heat exchanger 528 may draw thermal energy away from array 506 facing one or more biological fluids 510, thus minimizing the exposure of biological fluids 510 to thermal energy (e.g., thermal energy that may damage biological function). Further control of the temperature of chambers 502 and 504 and/or the temperature of the one or more biological fluids 510 may be provided by a heating/cooling unit 526 that may be operatively coupled to and controlled by control circuitry 520 and configured to adjust or set the temperature of chambers 502 and 504. Heating/cooling unit 526 may be any suitable technology known in the art, such as for example, a fan, heat pump, Peltier cooler and/or heat pipe, or any combination of such technology. Heating/cooling unit 526 may be external to, inside, and/or integrated with chambers 502 and 504. For example, one or more fans may be positioned in the rear of the treatment chamber(s) to draw in air through an inlet on the exterior housing of system 500 and to expel the air through an outlet exhaust on the back of the exterior housing.

In some embodiments, heating/cooling unit 526 may be a heating unit or a cooling unit or a heating-and-cooling unit. Through the use of heating/cooling unit 526, system 500 can control the heating/cooling unit 526 to maintain the temperature of a biological fluid within a certain temperature range (e.g., a range of 1° C., a range of 2° C., a range of 3° C., etc.) during treatment of the biological fluid by illumination. For example, heat or temperature sensors can provide temperature indications or measurements to control circuitry 520 or to computer system 524 via control circuitry

520. If control circuitry 520 and/or computer system 524 processes or interpret the temperature indications or measurements as indicating the crossing of a certain threshold or condition related to a target temperature value or profile, control circuitry 520 and/or computer system 524 may instruct or command or enable or engage or actuate heating/cooling unit 526 to take action to adjust the temperature of chamber 502 or 504 and/or the temperature of the one or more biological fluids 510. For example, control circuitry 520 and/or computer system 524 may instruct or command or enable or engage or actuate one or more fans to start blowing to initiate cooling, to blow faster to provide an increased cooling rate, to blow slower to provide a decreased cooling rate, or to stop blowing to cease cooling. During treatment of the biological fluid by illumination, the one or more fans may run in operational cycles under the control of control circuitry 520 and/or computer system 524 in order to maintain the temperature of the biological fluid within a certain temperature range (e.g., a range of 1° C., a range of 2° C., a range of 3° C., etc.). Control circuitry 520 and/or computer system 524 may instruct or command or enable or engage or actuate any other suitable technology known in the art, such as for example, a fan, heat pump, Peltier cooler and/or heat pipe, or any combination of such technology to take action to adjust the temperature of chamber 502 or 504 and/or the temperature of the one or more biological fluids 510.

In some embodiments, the one or more fans may be located at the rear of the treatment chamber(s). The one or more fans may blow air in a front-to-back direction or in a back-to-front direction or both. In some embodiments, the one or more fans may draw in air to pass through the treatment chamber and expel the air through an exhaust at the rear of the system. Inlet air to the one or more fans may enter through vents located at or near the front or side(s) of the treatment chamber(s), and outlet air from the one or more fans may exit through vents located at the rear of the treatment chamber(s).

Treatment chambers 502 and 504 may further include a plurality of interior surfaces configured to absorb light (e.g., each configured to absorb light), such as for example, one or more walls made of or coated by a material (e.g., black plastic, black silicate, black paint) that substantially absorbs light of certain wavelengths. Alternatively or in addition, in some embodiments, treatment chambers 502 and 504 may further include one or more interior surfaces configured to reflect light (e.g., each configured to reflect light), such as for example, one or more walls made of or coated by a material that substantially reflects light of certain wavelengths.

Treatment chambers 502 and 504 may further comprise a platform 530 configured to hold one or more biological fluids 510 (e.g., containers of biological fluids). Platform 530 may be any support suitable for carrying biological fluids or containers of biological fluids. Platform 530 may be positioned in a "drawer configuration" so that it is slidably movable manually into and out of chambers 502 and 504. Platform 530 may be slidably movable automatically by any suitable actuator, such as an electric motor or servo. Platform 530 carrying biological fluids 510 may be positioned above the light source array 506 with light source array 506 facing platform 530. However, in other embodiments, platform 530 carrying one or more biological fluids may be positioned below light source array 506 with light source array 506 facing the platform 530.

In some embodiments, the system 500 includes one or more scanners 532 in the treatment chambers 502 and 504. The one or more scanners 532 can be located above the biological fluids 510 when the fluids are positioned for treatment (e.g., scanner 532A in the first treatment chamber, scanner 532B in the second treatment chamber). As illustrated, one or more scanners 532 (e.g., scanner 532C) can also be located between the first and second treatment chambers at the exterior (e.g., exterior housing, exterior surface) of the system 500. The one or more scanners 532 can be substantially similar to the scanners described herein. In some embodiments, when the biological fluids are loaded into a respective treatment chamber, a respective scanner within a respective chamber can obtain identifying information about the biological fluids, as described herein. In some embodiments, the one or more scanners can be positioned at or near a first opening of the first treatment chamber 502, at or near a second opening of the second treatment chamber 504, or at or near openings of both chambers, such as for example, to obtain identifying information about the biological fluid prior to the biological fluids being positioned within a respective treatment chamber.

Each platform 530A and 530B may be configured to carry a first biological fluid 510A and a second biological fluid 510B respectively in a first container (e.g., flexible container, bag) and a second container (e.g., flexible container, bag) respectively. Each container may have a volume capacity, e.g., up to about 3000 mL, up to about 2500 mL, up to about 2000 mL, up to about 1500 mL, up to about 1400 mL, up to about 1300 mL, up to about 1200 mL, up to about 1100 mL, up to about 1000 mL, up to about 950 mL, up to about 900 mL, up to about 850 mL, up to about 800 mL, up to about 750 mL, up to about 700 mL, up to about 650 mL, up to about 600 mL, up to about 550 mL, or up to about 500 mL.

Figure 6:
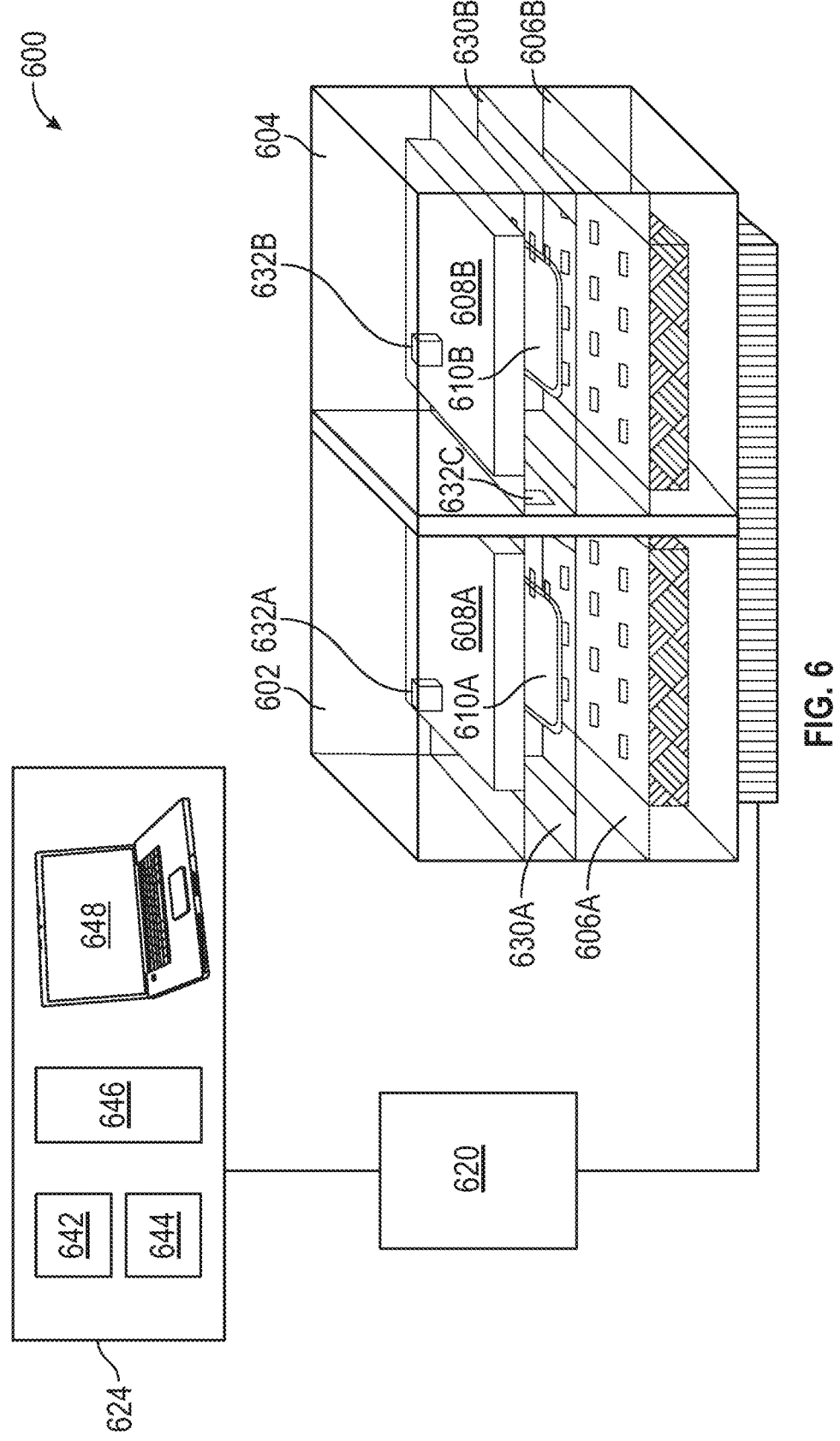
FIG. 6 is a perspective view of an exemplary system for treating a biological fluid.

FIG. 6 is a perspective view of an exemplary system 600 for treating a biological fluid. In some embodiments, the system 600 is substantially similar to system 500, as illustrated in FIG. 5. Exemplary system 600 for treating biological fluids includes a first treatment chamber 602 and a second treatment chamber 604 for receiving one or more biological fluids 610, a first array of light sources 606 in each chamber positioned to illuminate from below one or more biological fluids 610, a second array of light sources 608 in each chamber positioned to illuminate from above one or more biological fluids 610, a platform 630 in each chamber configured to hold one or more biological fluids 510 (e.g., containers of biological fluids), and a sensor (e.g., scanner) 632 configured to obtain identifying information of a biological fluid loaded into the treatment chamber. The first array of light sources 606 and second array of light sources 608 positioned above and below the one or more biological fluids 610 in each of treatment chambers 602 and 604 provides for illuminating the biological fluid from either one (i.e., above or below) or two (i.e., both) directions.

The system 600 can include scanner 632A positioned at the exterior (e.g., exterior housing, exterior surface) of the system 600 at a location associated with the first treatment chamber 602 (e.g., at or near an opening of first treatment chamber 602) and scanner 632B positioned at the exterior (e.g., exterior housing, exterior surface) of the system 600 at a location associated with the second treatment chamber 604 (e.g., at or near an opening of second treatment chamber 604), such as for example, to obtain identifying information about the biological fluid prior to the biological fluids being positioned within a respective treatment chamber. The system 600 can also include scanner 632C positioned inside system 600 (e.g., on an inner wall, in a ceiling, in a floor) between the first and second treatment chambers 602 and 604. In some embodiments, the scanner 632C can be configured to obtain information from containers positioned in either treatment chamber or both treatment chambers.

Figure 7:
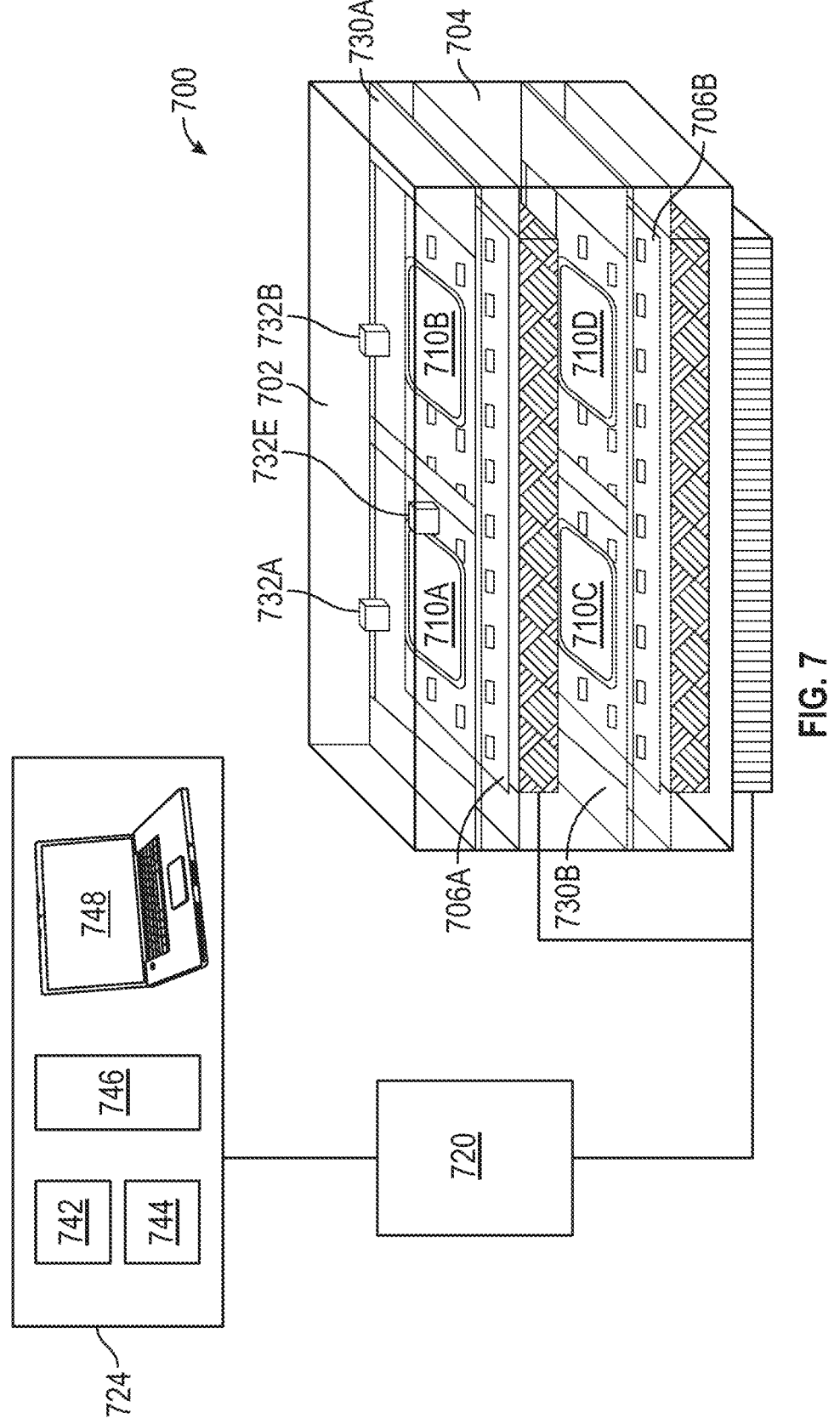
FIG. 7 illustrates a perspective view of an exemplary system for treating a biological fluid.

FIG. 7 is a perspective view of an exemplary system 700 for treating a biological fluid. In some embodiments, the system 700 is substantially similar to system 300, as illustrated in FIG. 3, and system 500, as illustrated in FIG. 5, differing in that the first treatment chamber 702 and the second treatment chamber 704 are positioned vertically (above and below each other) in system 700. Exemplary system 700 for treating biological fluids includes a first treatment chamber 702 and a second treatment chamber 704 for receiving one or more biological fluids 710, a first array of light sources 706 in each chamber positioned to illuminate from below one or more biological fluids 710, a platform 730 in each chamber configured to hold one or more biological fluids 710 (e.g., containers of biological fluids), and a sensor (e.g., scanner) 732 configured to obtain identifying information of a biological fluid loaded into the treatment chamber. Platform 730 carrying biological fluids 710 may be positioned above the light source array 706 with light source array 706 facing platform 730. However, in other embodiments, platform 730 carrying one or more biological fluids may be positioned below light source array 706 with light source array 706 facing the platform 730. Each of light source chambers 702 and 704 may further comprise a second array of light sources (not shown), positioned above and below the one or more biological fluids 710, such as for example similar to system 600, as illustrated in FIG. 6.

The system 700 can include scanners 732A and 732B positioned inside the first treatment chamber 702 (e.g., in the ceiling above compartments for biological fluids 710A and 710B) and two scanners similarly positioned inside the second treatment chamber 704 (e.g., in the ceiling above compartments for biological fluids 710C and 710D). Alternatively or in addition, the system 600 can include scanner 732E positioned at the exterior (e.g., exterior housing, exterior surface) of the system 600 between the first and second treatment chambers 702 and 704. In some embodiments, the scanner 732E can be configured to obtain information from containers positioned in either treatment chamber or both treatment chambers (e.g., when a platform in a drawer configuration is in an open position in the field of view of scanner 732E, when RFID tags are within the detection range of scanner 732E).

In some embodiments, any of the above described treatment systems may be used to treat (e.g., inactivate pathogen(s) in) one or more biological fluids, preferably biological fluids admixed with one or more pathogen inactivation compounds (e.g., photoactive pathogen inactivation compound, psoralen). In particular, any of the above described treatment systems may illuminate a mixture of one or more pathogen inactivation compounds and a biological fluid, such as for example, blood or a blood product (e.g., platelet compositions, plasma compositions and their derivatives, with light (e.g., ultraviolet light) of certain wavelengths to cause a photochemical reaction and inactivate pathogen(s), such as viruses, bacteria, parasites and other contaminants, such as for example, cell contaminants (e.g., leukocytes) that may be present in the biological fluid. In some embodiments, the pathogen inactivation compound targets nucleic acids to photochemically form adducts and/or cross-links. For example, a device of the present disclosure may be used in a method of treating a biological fluid comprising: providing a biological fluid in admixture with a photoactive pathogen inactivation compound (e.g., psoralen, amotosalen), and illuminating the biological fluid with ultraviolet light with a first peak wavelength of from about 315 nm to about 350 nm (e.g., about 315 nm to about 335 nm, about 330 nm to about 350 nm, about 340 nm to about 350 nm, about 340 nm, about 345 nm) emitted by a set of one or more first light sources, wherein illuminating the biological fluid occurs for a duration and at an intensity sufficient to inactivate a pathogen in the biological fluid. In some embodiments, each of the one or more first light sources emits light having a full-width half-maximum (FWHM) spectral bandwidth of less than 20 nanometers. In some embodiments, each of the one or more first light sources is a light-emitting diode (LED).

The term "pathogen inactivation compound" means any suitable compound, such as a small organic compound, that can be used to inactivate a pathogen that may be present in a biological fluid, such as for example, blood or a blood product. A pathogen inactivation compound that is a "photoactive" or "photoactivated" or "photochemical" or "photosensitizer" compound is a suitable compound that requires some level of light in order to sufficiently inactivate a pathogen. Such compounds are preferred in the inactivation of pathogens in biological products as they provide control over the inactivation process. In some embodiments, the pathogen inactivating compound is a photoactive pathogen inactivating compound selected from the group consisting of a psoralen, an isoalloxazine, an alloxazine, a phthalocyanine, a phenothiazine, a porphyrin, and merocyanine 540. In some embodiments, the pathogen inactivating compound is a psoralen. In some embodiments, the pathogen inactivating compound is amotosalen (e.g., S-59). Such photoactivated or photochemical pathogen inactivation compounds as described herein may include, but are not limited to, psoralens, isoalloxazines, alloxazines, phthalocyanines, phenothiazines, and porphyrins, where these terms are understood to encompass a general class of compounds, i.e. the core compound and suitable derivatives thereof. For example psoralens or a psoralen generally describes the psoralen core compound and any derivative thereof (e.g. amotosalen), isoalloxazines or an isoalloxazine generally describes the isoalloxazine core and any derivative thereof (e.g. riboflavin), and so forth. Such derivatives comprise the core compound structure as well as additional substituents on the core. Descriptions of such compounds include any salts thereof.

The term "amotosalen" means the compound 3-(2-aminoethoxymethyl)-2,5,9-trimethylfuro[3,2-g]chromen-7-one and any salts thereof. The compound may also be referred to as 4'-(4-amino-2-oxa)butyl-4,5',8-trimethyl psoralen. Where the methods of the present disclosure include adding amotosalen HCl (the HCl salt of amotosalen), the removal of this compound from the biological fluid, such as for example a blood product (e.g., platelet composition, unit of platelets, plasma composition, whole blood composition, plasma composition) is not limited to the removal of amotosalen HCl, as the amotosalen can be present in solution as other salts or as the free base. As used in the methods described herein, removal of amotosalen means removal of the compound in any form, e.g. as the free base or as any salt, as measured by the assays described herein.

In some embodiments, the pathogen inactivation compound is a 4-primaryamino-substituted psoralen, which is a psoralen compound having an $NH_2$ group linked to the 4'-position of the psoralen by a hydrocarbon chain having a total length of 2 to 20 carbons, where 0 to 6 of those carbons are independently replaced by NH or O, and each point of replacement is separated from each other point of replacement by at least two carbons, and is separated from the psoralen by at least one carbon. 4'-primaryamino-substituted psoralens may have additional substitutions on the 4, 5', and 8 positions of the psoralen, said substitutions include, but are not limited to, the following groups: H and $(CH_2)_nCH_3$, where n=0-6. In some embodiments, the 4'-primaryamino-substituted psoralen comprises: a) a substituent $R_1$ on the 4' carbon atom, selected from the group comprising: $-(CH_2)_u-NH_2$, $-(CH_2)_w-R_2-(CH_2)_z-NH_2$, $-(CH_2)_w-R_2-(CH_2)_x-R_3-(CH_2)_z-NH_2$, and $-(CH_2)_w-R_2-(CH_2)_x-R_3-(CH_2)_y-R_4-(CH_2)_z-NH_2$; wherein $R_2$, $R_3$, and $R_4$ are independently selected from the group comprising O and NH, in which u is a whole number from 1 to 10, w is a whole number from 1 to 5, x is a whole number from 2 to 5, y is a whole number from 2 to 5, and z is a whole number from 2 to 6; and b) substituents $R_5$, $R_6$, and $R_7$ on the 4, 5', and 8 carbon atoms respectively, independently selected from the group comprising H and $(CH_2)_vCH_3$, where v is a whole number from 0 to 5; or a salt thereof.

In some embodiments, the pathogen inactivation compound is a 5-primaryamino-substituted psoralen, which is a psoralen compound having an $NH_2$ group linked to the 5'-position of the psoralen by a hydrocarbon chain having a total length of 1 to 20 carbons, where 0 to 6 of those carbons are independently replaced by NH or O, and each point of replacement is separated from each other and point of replacement by at least two carbons, and is separated from the psoralen by at least one carbon. 5'-primaryamino-substituted psoralens may have additional substitutions on the 4, 4', and 8 positions of the psoralen, said substitutions include, but are not limited to, the following groups: H and $(CH_2)_nCH_3$, where n=0-6. In some embodiments, the 5'-primaryamino-substituted psoralen comprises: a) a substituent $R_1$ on the 5' carbon atom, selected from the group comprising: $-(CH_2)_u-NH_2$, $-(CH_2)_w-R_2-(CH_2)_z-NH_2$, $-(CH_2)_w-R_2-(CH_2)_x-R_3-(CH_2)_z-NH_2$, and $-(CH_2)_w-R_2-(CH_2)_x-R_3-(CH_2)_y-R_4-(CH_2)_z-NH_2$; wherein $R_2$, $R_3$, and $R_4$ are independently selected from the group comprising O and NH, and in which u is a whole number from 1 to 10, w is a whole number from 1 to 5, x is a whole number from 2 to 5, y is a whole number from 2 to 5, and z is a whole number from 2 to 6; and, b) substituents $R_5$, $R_6$, and $R_7$ on the 4, 4', and 8 carbon atoms respectively, independently selected from the group comprising H and $(CH_2)_vCH_3$, where v is a whole number from 0 to 5, where when $R_1$ is selected from the group comprising $-(CH_2)_u-NH_2$, $R_7$ is $(CH_2)_vCH_3$, and where when $R_5$, $R_6$, and $R_7$ are $(CH^2)_vCH_3$, u is a whole number from 3 to 10; or a salt thereof. Exemplary psoralen compounds are described, e.g., in U.S. Pat. No. 5,593,823.

In some embodiments, the biological fluid (e.g., platelet composition) is in admixture with a pathogen inactivation compound (PIC) in a platelet additive solution (PAS). In some embodiments, the PIC is admixed with the PAS prior to admixing with the biological fluid. Platelet additive solutions are known in the art, for example, as described by Alhumaidan et al. and Ringwald et al. (Alhumaidan, H. and Sweeney, J., *J Clin Apheresis*, 27:93-98 (2012); Ringwald et al., *Transfusion Medicine Reviews*, 20:158-64 (2006)), which are hereby incorporated by reference in their entirety. In some embodiments, the platelet additive solution (PAS) comprises one or more of chloride, acetate, citrate, potassium, magnesium, phosphate, gluconate, glucose, and bicarbonate. In some embodiments, the platelet additive solution (PAS) is a PAS approved by a regulatory agency or accrediting organization generally accepted in the field.

In some embodiments, the methods further comprise agitating the biological fluid. In some embodiments of any of the methods of the disclosure, a total dose of ultraviolet light illuminating the biological fluid (e.g., emitted by the one or more light sources, emitted by a set of one or more light sources, emitted by an array of light sources) is about 0.5 J/cm$^2$ to about 50 J/cm$^2$, such as any of about 0.5 J/cm$^2$ to about 10 J/cm$^2$, about 0.5 J/cm$^2$ to about 15 J/cm$^2$, about 0.5 J/cm$^2$ to about 25 J/cm$^2$, about 1 J/cm$^2$ to about 10 J/cm$^2$, about 1 J/cm$^2$ to about 15 J/cm$^2$, about 1 J/cm$^2$ to about 25 J/cm$^2$, about 3 J/cm$^2$ to about 10 J/cm$^2$, about 3 J/cm$^2$ to about 15 J/cm$^2$, about 3 J/cm$^2$ to about 25 J/cm$^2$, about 5 J/cm$^2$ to about 10 J/cm$^2$, about 5 J/cm$^2$ to about 15 J/cm$^2$, about 5 J/cm$^2$ to about 25 J/cm$^2$, about 10 J/cm$^2$ to about 30 J/cm$^2$, about 10 J/cm$^2$ to about 20 J/cm$^2$, about 15 J/cm$^2$ to about 50 J/cm$^2$, about 15 J/cm$^2$ to about 35 J/cm$^2$, about 20 J/cm$^2$ to about 30 J/cm$^2$, about 25 J/cm$^2$ to about 50 J/cm$^2$, about 30 J/cm$^2$ to about 40 J/cm$^2$, or about 40 J/cm$^2$ to about 50 J/cm$^2$. In some embodiments, the total dose of ultraviolet light illuminating the biological fluid is about 0.5 J/cm$^2$ or more, such as about any of 1 J/cm$^2$ or more, 2 J/cm$^2$ or more, 3 J/cm$^2$ or more, 4 J/cm$^2$ or more, 5 J/cm$^2$ or more, 6 J/cm$^2$ or more, 7 J/cm$^2$ or more, 8 J/cm$^2$ or more, 9 J/cm$^2$ or more, 10 J/cm$^2$ or more, 15 J/cm$^2$ or more, 20 J/cm$^2$ or more, 25 J/cm$^2$ or more, 30 J/cm$^2$ or more, 35 J/cm$^2$ or more, 40 J/cm$^2$ or more, 45 J/cm$^2$ or more, or more, or 50 J/cm$^2$ or more. In some embodiments, the total dose of ultraviolet light illuminating the biological fluid is less than about 50 J/cm$^2$, less than about 40 J/cm$^2$, less than about 30 J/cm$^2$, less than about 25 J/cm$^2$, less than about 20 J/cm$^2$, less than about 15 J/cm$^2$, or less than about 10 J/cm$^2$. In some embodiments, illuminating the biological fluid occurs for a duration and at an intensity sufficient to inactivate a pathogen in the biological fluid (e.g., if present in the biological fluid). For example, in some embodiments, illuminating the biological fluid occurs for a duration and at an intensity sufficient to provide a desired total dose (e.g., aforementioned total dose) of ultraviolet light illuminating the biological fluid (e.g., any suitable combination of duration and intensity sufficient to provide the total dose of ultraviolet light). In some embodiments, the intensity is between 1 and 1000 mW/cm$^2$ (e.g., between 1 and 100 mW/cm$^2$). In some embodiments, the duration is between 1 second and 2 hours (e.g., between 1 minute and 60 minutes).

It should be understood that treatment of a biological fluid to inactivate pathogen(s) that may be present does not necessarily inactivate completely all pathogens that may be present, but substantially reduces the amount of pathogens to significantly reduce the risk arising from the presence of a pathogen (e.g., infection associated with administration of a biological fluid contaminated with a pathogen, transfusion associated disease from a blood product, transfusion transmitted infection from a blood product). The inactivation of a pathogen may be assayed by measuring the number of infective pathogens (e.g., viral particles, bacteria) in a certain volume, and the level of inactivation is typically represented in the log reduction in the infectivity of the pathogen, or log reduction in titer. Methods of assaying log reduction in titer, and measurements thereof to assess levels of pathogen inactivation are well known in the art. In some embodiments, the systems, devices and/or methods for treating are sufficient to inactivate at least 1 log (e.g., at least 2 logs, at least 3 logs, at least 4 logs, or more) of a pathogen in the biological fluid when present. In some embodiments, the biological fluid after illuminating is suitable for infusion into a subject without further processing to remove residual pathogen inactivation compound or photoproduct(s) thereof. In some embodiments, the systems, devices and/or methods for treating are sufficient to inactivate at least 1 log (e.g., at least 2 logs, at least 3 logs, at least 4 logs, or more) of a pathogen in the biological fluid when present, and the biological fluid comprises 10 µM or less of a pathogen inactivation compound after illuminating the biological fluid. In some embodiments, the systems, devices and/or methods for treating are sufficient to inactivate at least 1 log (e.g., at least 2 logs, at least 3 logs, at least 4 logs, or more) of a pathogen in the biological fluid when present, and the biological fluid comprises 7.5 µM or less of the pathogen inactivation compound after illuminating. In some embodiments, the systems, devices and/or methods for treating are sufficient to inactivate at least 1 log (e.g., at least 2 logs, at least 3 logs, at least 4 logs, or more) of a pathogen in the biological fluid when present, and the biological fluid comprises 5 µM or less (e.g., 4 µM or less, 3 µM or less, 2 µM or less, 1 µM or less, 0.5 µM or less) of the pathogen inactivation compound after illuminating. In some embodiments, a concentration of the pathogen inactivation compound in admixture with the biological fluid prior to illuminating is at least about 10 µM (e.g., at least about 30 µM, at least about 60 µM, at least at least about 90 µM, at least about 110 µM). In some embodiments, a concentration of the pathogen inactivation compound in admixture with the biological fluid prior to illuminating is about 15 µM to about 150 µM (e.g., about 30 µM to about 110 µM, about 60 µM to about 90 µM, about 75 µM). In some embodiments, a concentration of the pathogen inactivation compound in admixture with the biological fluid after illuminating is at least 3-fold less than the concentration of pathogen inactivation compound in admixture with the biological fluid prior to illuminating. In some embodiments, the biological fluid after illuminating maintains sufficient biological activity so that the biological fluid is suitable for infusion into a subject.

Figure 8:
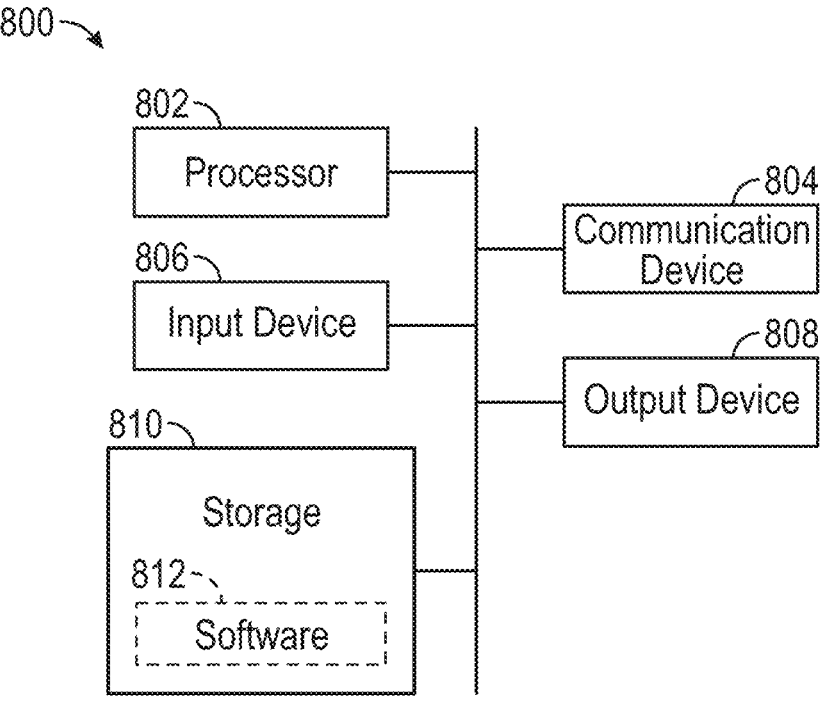
FIG. 8 is an example of a computing device in accordance with one embodiment of the disclosure.

FIG. 8 illustrates an example of a computing device in accordance with one embodiment. Device 800 can be a host computer connected to a network. Device 800 can be a client computer or a server. As shown in FIG. 8, device 800 can be any suitable type of microprocessor-based device, such as one of systems 100-700, computing system 524, a personal computer, workstation, server, or handheld computing device (portable electronic device) such as a phone or tablet. The device can include, for example, one or more of processor 802, input device 806, output device 808, storage 810, and communication device 804. Input device 806 and output device 808 can generally correspond to those described above and can either be connectable or integrated with the computer.

Input device 806 can be any suitable device that provides input, such as any of the display disclosed herein, a touchscreen, keyboard or keypad, mouse, or voice-recognition device. Output device 808 can be any suitable device that provides output, such as a touchscreen, haptics device, or speaker.

Storage 810 can be any suitable device that provides storage, such as an electrical, magnetic, or optical memory including a RAM, cache, hard drive, or removable storage disk. Communication device 804 can include any suitable device capable of transmitting and receiving signals over a network, such as a network interface chip or device. The components of the computer can be connected in any suitable manner, such as via a physical bus, or wirelessly.

Software 812, which can be stored in storage 810 and executed by processor 802, can include, for example, the programming that embodies the functionality of the present disclosure (e.g., as embodied in the devices described above).

Software 812 can also be stored and/or transported within any non-transitory, computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 840, that can contain or store programming for use by or in connection with an instruction-execution system, apparatus, or device.

Software 812 can also be propagated within any transport medium for use by or in connection with an instruction-execution system, apparatus, or device, such as those described above, that can fetch instructions associated with the software from the instruction-execution system, apparatus, or device and execute the instructions. In the context of this disclosure, a transport medium can be any medium that can communicate, propagate, or transport programming for use by or in connection with an instruction-execution system, apparatus, or device. The transport readable medium can include, but is not limited to, an electronic, magnetic, optical, electromagnetic, or infrared wired or wireless propagation medium.

Device 800 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Device 800 can implement any operating system suitable for operating on the network. Software 812 can be written in any suitable programming language, such as C, C++, Java, or Python. In various embodiments, application software embodying the functionality of the present disclosure can be deployed in different configurations, such as in a client/server arrangement or through a Web browser as a Web-based application or Web service, for example.

Figure 9A:
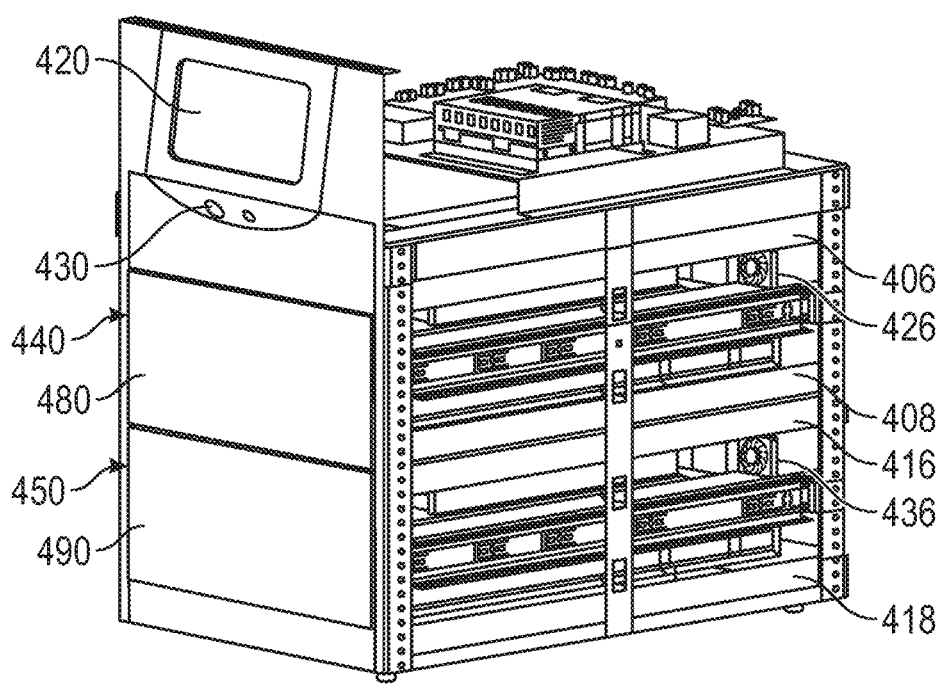
FIGS. 9A-9F illustrate exemplary systems for treating biological fluids.

FIG. 9A illustrates a perspective view of system 400, showing the exterior housing at the front and interior components from the side. Similar to FIG. 4J, this side view shows an upper stage including a display 420 (e.g., touchscreen) and control circuitry and/or a computer system, a first light source array 406 located above and facing the first platform 440 to illuminate a first biological fluid on first platform 440 in the first treatment, a second light source array 408 located below and facing the first platform 440 to illuminate the first biological fluid positioned on first platform 440, a third light source array 416 located above and facing the second platform 450 to illuminate a second biological fluid positioned on second platform 450 in the second treatment chamber, and a fourth light source array 418 located below and facing the second platform 450 to illuminate the second biological fluid positioned on the second platform 450. Similar to FIG. 4A, the exterior housing at the front shows display 420, scanner 430, and panels 480 and 490 of platforms 440 and 450 respectively, in a drawer configuration at a closed position. Also, FIG. 9A shows a fan 426 positioned in the rear of the first treatment chamber and a fan 436 positioned in the rear of the second treatment chamber.

Figure 9B:
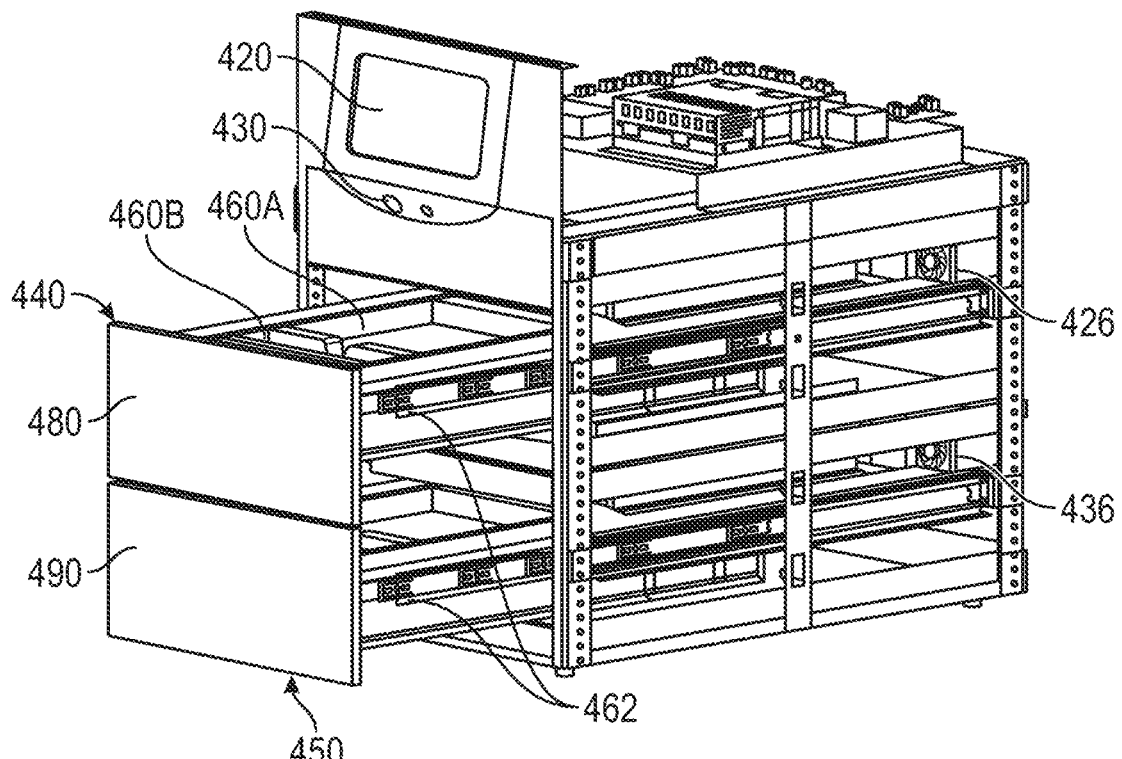

FIG. 9B illustrates a perspective view of system 400, showing the exterior housing at the front and interior components from the side. Similar to FIG. 9A, the exterior housing at the front shows display 420, scanner 430, and panels 480 and 490 of platforms 440 and 450 respectively, in a drawer configuration, but at an open position. Also shown are the inner regions of platforms 440 and 450 comprising compartments 460A and 460B, and the outer regions of platforms 440 and 450 slidably move via outer rails or tracks 462 into and out of a first (top) and second (bottom) treatment chamber, respectively.

Figure 9C:
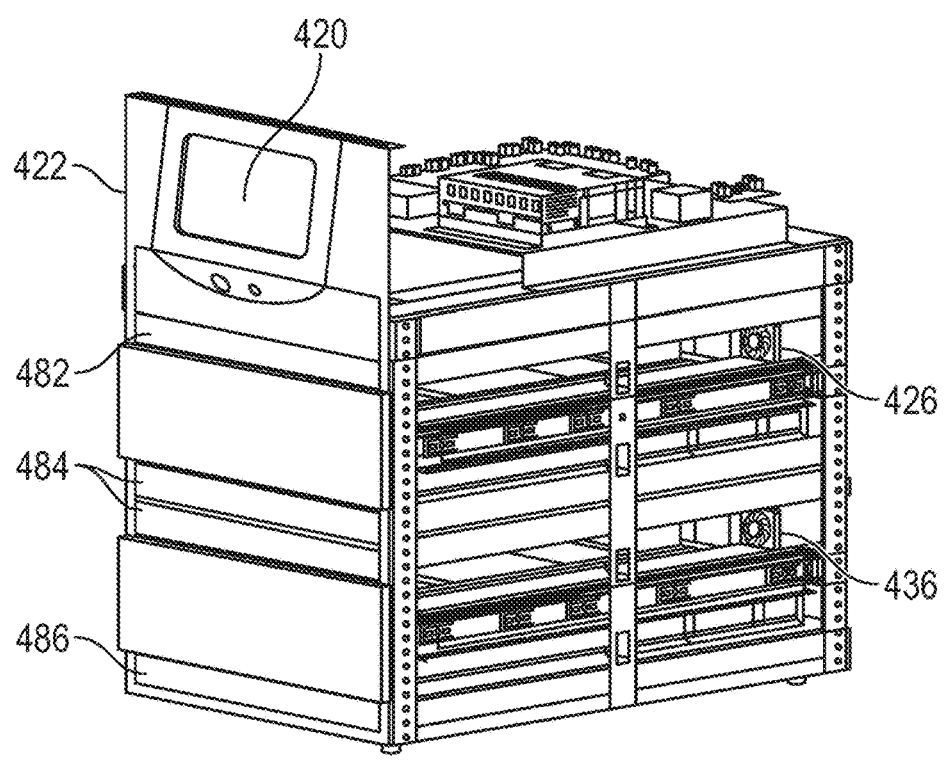
Figure 9D:
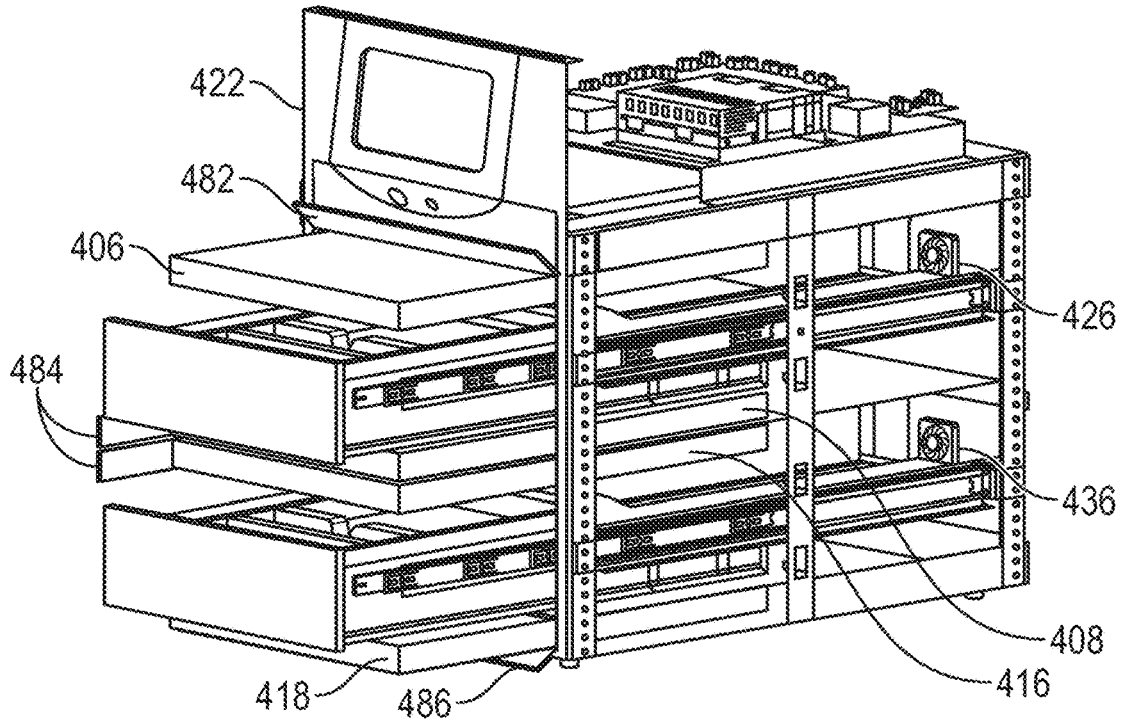
Figure 9E:
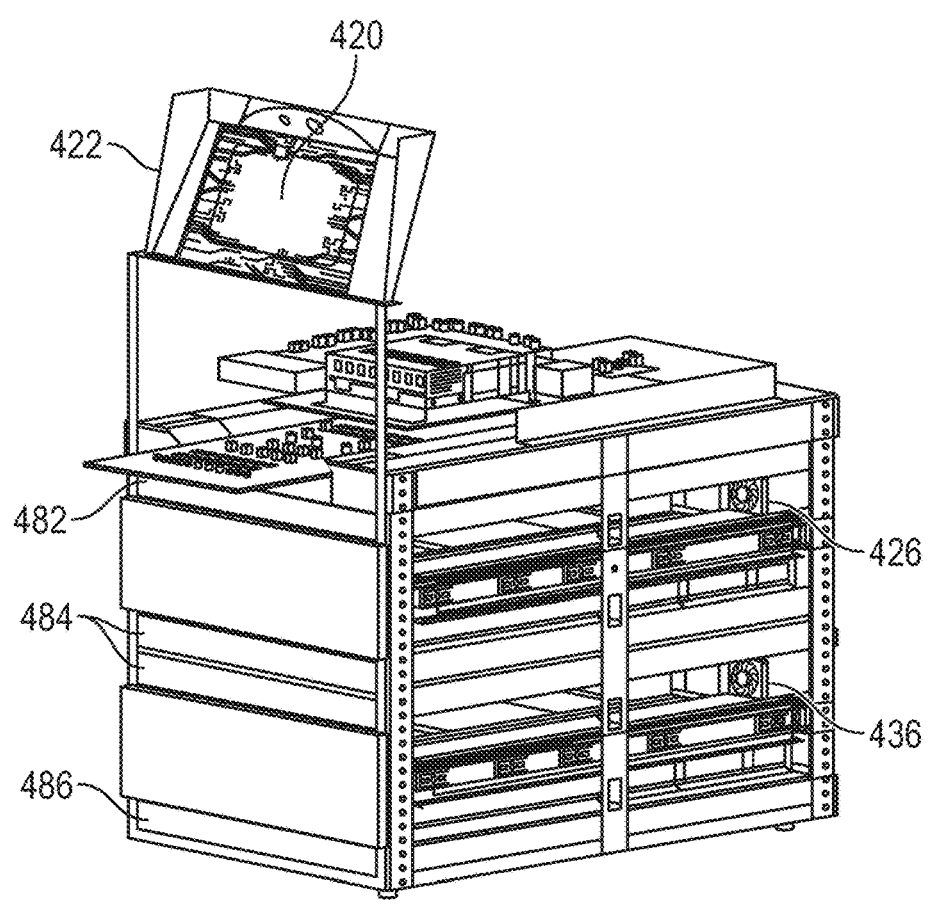

In some embodiments, system 400 may include one or more access panels through which maintenance or service personnel may access and then perform maintenance or service on internal components or structure of system 400. FIGS. 9C-9E illustrate exemplary access panels of system 400.

FIG. 9C illustrates a perspective view of system 400, showing the exterior housing at the front and interior components from the side. The exterior housing at the front shows four access panels in closed positions: a user interface access panel 422, a top access panel 482, a middle access panel 484, and a bottom access panel 486. The user interface access panel 422 is located at the level of the touchscreen 420 and includes the touchscreen 420 and adjacent housing areas. The top access panel 482 is located above a first panel of a first platform 440. The middle access panel 484 is located in between panels of first platform 440 and second platform 450. The bottom access panel 486 is located below a second panel of a second platform 450. In other examples, the single middle access panel may be replaced by two middle access panels. Also, FIG. 9C shows a fan 426 positioned in the rear of the first treatment chamber and a fan 436 positioned in the rear of the second treatment chamber.

FIG. 9D illustrates a perspective view of system 400, showing three of the four access panel in open positions. The user interface access panel 422 is still in a closed position. The top access panel 482 is flipped up into an open position, and a first light source array 406 can be slidably moved into or out of system 400 through the opening of the opened top access panel 482. The middle access panel 484 is opened toward the left into an open position, and a second light source array 408 and a third light source array 416 can be slidably moved into or out of system 400 through the opening of the opened middle access panel 484. The bottom access panel 484 is flipped down into an open position, and a fourth light source 418 array can be slidably moved into or out of system 400 through the opening of the opened bottom access panel 484. Through these three access panels, maintenance or service personnel may access and then perform maintenance or service on internal components or structure of system 400, like the four light source arrays 406, 408, 416, 418.

FIG. 9E illustrates a perspective view of system 400, showing one of the four access panel in an open position. The top access panel 482, the middle access panel 484, and the bottom access panel 486 are in closed positions. The user interface access panel 422 is flipped up into an open position, and components like the touchscreen 420 and control circuitry and/or a computer system are accessible. The rear of the touchscreen is accessible on the back side of the opened user interface access panel. Control circuitry and/or a computer system may be slidably moved into or out of system 400 through the opening of the opened user interface access panel 422. Exemplary control circuitry and/or a computer system may include one or more processors, an input device, an output device, storage, and/or a communication device. Through the user interface access panel 422, maintenance or service personnel may access and then perform maintenance or service on internal components or structure of system 400, like the touchscreen 420 and control circuitry and/or a computer system.

Figure 9F:
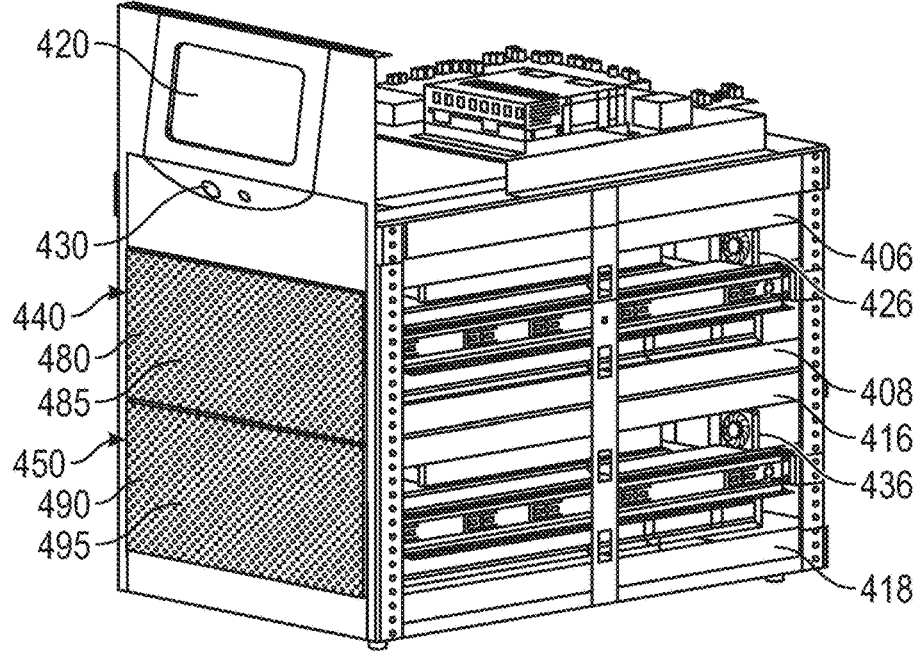

All of the embodiments shown in FIGS. 9A-9E may incorporate any or all of the air venting teachings discussed above in relation to FIG. 3B. For example, FIG. 9F illustrates the embodiment of FIG. 9A having panels with air venting 485 and 495. This air venting 485 and 495 can provide one or more air inlets and/or one or more air outlets, e.g., to provide cooling or heat dissipation or other temperature control functionality. Air can be drawn into system 400 and/or expelled out of system 400 by, e.g., the operation of a fan 426 positioned in the rear of the first treatment chamber and a fan 436 positioned in the rear of the second treatment chamber. In some embodiments, without or without air venting, a panel can be flush or substantially flush with adjacent structures (e.g., adjacent panel(s), adjacent frame of exterior housing, etc.), as illustrated in FIGS. 9A-9F.

All of the embodiments shown in FIGS. 9A-9F may incorporate any or all of the side access panel teachings discussed above in relation to FIG. 3B. The open side views shown in all of FIGS. 9A-9F may be the view that maintenance or service personnel see when one or more side access panels are open or removed.

Figure 10:
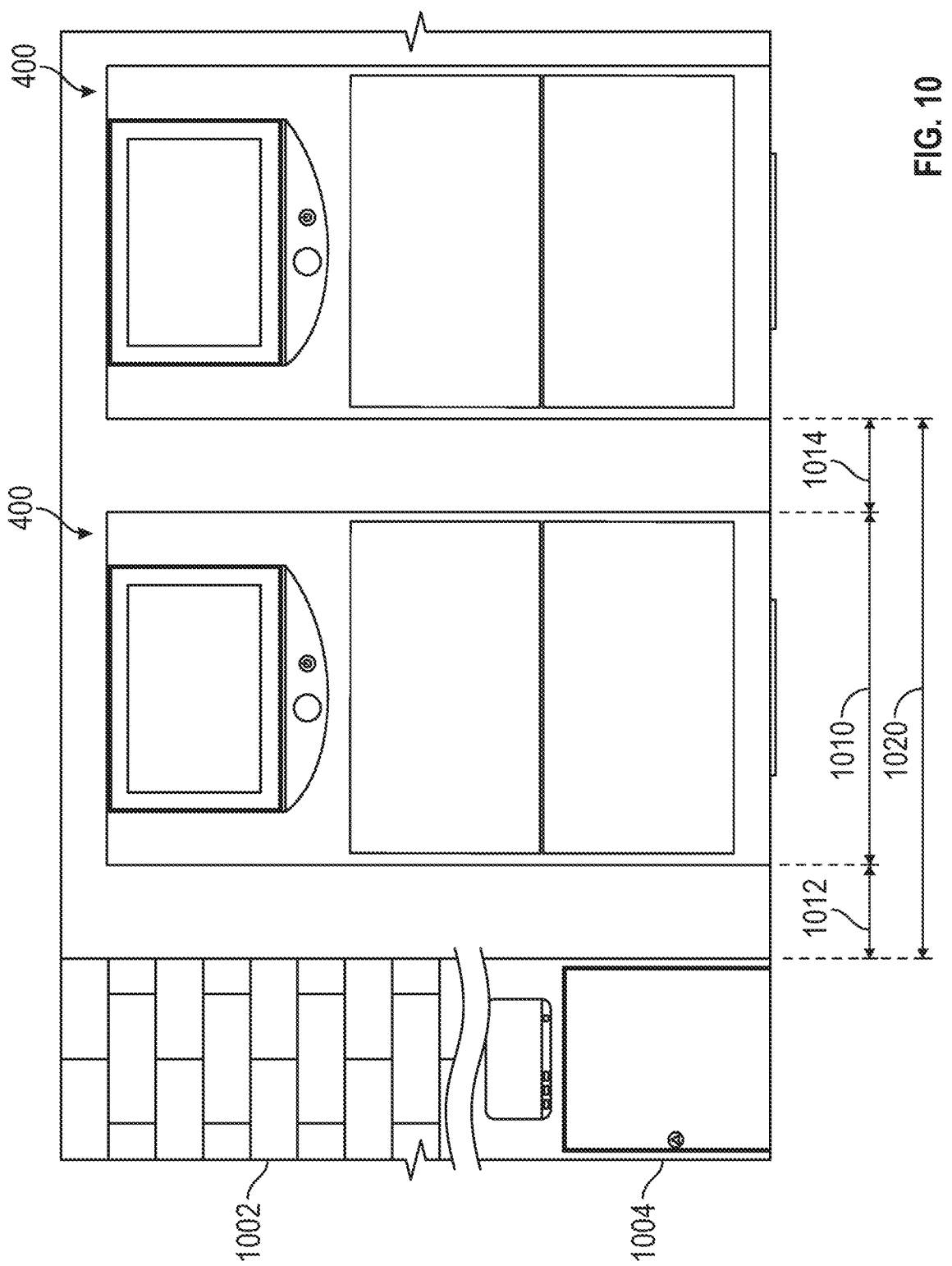
FIG. 10 illustrates adjacent exemplary systems for treating biological fluids.

FIG. 10 illustrates two adjacent systems 400, with one of the two systems 400 also adjacent to a wall 1002 or other equipment 1004. In some embodiments, the housing of each system may have a maximum horizontal width 1010 within a range of 30-60 cm at intervals of any widths. In some embodiments, the housing of each system may have a maximum horizontal width 1010 of 60 cm, 58 cm, 56 cm, 54 cm, 52 cm, 50 cm, 48 cm, or 46 cm. In some embodiments, the housing of each system may have a maximum horizontal width 1010 in a range of 30-45 cm. In some embodiments, the housing of each system may have a maximum horizontal width 1010 of 45 cm, 43 cm, 41 cm, 39 cm, 37 cm, 35 cm, 33 cm, or 31 cm. As the maximum horizontal width 1010 of the housing of each system decreases, the adjacent systems 400 may occupy a more compact space, which may allow a blood product processing facility to operate more systems and increase throughput treatment of biological fluids for a given amount of space in the facility.

For each system 400, the system may be configured (e.g., per manufacturer's operating instructions or documentation) to operate within a target (e.g., minimum) operating space 1020 such that there are empty spaces 1012, 1014 on both left and right sides of the housing of the system 400 (e.g., any target operating space including an operating space such that there are 20 cm or less on both left and right sides of the housing). An empty space, or minimum operating space, on the left and/or on the right may be 30 cm or less, 25 cm or less, 20 cm or less, 15 cm or less, 10 cm or less, or 5 cm or less, e.g., about 30 cm, about 25 cm, about 20 cm, about 15 cm, about 10 cm, about 5 cm, or about 0 cm. In some embodiments, there is no empty space (e.g., operating space) requirement on either side of the system. As the empty space between adjacent systems 400 decreases, the adjacent systems 400 may occupy a more compact space, which may allow a blood product processing facility to operate more systems and increase throughput treatment of biological fluids for a given amount of space in the facility. Previous illuminator systems may require significantly wider empty spaces (e.g., operating spaces) on either or both sides that the systems of the present disclosure, such as for example, because of the range of thermal radiation (e.g., air flow requirements) of each adjacent previous illuminator system. Outside of the thermal radiation range of a first previous illuminator system, an adjacent second previous illuminator system may operate properly without thermal radiation from the first previous illuminator system adversely increasing the temperature in the target operating of the adjacent second previous illuminator system.

Previous illuminator systems are generally horizontally wide and limited to treatment chambers of only one horizontal layer. Improved systems and methods disclosed herein may provide an illuminator system having multiple treatment chambers, that can be controlled and used for treatment processes independently from each other, and design features that may provide a variety of advantageous benefits. For example, due to the forward-backward agitation direction of the platforms of systems 400, it may be unnecessary for the system to have a wide housing that would be necessary to accommodate a left-right agitation direction. As another example, with a relatively more compact and narrow form factor, multiple (e.g., two, two and a half, three) whole systems 400 may fit in the operating space of a single previous illuminator system. As yet another example, due to the front-to-back direction or the back-to-front direction of fan airflow, it may be unnecessary to have lateral operating space on the left and/or right of system 400 that would accommodate a left-right directed airflow. Each of these examples provides an exemplary advantageous benefit over previous illuminator systems, but the improved systems and methods disclosed herein are not limited to these exemplary advantageous benefits but may provide further advantageous benefits in accordance with this disclosure.

The present disclosure provides a method of treating a biological fluid, comprising illuminating the biological fluid with any of the systems provided herein (e.g., aforementioned systems, systems disclosed hereafter), for a duration and at an intensity sufficient to inactivate a pathogen in the biological fluid (e.g., if present in the biological fluid). In some embodiments, the present disclosure provides a method of treating a biological fluid comprising: providing the biological fluid in admixture with a pathogen inactivation compound (e.g., photoactive pathogen inactivation compound, psoralen, amotosalen), and illuminating the biological fluid with any of the systems provided herein (e.g., aforementioned systems), for a duration and at an intensity sufficient to inactivate a pathogen in the biological fluid (e.g., if present in the biological fluid). In some embodiments, the biological fluid is illuminated with ultraviolet light (e.g., ultraviolet A, ultraviolet B, ultraviolet C, ultraviolet light with a first peak wavelength of from about 315 nm to about 350 nm) emitted by a set of one or more first light sources, wherein: 1) each of the one or more first light sources emits light having a full-width half-maximum (FWHM) spectral bandwidth of less than 20 nanometers, and/or 2) each of the one or more first light sources is a light-emitting diode (LED). In some embodiments, the biological fluid is illuminated with ultraviolet light emitted by a set of one or more first light sources with a first peak wavelength of from about 315 nm to about 350 nm. In some embodiments, the biological fluid is illuminated with ultraviolet light emitted by a set of one or more first light sources with a first peak wavelength from about 330 nm to about 350 nm. In some embodiments, the biological fluid is illuminated with ultraviolet light emitted by a set of one or more first light sources with a first peak wavelength of from about 340 nm to about 350 nm. In some embodiments, the biological fluid is illuminated with ultraviolet light emitted by a set of one or more first light sources with a first peak wavelength within a range of 345±5 nm. In some embodiments, the biological fluid is illuminated with ultraviolet light emitted by a set of one or more first light sources with a first peak wavelength of from about 315 nm to about 335 nm. In some embodiments, the biological fluid is illuminated with ultraviolet light emitted by a set of one or more first light sources with a first peak wavelength and ultraviolet light from a set of one or more second light sources with a second peak wavelength, wherein the second peak wavelength differs from the first peak wavelength by at least 5 nanometers. In some embodiments, the duration and intensity of illuminating provides a total dose of ultraviolet light illuminating the biological fluid of about 0.5 J/cm$^2$ or more (e.g., about 0.5 J/cm$^2$ to about 50 J/cm$^2$). In some embodiments, the intensity is between 1 and 1000 mW/cm$^2$ (e.g., between 1 and 100 mW/cm$^2$). In some embodiments, the duration is between 1 second and 2 hours (e.g., between 1 minute and 60 minutes). In some embodiments, the method of treating a biological fluid is sufficient to inactivate at least 1 log of a pathogen in the biological fluid. In some embodiments, the method of treating a biological fluid is sufficient to inactivate at least 4 logs of a pathogen in the biological fluid. In some embodiments, the biological fluid is a blood product (e.g., platelets, plasma).

Treatment of a biological fluid with a psoralen pathogen inactivation compound and illumination with a system of the present disclosure was performed. More specifically, photochemical inactivation of both virus and bacteria was performed with the psoralen amotosalen (S-59) and ultraviolet light illumination with a system of the present disclosure that incorporated arrays of ultraviolet A LEDs emitting peak wavelengths of 346-349 nm. For studies evaluating the inactivation of virus, platelets in platelet additive solution (PAS) were spiked with a stock of vesicular stomatitis virus (VSV) and processed with the commercially available INTERCEPT® Blood System large volume (LV) sets and small volume (SV) sets (Cerus Corp., Concord, CA), with 150 μM amotosalen (nominal concentration). For the platelets in LV sets, VSV spiked platelet preparations of 335 mL were processed in triplicate and subjected to illumination with 3.9 J/cm$^2$. For the platelets in SV sets, VSV spiked platelet preparations of 285 mL were processed in triplicate and subjected to illumination with 3.6 J/cm$^2$. Samples were collected both pre- and post-illumination to determine titers of VSV and log inactivation of the virus, as well as S-59 concentration pre-illumination and post-illumination to calculate photoconversion and percent residual amotosalen post-illumination. Data are shown in the following Table 1 and demonstrate 4.0±0.5 and 4.5±0.3 log inactivation of VSV in platelets/PAS using the LV and SV sets, respectively. Additionally, percent residual S-59 was shown to be 16.5±1.2 and 14.3±4.6 for platelets/PAS in the LV and SV sets, respectively (calculated from pre- and post-illumination data).

For studies evaluating the inactivation of bacteria in different blood products, either plasma, or platelets in platelet additive solution (PAS), were spiked with a stock of *Klebsiella pneumoniae* and processed with the commercially available INTERCEPT® Blood System plasma or platelet LV sets, respectively, with 150 μM amotosalen (nominal concentration). For the plasma, *K. pneumoniae* spiked plasma preparations were processed in triplicate in INTERCEPT® plasma sets and subjected to illumination with 6.4 J/cm$^2$. For the platelets, *K. pneumoniae* spiked platelet preparations were processed in triplicate in INTERCEPT® platelet LV sets and subjected to illumination with 3.9 J/cm$^2$. Samples were collected both pre- and post-illumination to determine titers of *K. pneumoniae* and log inactivation of the bacteria, as well as S-59 concentration pre-illumination and post-illumination to calculate photo-conversion and percent residual amotosalen post-illumination. Data are shown in the following Table 1 and demonstrate 6.3±0.3 and 7.2±0.2 log inactivation of *K. pneumoniae* in plasma and in platelets/PAS, respectively. Additionally, percent residual S-59 was shown to be 55.8±3.6 and 15.2±1.7 for the plasma samples and for the platelets/PAS, respectively (calculated from pre- and post-illumination data).

TABLE 1

| Pathogen inactivation of VSV and *K. pneumoniae* | | | | | |
|---|---|---|---|---|---|
| Sample | Illumi-nation | Input Titer (Log PFU/mL) | Log Inacti-vation | S-59 (μM) Pre-illum. | S-59 (μM) Post-illum. |
| VSV: | | | | | |
| Platelets/ PAS (LV Set) | 3.9 J/cm² | 6.8 ± 0.6 | 4.0 ± 0.5 | 147.6 ± 0.9 | 24.3 ± 1.9 |
| Platelets/ PAS (SV Set) | 3.6 J/cm² | 6.5 ± 0.4 | 4.5 ± 0.3 | 142.2 ± 0.4 | 20.3 ± 6.5 |
| *K. pneumo.*: | | | | | |
| Plasma | 6.4 J/cm² | 7.8 ± 0.0 | 6.3 ± 0.3 | 138.2 ± 4.2 | 77.0 ± 2.5 |
| Platelets/ PAS (LV Set) | 3.9 J/cm² | 7.7 ± 0.2 | 7.2 ± 0.2 | 149.1 ± 0.6 | 22.6 ± 2.6 |

While specific components, configurations, features, and functions are provided above, it will be appreciated by one of ordinary skill in the art that other variations may be used. Additionally, although a feature may appear to be described in connection with a particular embodiment, one skilled in the art would recognize that various features of the described embodiments may be combined. Moreover, aspects described in connection with an embodiment may stand alone.

Although embodiments have been fully described with reference to the accompanying drawings, it should be noted that various changes and modifications will be apparent to those skilled in the art. Such changes and modifications are to be understood as being included within the scope of the various embodiments as defined by the appended claims.

Variations of the embodiments provided herein may become apparent to those working in the art upon reading the foregoing description. It is expected that skilled artisans will be able to employ such variations as appropriate, and the practice of the systems, methods, and apparatuses described herein otherwise than as specifically described herein. Accordingly, the systems, methods, and apparatuses described herein include all modifications and equivalents of the subject matter recited in the claims appended hereto as permitted by applicable law. Moreover, any combination of the above-described elements in all possible variations thereof is encompassed by the description unless otherwise indicated herein or otherwise clearly contradicted by context.

In one aspect, a biological fluid treatment system comprises: a first treatment chamber configured to receive a first biological fluid; a second treatment chamber configured to receive a second biological fluid; a first platform configured to carry the first biological fluid and to be positioned in the first treatment chamber; a second platform configured to carry the second biological fluid and to be positioned in the second treatment chamber; a first array of light sources positioned to illuminate the first biological fluid in the first treatment chamber and a second array of light sources positioned to illuminate the second biological fluid in the second treatment chamber; a display; one or more processors; and a memory including instructions, which when executed by the one or more processors, cause the one or more processors to perform a method comprising providing for display, on the display, a graphical user interface (GUI) including a plurality of GUI objects associated with treatment of the first biological fluid by illumination from the first array of light sources or associated with treatment of the second biological fluid by illumination from the second array of light sources.

In some aspects of the above system, the first array of light sources and the second array of light sources are configured to illuminate the first biological fluid and the second biological fluid, respectively, with ultraviolet light. In some aspects of the each of the above systems, each of the arrays of light sources comprises a respective first light source channel configured to emit ultraviolet light with a first peak wavelength of the array of from about 315 nm to about 350 nm. In some aspects of the each of the above systems, each of the arrays of light sources comprises a respective first light source channel configured to emit ultraviolet light with a first peak wavelength of the array of from about 330 nm to about 350 nm. In some aspects of the each of the above systems, each of the arrays of light sources comprises a respective first light source channel configured to emit ultraviolet light with a first peak wavelength of the array of from about 340 nm to about 350 nm. In some aspects of the each of the above systems, each of the arrays of light sources comprises a respective first light source channel configured to emit ultraviolet light with a first peak wavelength of the array within a range of 345±5 nm. In some aspects of the each of the above systems, each of the arrays of light sources comprises a respective first light source channel configured to emit ultraviolet light with a first peak wavelength of the array of from about 315 nm to about 335 nm.

In some aspects of the each of the above systems, for each of the arrays of light sources, the respective first light source channel comprises one or more light sources, each of which emits light having a full-width half-maximum (FWHM) spectral bandwidth of less than 20 nanometers.

In some aspects of the each of the above systems, the system further comprises: a third array of light sources facing an opposite direction as the first array of light sources and positioned to illuminate the first biological fluid in the first treatment chamber, and; a fourth array of light sources facing an opposite direction as the second array of light sources and positioned to illuminate the second biological fluid in the second treatment chamber; wherein the method further comprises providing for display, on the display, a graphical user interface (GUI) including a plurality of GUI objects associated with treatment of the first biological fluid by illumination from the third array of light sources or associated with treatment of the second biological fluid by illumination from the fourth array of light sources.

In some aspects of the each of the above systems, each of the third and fourth arrays of light sources comprises a respective first light source channel configured to emit ultraviolet light with a first peak wavelength of the array of from about 315 nm to about 350 nm. In some aspects of the each of the above systems, each of the third and fourth arrays of light sources comprises a respective first light source channel configured to emit ultraviolet light with a first peak wavelength of the array of from about 330 nm to about 350 nm. In some aspects of the each of the above systems, each of the third and fourth arrays of light sources comprises a respective first light source channel configured to emit ultraviolet light with a first peak wavelength of the array of from about 340 nm to about 350 nm. In some aspects of the each of the above systems, each of the third and fourth arrays of light sources comprises a respective first light source channel configured to emit ultraviolet light with a first peak wavelength of the array within a range of 345±5 nm. In some aspects of the each of the above systems, each of the third and fourth arrays of light sources comprises a respective first light source channel configured to emit ultraviolet light with a first peak wavelength of the array of from about 315 nm to about 335 nm.

In some aspects of the each of the above systems, for each of the third and fourth arrays of light sources, the respective first light source channel comprises one or more light sources, each of which emits light having a full-width half-maximum (FWHM) spectral bandwidth of less than 20 nanometers.

In some aspects of the each of the above systems, each of the arrays of light sources comprises one or more light sources, each of which is a light-emitting diode, and wherein, for each of the arrays of light sources, the respective ultraviolet light is emitted by the respective one or more light sources.

In some aspects of the each of the above systems, the first platform is slideably moveable for introducing and removing the first biological fluid into and out of the first treatment chamber and the second platform is slideably moveable for introducing and removing the second biological fluid into and out of the second treatment chamber.

In some aspects of the each of the above systems, the system further comprises a housing configured to enclose the first treatment chamber, the second treatment chamber, the first platform, the second platform, the first array of light sources, the second array of light sources, the display, the one or more processors, and the memory.

In some aspects of the each of the above systems, the system further comprises a scanner configured to obtain identifying information associated with the first biological fluid, the second biological fluid, or both the first biological fluid and the second biological fluid. In some aspects of the each of the above systems, the scanner is one of the group comprising a barcode scanner, QR code scanner, and a RFID scanner. In some aspects of the each of the above systems, the identifying information is in a visible form of a barcode or a QR code on a container for containing the first biological fluid or the second biological fluid or on at least one of one or more containers of a multi-container assembly for containing the first biological fluid or the second biological fluid, and the method further comprises obtaining, by the scanner, the barcode or the QR code on the container for containing the first biological fluid or the second biological fluid or on the at least one of the one or more containers of the multi-container assembly. In some aspects of the each of the above systems, the scanner is configured to obtain the identifying information in a visible form on a container for containing the first biological fluid or the second biological fluid when the container for containing the first biological fluid or the second biological fluid is positioned on the first platform or the second platform or on at least one of the one or more containers of a multi-container assembly for containing the first biological fluid or the second biological fluid when the one or more containers of the multi-container assembly is positioned on the first platform or the second platform. In some aspects of the each of the above systems, the identifying information is multiple sets of identifying information in a visible form on a container for containing the first biological fluid or the second biological fluid or on one or more containers of a multi-container assembly for containing the first biological fluid or the second biological fluid or conveyed in a transmittable form from tags on the container for containing the first biological fluid or the second biological fluid or on the one or more containers of the multi-container assembly for containing the first biological fluid or the second biological fluid, and the scanner is a multi-scan scanner configured to obtain the multiple sets of identifying information in a multi-scan operation. In some aspects of the each of the above systems, wherein the scanner is integrated or embedded in a fixed position in the housing and coupled to the one or more processors. In some aspects of the each of the above systems, the scanner is located inside the first treatment chamber, the second treatment chamber, or both the first and the second treatment chambers. In some aspects of the each of the above systems, the scanner is located at a first opening of the first treatment chamber or at a second opening of the second treatment chamber. In some aspects of the each of the above systems, the scanner is located external to the first treatment chamber and the second treatment chamber. In some aspects of the each of the above systems, the scanner is a handheld scanner that is wirelessly coupled to the one or more processors. In some aspects of the each of the above systems, the scanner is a handheld scanner that is coupled to the one or more processors by wired connection.

In some aspects of the each of the above systems, the first treatment chamber and the second treatment chamber are arranged horizontally such that the first biological fluid and the second biological fluid, when positioned on the first platform and on the second platform, respectively, are within a same plane. In some aspects of the each of the above systems, the first treatment chamber and the second treatment chamber are arranged vertically such that the first biological fluid and the second biological fluid, when positioned on the first platform and on the second platform, respectively, are in parallel planes.

In some aspects of the each of the above systems, the system further comprises a first panel movable between a closed position and an open position, wherein the first panel covers a first opening to the first treatment chamber in the closed position, wherein the first panel uncovers the first opening to the first treatment chamber in the open position, wherein an exterior of the first panel includes one or more of the group comprising a protruding handle and a recess handle. In some aspects of the each of the above systems, the system further comprises a first panel movable between a closed position and an open position, wherein the first panel covers a first opening to the first treatment chamber in the closed position, wherein the first panel uncovers the first opening to the first treatment chamber in the open position, wherein the entire exterior of the first panel lacks any handle. In some aspects of the each of the above systems, the first panel is configured to be locked to remain in the closed position, and configured to be unlocked in response to an input.

In some aspects of the each of the above systems, the first platform comprises the first panel. In some aspects of the each of the above systems, the first platform comprises: an outer region comprising: the first panel movable between a closed position and an open position, the outer region configured to remain in a fixed position when the first panel is in the closed position, and first support structure; and an inner region configured to move to agitate the first biological fluid during a time period in which the outer region is in a fixed position, wherein the first support structure of the outer region structurally supports the inner region. In some aspects of the each of the above systems, the first platform comprises: an outer region comprising: the first panel movable between a closed position and an open position, the outer region configured to remain in a fixed position when the first panel is in the closed position, and first support structure; and an inner region configured to move to agitate the first biological fluid during a time period in which the outer region is in a fixed position, wherein the first support structure of the outer region structurally supports the inner region.

In some aspects of the each of the above systems, the outer region comprises a motor configured to generate motion, wherein the inner region is configured to agitate the first biological fluid based on the motion generated by the motor. In some aspects of the each of the above systems, the system is configured to control (e.g., adjustably control) one or more aspects of the movement of the inner region to agitate the first biological fluid, such as offset, speed, acceleration, and deceleration. In some aspects of the each of the above systems, the motor is located at a position on the right or on the left of where the first biological fluid is to be carried by the first platform. In some aspects of the each of the above systems, the motor is located at a position in front of or to the rear of where the first biological fluid is to be carried by the first platform.

In some aspects of the each of the above systems, the second platform comprises: a second panel movable between a closed position and an open position, wherein the second panel covers a second opening to the second treatment chamber in the closed position, wherein the second panel uncovers the second opening to the second treatment chamber in the open position; an outer region comprising: the second panel movable between a closed position and an open position, the outer region configured to remain in a fixed position when the second panel is in the closed position, second support structure; and an inner region configured to move to agitate the second biological fluid during a time period in which the outer region is in a fixed position, wherein the second support structure of the output region structurally supports the inner region.

In some aspects of the each of the above systems, the first platform and second platform each comprises a first compartment and a second compartment, the first and second compartments configured to carry a multi-container assembly containing the biological fluid of a respective platform, wherein the first compartment of the first platform is configured to carry a first container of a first multi-container assembly, the first container containing the first biological fluid, and wherein the first compartment is positioned such that the first array of light sources is configured to illuminate the first container when the first platform is positioned in the first treatment chamber; wherein the second compartment of the first platform is configured to carry one or more additional containers of the first multi-container assembly, the one or more additional containers not containing the first biological fluid, and wherein the second compartment is positioned such that the first array of light sources is not configured to illuminate the one or more additional containers when the first platform is positioned in the first treatment chamber; wherein the first compartment of the second platform is configured to carry a first container of a second multi-container assembly, the first container containing the second biological fluid, and wherein the first compartment is positioned such that the second array of light sources is configured to illuminate the first container when the second platform is positioned in the second treatment chamber; and wherein the second compartment of the second platform is configured to carry one or more additional containers of the second multi-container assembly, the one or more additional containers not containing the second biological fluid, and wherein the second compartment is positioned such that the second array of light sources is not configured to illuminate the one or more additional containers when the second platform is positioned in the second treatment chamber.

In some aspects of the each of the above systems, the display is a touchscreen configured to display the GUI including the plurality of GUI objects, and the GUI objects are responsive to touch inputs on the touchscreen. In some aspects of the each of the above systems, the method further comprises: receiving an input associated with a selection of a GUI object; and in response to receiving the input, performing a biological fluid treatment operation.

In some aspects of the each of the above systems, any of the systems provided herein (e.g., aforementioned systems) may perform a method of treating one or more biological fluids comprising: illuminating a first biological fluid of the one or more biological fluids with ultraviolet light (e.g., ultraviolet light with a first peak wavelength of from about 315 nm to about 350 nm) emitted by a set of one or more first light sources, wherein the first biological fluid is admixed with a pathogen inactivation compound (e.g., photoactive pathogen inactivation compound, psoralen, amotosalen), wherein: 1) each of the one or more first light sources emits light having a full-width half-maximum (FWHM) spectral bandwidth of less than 20 nanometers, and/or 2) each of the one or more first light sources is a light-emitting diode (LED); and wherein illuminating the first biological fluid occurs for a duration and at an intensity sufficient to inactivate a pathogen in the first biological fluid. In some aspects of the each of the above systems, the method of treating the one or more biological fluids may further comprise: illuminating a second biological fluid of the one or more biological fluids with ultraviolet light (e.g., ultraviolet light with a second peak wavelength of from about 315 nm to about 350 nm) emitted by a set of one or more second light sources, wherein the second biological fluid is admixed with a pathogen inactivation compound (e.g., photoactive pathogen inactivation compound, psoralen, amotosalen), wherein: 1) each of the one or more second light sources emits light having a full-width half-maximum (FWHM) spectral bandwidth of less than 20 nanometers, and/or 2) each of the one or more second light sources is a light-emitting diode (LED); and wherein illuminating the second biological fluid occurs for a duration and at an intensity sufficient to inactivate a pathogen in the second biological fluid.

In some aspects of the each of the above systems, each of the first platform and the second platform is configured to carry the first and second biological fluids respectively in a first flexible container and a second flexible container respectively, each with a volume capacity up to about 3000 mL (e.g., volume capacity of 3000 mL or less), up to about 2500 mL, up to about 2000 ml, up to about 1500 mL, up to about 1200 mL, up to about 1000 mL, or up to about 800 mL.

In some aspects of the each of the above systems, the system comprises a heating and/or a cooling unit configured to adjust or set a temperature of the first treatment chamber, wherein the method further comprises: controlling the heating/cooling unit to maintain the temperature of the first biological fluid within 2° C. during treatment of the first biological fluid by illumination from the first array of light sources. In some aspects of the each of the above systems, the method further comprises: controlling the system to maintain the temperature of the first biological fluid within 2° C. during treatment of the first biological fluid by illumination from the first array of light sources.

In some aspects of the each of the above systems, the housing has a maximum horizontal width within a range of 30-45 cm. In some aspects of the each of the above systems, the system is configured to operate within a target operating space such that there are empty spaces of 20 cm or less on both left and right sides of the housing.

In some aspects of the each of the above systems, the system further comprises one or more front access panels configured to provide access to one or more of the first array of light sources, the second array of light sources, and the one or more processors.

In another aspect, the present disclosure provides a method of treating a biological fluid comprising: providing a biological fluid in admixture with a pathogen inactivation compound (e.g., photoactive pathogen inactivation compound, psoralen, amotosalen), and illuminating the biological fluid with any of the systems provided herein (e.g., aforementioned systems), for a duration and at an intensity sufficient to inactivate a pathogen in the biological fluid. In some aspects of the each of the above systems, the biological fluid is illuminated with ultraviolet light (e.g., ultraviolet light with a first peak wavelength of from about 315 nm to about 350 nm) emitted by a set of one or more first light sources, wherein: 1) each of the one or more first light sources emits light having a full-width half-maximum (FWHM) spectral bandwidth of less than 20 nanometers, and/or 2) each of the one or more first light sources is a light-emitting diode (LED). In some embodiments, the method of treating a biological fluid is sufficient to inactivate at least 1 log of a pathogen in the biological fluid. In some embodiments, the method of treating a biological fluid is sufficient to inactivate at least 4 logs of a pathogen in the biological fluid.

The invention claimed is:

1. A platform for use in a biological fluid treatment system, the platform comprising:
  an inner region configured to carry a biological fluid for treatment by the biological fluid treatment system, the inner region configured to move to agitate the biological fluid
  wherein the inner region comprises an inner region assembly, the inner region assembly comprising one or more removable portions configured to carry the biological fluid and a cradle portion for receiving the one or more removable portions,
  wherein the one or more removable portions comprise a tray;
  an outer region comprising a support structure, the outer region configured to remain in a fixed position during a time period in which the inner region moves to agitate the biological fluid; and
  a panel, wherein the panel is configured to move between a closed position and an open position;
  wherein, in the closed position:
    the panel covers an opening to a treatment chamber of the biological fluid treatment system, and
    the biological fluid is positioned in the treatment chamber;
  wherein, in the open position, the panel uncovers the opening to the treatment chamber of the biological fluid treatment system.

2. The platform of claim 1, wherein the panel is attached to the outer region of the platform.

3. The platform of claim 1, wherein the support structure of the outer region structurally supports the inner region of the platform.

4. The platform of claim 1, wherein the support structure of the outer region comprises inner rails or tracks that structurally support the inner region of the platform.

5. The platform of claim 1, wherein the outer region supports the cradle.

6. The platform of claim 1, wherein the cradle is mounted to or in inner rails or tracks of the outer region of the platform.

7. The platform of claim 1, wherein the biological treatment system comprises a sensor for determining a position of the cradle and/or whether a removable inner region portion is in the cradle.

8. The platform of claim 1, wherein the one or more removable portions comprise a rear compartment configured to carry a container containing the biological fluid in a position for illumination of the biological fluid.

9. The platform of claim 8, wherein the rear compartment comprises a compartment floor of material that is transparent or partially transparent to light emitted by light sources of the biological fluid treatment system.

10. The platform of claim 1, wherein the outer region comprises outer rails or tracks, the outer region configured to slidably move into and out of the treatment chamber via the outer rails or tracks.

11. The platform of claim 1, wherein the panel comprises a protruding handle or a recessed handle configured to allow the panel and the platform to be manually moved between the closed position and the open position.

12. The platform of claim 1, wherein an entire exterior of the panel lacks any handle.

13. The platform of claim 12, wherein the panel is configured to be opened when a force opposite to an opening direction is applied to the exterior of the panel.

14. The platform of claim 12, wherein the panel is configured to be opened using mechanical components to actuate the panel.

15. The platform of claim 12, wherein the panel is configured to be opened by a spring mechanism.

16. The platform of claim 1, wherein the panel is configured to open when the treatment of the biological fluid is starting or is complete.

17. The platform of claim 1, wherein the panel is configured to open for loading or unloading the biological fluid.

18. The platform of claim 1, wherein the biological treatment system comprises one or more sensors for determining a position of the platform, whether the platform is in a closed position, the presence of a biological fluid, and/or whether the platform is locked or latched.

19. The platform of claim 1, further comprising one or more motors or servos configured to move to agitate the biological fluid.

20. The platform of claim 19, wherein the outer region of the platform comprises the one or more motors or servos.

21. The platform of claim 19, wherein the one or more motors or servos are mounted to or on the platform.

22. The platform of claim 19, wherein the one or more motors or servos are located at a position in front of where the biological fluid is to be carried by the platform, between the panel and where the biological fluid is to be carried by the platform, to the rear of where the biological fluid is to be carried by the platform, or on the left or right of a where the biological fluid is to be carried by the platform.

23. The platform of claim 19, further comprising electrical wiring for powering and/or controlling the one or more motors or servos, wherein the electrical wiring is located inside or along the outer region.

24. The platform of claim 1, wherein movement of the inner region to agitate the biological fluid is forward and backward.

25. The platform of claim 1, wherein the panel further comprises air venting.

26. The platform of claim 25, wherein the air venting is configured to provide one or more air inlets for drawing air into the biological fluid treatment system, or the air venting is configured to provide one or more air outlets for expelling air out of the biological fluid treatment system.

27. The platform of claim 25, wherein the air venting comprises vent holes.

28. The platform of claim 25, wherein the air venting occupies all of the area of the panel, a fraction of the area of the panel, distinct horizontal venting strips, distinct vertical venting strips, circular or oval venting strips, rectangular or square venting strips, polygon venting strips, or a combination thereof.

29. The platform of claim 1, wherein the panel further comprises a filter compartment.

30. The platform of claim 29, wherein the filter compartment comprises an air filter for filtering incoming air.

31. The platform of claim 1, wherein the bottom of the platform is transparent or partially transparent to light used for the treatment of the biological fluid.

32. The platform of claim 31, wherein the transparency is greater than 95% transparent, greater than 90% transparent, or greater than 80% transparent to light used for the treatment of the biological fluid.

33. The platform of claim 31, wherein the light is ultraviolet light.

34. The platform of claim 1, wherein, when in the closed position, edges of the panel are flush or substantially flush with an adjacent structure.

35. A method for using a biological fluid treatment system, the method comprising:

using a platform of claim 1, the biological fluid treatment system comprising the platform; and treating a biological fluid using the biological fluid treatment system.

\*  \*  \*  \*  \*